(12) United States Patent
Kenney et al.

(10) Patent No.: US 11,931,424 B2
(45) Date of Patent: Mar. 19, 2024

(54) COMBINATION MCL-1 INHIBITORS WITH ANTI-BODY DRUG CONJUGATES

(71) Applicant: Gilead Sciences, Inc., Foster City, CA (US)

(72) Inventors: Thomas F. Kenney, Seattle, WA (US); Clinton K. Matson, Redmond, WA (US); Chandrasekar Venkataramani, San Carlos, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 17/836,480

(22) Filed: Jun. 9, 2022

(65) Prior Publication Data

US 2022/0409736 A1    Dec. 29, 2022

Related U.S. Application Data

(60) Provisional application No. 63/322,509, filed on Mar. 22, 2022, provisional application No. 63/209,667, filed on Jun. 11, 2021.

(51) Int. Cl.
| | |
|---|---|
| *A61K 47/68* | (2017.01) |
| *A61K 31/519* | (2006.01) |
| *A61K 31/553* | (2006.01) |
| *A61P 11/00* | (2006.01) |
| *A61P 35/00* | (2006.01) |
| *A61P 35/04* | (2006.01) |

(52) U.S. Cl.
CPC ........ *A61K 47/6851* (2017.08); *A61K 31/519* (2013.01); *A61K 31/553* (2013.01); *A61K 47/6803* (2017.08); *A61P 11/00* (2018.01); *A61P 35/00* (2018.01); *A61P 35/04* (2018.01)

(58) Field of Classification Search
CPC ............... A61K 47/68; A61K 47/6851; A61K 47/6803; A61K 31/519; A61K 31/553; A61P 35/00; A61P 35/04
See application file for complete search history.

(56) References Cited

U.S. PATENT DOCUMENTS

| | | | |
|---|---|---|---|
| 7,238,785 B2 | 7/2007 | Govindan et al. | |
| 7,405,295 B2 | 7/2008 | Currie et al. | |
| 7,517,964 B2 | 4/2009 | Govindan et al. | |
| 7,999,083 B2 | 8/2011 | Govindan et al. | |
| 8,084,583 B2 | 12/2011 | Govindan et al. | |
| 8,435,529 B2 | 5/2013 | Govindan et al. | |
| 8,435,539 B2 | 5/2013 | McBride et al. | |
| 9,427,464 B2 | 8/2016 | Nakamura et al. | |
| 9,492,566 B2 | 11/2016 | Goldenberg et al. | |
| 9,850,312 B2 | 12/2017 | Agatsuma et al. | |
| 10,501,555 B2 | 12/2019 | Guerra et al. | |
| 10,703,733 B2 | 7/2020 | Chu et al. | |
| 11,124,582 B2 | 9/2021 | Ambrogelly et al. | |
| 2006/0193865 A1 | 8/2006 | Govindan | |
| 2013/0039861 A1 | 2/2013 | Regino et al. | |
| 2016/0296633 A1 | 10/2016 | Goldenberg et al. | |
| 2017/0021017 A1 | 1/2017 | Chang et al. | |
| 2017/0209594 A1 | 7/2017 | Goldenberg et al. | |
| 2017/0274093 A1 | 9/2017 | Goldenberg et al. | |
| 2018/0110772 A1 | 4/2018 | Govindan et al. | |
| 2018/0185351 A1 | 7/2018 | Goldenberg et al. | |
| 2018/0271992 A1 | 9/2018 | Cardillo et al. | |
| 2019/0048095 A1 | 2/2019 | Tang et al. | |
| 2019/0248917 A1 | 8/2019 | Chang et al. | |
| 2019/0270727 A1* | 9/2019 | Aktoudianakis | C07D 487/08 |
| 2021/0069343 A1 | 3/2021 | Goldenberg et al. | |
| 2021/0093730 A1 | 4/2021 | Sperber et al. | |
| 2023/0015985 A1* | 1/2023 | Kenney | A61K 31/337 |

FOREIGN PATENT DOCUMENTS

| | | |
|---|---|---|
| CN | 108440674 A | 8/2018 |
| CN | 111534585 A | 8/2020 |
| EP | 2573120 B1 | 1/2018 |
| WO | WO-2003/074566 A2 | 9/2003 |
| WO | WO-2007/095749 A1 | 8/2007 |
| WO | WO-2007/147613 A2 | 12/2007 |
| WO | WO-2008/104385 A1 | 9/2008 |
| WO | WO-2008/104386 A2 | 9/2008 |
| WO | WO-2008/130970 A1 | 10/2008 |
| WO | WO-2008/131000 A2 | 10/2008 |
| WO | WO-2010/049816 A2 | 5/2010 |
| WO | WO-2011/068845 A1 | 6/2011 |
| WO | WO-2011/161699 A2 | 12/2011 |
| WO | WO-2012/168944 A1 | 12/2012 |
| WO | WO-2013/068946 A2 | 5/2013 |

(Continued)

OTHER PUBLICATIONS

"TROP2 ADC Intrigues in NSCLC", May 1, 2021, Cancer Discovery, 11(5): OF5. (Year: 2021).*

Okajima, D. et al. "Preclinical efficacy studies of DS-1062a, a novel TROP2-targeting antibody-drug conjugate with a novel DNA topoisomerase I inhibitor DXd", Jun. 2018, Journal of Clinical Oncology, 36(15): e24206. (Year: 2018).*

Ashkenazi, A. et al. (2017), "From basic apoptosis discoveries to advanced selective BCL-2 family inhibitors", Nat Rev Drug Discov. Apr. 2017;16(4):273-284.

Caenepeel, S. et al. (2018), "AMG 176, a Selective MCL1 Inhibitor, Is Effective in Hematologic Cancer Models Alone and in Combination with Established Therapies", Cancer Discov. Dec. 2018;8(12):1582-1597.

(Continued)

*Primary Examiner* — Nelson B Moseley, II
*Assistant Examiner* — Alyssa Rae Stonebraker

(57) ABSTRACT

The present disclosure generally relates to methods of treating or preventing cancer by administering an MCL-1 inhibitor and an antibody-drug conjugate, and optionally one or more additional anti-cancer agents. In particular, the MCL-1 inhibitor can be a compound of formula (I), (II) or (III), or compound A. The antibody-drug conjugate can comprises an anti-Trop-2 antibody and an anti-cancer agent (e.g., SN-38). The combination therapy for treating cancer can have synergistic effect.

15 Claims, 7 Drawing Sheets

(56) References Cited

FOREIGN PATENT DOCUMENTS

| | | |
|---|---|---|
| WO | WO-2013/077458 A1 | 5/2013 |
| WO | WO-2013/132317 A1 | 9/2013 |
| WO | WO-2013/144704 A1 | 10/2013 |
| WO | WO-2014/151634 A1 | 9/2014 |
| WO | WO-2014/163684 A1 | 10/2014 |
| WO | WO-2015/019284 A2 | 2/2015 |
| WO | WO-2015/033299 A1 | 3/2015 |
| WO | WO-2015/033301 A1 | 3/2015 |
| WO | WO-2015/033303 A1 | 3/2015 |
| WO | WO-2015/034820 A1 | 3/2015 |
| WO | WO-2015/036927 A1 | 3/2015 |
| WO | WO-2015/044900 A1 | 4/2015 |
| WO | WO-2015/097123 A1 | 7/2015 |
| WO | WO-2015/098099 A1 | 7/2015 |
| WO | WO-2015/119944 A1 | 8/2015 |
| WO | WO-2015/134605 A1 | 9/2015 |
| WO | WO-2015/160641 A2 | 10/2015 |
| WO | WO-2015/179615 A1 | 11/2015 |
| WO | WO-2016/019232 A1 | 2/2016 |
| WO | WO-2016/033486 A1 | 3/2016 |
| WO | WO-2016/039749 A1 | 3/2016 |
| WO | WO-2016/057624 A1 | 4/2016 |
| WO | WO-2016/077518 A1 | 5/2016 |
| WO | WO-2016/100285 A1 | 6/2016 |
| WO | WO-2016/100608 A1 | 6/2016 |
| WO | WO-2016/126646 A1 | 8/2016 |
| WO | WO-2016/142833 A1 | 9/2016 |
| WO | WO-2016/142835 A1 | 9/2016 |
| WO | WO-2016/142852 A1 | 9/2016 |
| WO | WO-2016/142886 A2 | 9/2016 |
| WO | WO-2016/142894 A1 | 9/2016 |
| WO | WO-2016/149351 A1 | 9/2016 |
| WO | WO-2016/201300 A1 | 12/2016 |
| WO | WO-2016/207216 A1 | 12/2016 |
| WO | WO-2016/207217 A1 | 12/2016 |
| WO | WO-2016/207225 A1 | 12/2016 |
| WO | WO-2016/207226 A1 | 12/2016 |
| WO | WO-2017/002776 A1 | 1/2017 |
| WO | WO-2017/017624 A1 | 2/2017 |
| WO | WO-2017/066227 A1 | 4/2017 |
| WO | WO-2017/070089 A1 | 4/2017 |
| WO | WO-2017/079669 A1 | 5/2017 |
| WO | WO-2017/087678 A2 | 5/2017 |
| WO | WO-2017/087777 A1 | 5/2017 |
| WO | WO-2017/106634 A1 | 6/2017 |
| WO | WO-2017/112730 A1 | 6/2017 |
| WO | WO-2017/125224 A1 | 7/2017 |
| WO | WO-2017/139623 A1 | 8/2017 |
| WO | WO-2017/147410 A1 | 8/2017 |
| WO | WO-2017/176608 A1 | 10/2017 |
| WO | WO-2017/182625 A1 | 10/2017 |
| WO | WO-2017/192961 A1 | 11/2017 |
| WO | WO-2017/205464 A1 | 11/2017 |
| WO | WO-2017/222976 A1 | 12/2017 |
| WO | WO-2018/009505 A1 | 1/2018 |
| WO | WO-2018/013789 A1 | 1/2018 |
| WO | WO-2018/015526 A1 | 1/2018 |
| WO | WO-2018/026971 A1 | 2/2018 |
| WO | WO-2018/036428 A1 | 3/2018 |
| WO | WO-2018/036438 A1 | 3/2018 |
| WO | WO-2018/044783 A1 | 3/2018 |
| WO | WO-2018/044963 A1 | 3/2018 |
| WO | WO-2018/051254 A1 | 3/2018 |
| WO | WO-2018/051255 A1 | 3/2018 |
| WO | WO-2018/073754 A1 | 4/2018 |
| WO | WO-2018/078064 A1 | 5/2018 |
| WO | WO-2018/085750 A2 | 5/2018 |
| WO | WO-2018/102212 A1 | 6/2018 |
| WO | WO-2018/118848 A1 | 6/2018 |
| WO | WO-2018/119221 A1 | 6/2018 |
| WO | WO-2018/119236 A1 | 6/2018 |
| WO | WO-2018/119263 A1 | 6/2018 |
| WO | WO-2018/119266 A1 | 6/2018 |
| WO | WO-2018/119286 A1 | 6/2018 |
| WO | WO-2018102212 A1 * | 6/2018 ............. A61K 31/00 |
| WO | WO-2018/127575 A1 | 7/2018 |
| WO | WO-2018/178226 A1 | 10/2018 |
| WO | WO-2018/178227 A1 | 10/2018 |
| WO | WO-2018/183418 A1 | 10/2018 |
| WO | WO-2018/217227 A1 | 11/2018 |
| WO | WO-2018/234433 A1 | 12/2018 |
| WO | WO-2019/035899 A1 | 2/2019 |
| WO | WO-2019/035911 A1 | 2/2019 |
| WO | WO-2019/035927 A1 | 2/2019 |
| WO | WO-2019/036575 A1 | 2/2019 |
| WO | WO-2019/046150 A1 | 3/2019 |
| WO | WO-2019/173181 A1 | 9/2019 |
| WO | WO-2019/173692 A2 | 9/2019 |
| WO | WO-2019/211721 A1 | 11/2019 |
| WO | WO-2019/222112 A1 | 11/2019 |
| WO | WO-2019/222112 A8 | 11/2019 |
| WO | WO-2019222112 A1 * | 11/2019 ........... A61K 31/553 |
| WO | WO-2020/016662 A2 | 1/2020 |
| WO | WO-2020/078875 A1 | 4/2020 |
| WO | WO-2020/094670 A1 | 5/2020 |
| WO | WO-2020/097577 A1 | 5/2020 |
| WO | WO-2020/099470 A1 | 5/2020 |
| WO | WO-2020/099542 A1 | 5/2020 |
| WO | WO-2020/115183 A1 | 6/2020 |
| WO | WO-2020/123994 A1 | 6/2020 |
| WO | WO-2020/130125 A1 | 6/2020 |
| WO | WO-2020/160157 A1 | 8/2020 |
| WO | WO-2020/236817 A2 | 11/2020 |
| WO | WO-2020/240467 A1 | 12/2020 |
| WO | WO-2020/249063 A1 | 12/2020 |
| WO | WO-2020/254299 A1 | 12/2020 |
| WO | WO-2020/257648 A1 | 12/2020 |
| WO | WO-2020/263830 A1 | 12/2020 |
| WO | WO-2021/021259 A1 | 2/2021 |
| WO | WO-2021/096860 A1 | 5/2021 |
| WO | WO-2021/108254 A1 | 6/2021 |
| WO | WO-2022/031876 A1 | 2/2022 |
| WO | WO-2022/090443 A1 | 5/2022 |
| WO | WO-2022/095851 A1 | 5/2022 |
| WO | WO-2022/245671 A1 | 11/2022 |
| WO | WO-2022/261301 A1 | 12/2022 |
| WO | WO-2023/186968 A1 | 10/2023 |

OTHER PUBLICATIONS

Gaudio, E. et al. (2020), "Targeting CD205 with the antibody drug conjugate MEN1309/OBT076 is an active new therapeutic strategy in lymphoma models", Haematologica. Nov. 1, 2020;105(11):2584-2591.

Gianni, L. et al. (1995), "Nonlinear pharmacokinetics and metabolism of paclitaxel and its pharmacokinetic/pharmacodynamic relationships in humans", J Clin Oncol. Jan. 1995;13(1):180-190.

Godwin, C. et al. (2019), "Anti-Apoptotic BCL-2 Family Members Confer Resistance to Calicheamicin-Based Antibody-Drug Conjugate Therapy of Acute Leukemia", Blood. Nov. 13, 2019;134(Supplement 1):2561.

Jabbour, E. (2019), "Management of Advanced Phase Chronic Myeloid Leukemia", Clinical Lymphoma Myeloma and Leukemia. Sep. 2019; 19(Supplement 1):S1.

Johannes, J. et al. (2017), "Correction to 'Structure Based Design of Non-Natural Peptidic Macrocyclic Mcl-1 Inhibitors'" ACS Med Chem Lett. 2017;8(11):1204.

Johannes, J. et al. (2017), "Structure Based Design of Non-Natural Peptidic Macrocyclic Mcl-1 Inhibitors" ACS Med Chem Lett. 2017;8(2):239-244.

Juin, P. et al. (2013), "Decoding and unlocking the BCL-2 dependency of cancer cells", Nat Rev Cancer. Jul. 2013;13(7):455-465.

Kotschy, A. et al. (2016), "The MCL1 inhibitor S63845 is tolerable and effective in diverse cancer models", Nature. Oct. 2016;(538):477-482.

Merino, D. et al. (2017), "Synergistic action of the MCL-1 inhibitor S63845 with current therapies in preclinical models of triple-negative and HER2-amplified breast cancer", Sci Transl Med. Aug. 2, 2017;9(401):eaam7049.

(56) References Cited

OTHER PUBLICATIONS

Pervushin, N.V. et al. (2020), "Nutrient Deprivation Promotes MCL-1 Degradation in an Autophagy-Independent Manner", Biochemistry (Mosc). Oct. 2020;85(10):1235-1244.

Prichard, M. and Shipman, Jr. C. (1990), "A three-dimensional model to analyze drug-drug interactions", Antiviral Res. Oct.-Nov. 1990;14(4-5):181-205.

Raab, M. et al. (2020), "Boosting the apoptotic response of high-grade serous ovarian cancers with CCNE1 amplification to paclitaxel in vitro by targeting APC/C and the pro-survival protein MCL-1", Int J Cancer. Feb. 15, 2020;146(4):1086-1098.

Rueffli-Brasse, A. and Reed, J. (2017), "Therapeutics targeting Bcl-2 in hematological malignancies", Biochem J. Oct. 23, 2017;474(21):3643-3657.

Szlavik, Z. et al. (2020), "Discovery of S64315, a Potent and Selective Mcl-1 Inhibitor", J Med Chem. Nov. 2020;63(22):13762-13795.

Tron, A. et al. (2018), "Discovery of Mcl-1-specific inhibitor AZD5991 and preclinical activity in multiple myeloma and acute myeloid leukemia", Nature Comm. Dec. 2018;9(1):5341.

Van Der Neut Kolfschoten, M. et al. (2007), "Anti-inflammatory activity of human IgG4 antibodies by dynamic Fab arm exchange", Science. Sep. 14, 2007;317(5844):1554-1557.

Wertz, I. et al. (2011), "Sensitivity to antitubulin chemotherapeutics is regulated by MCL1 and FBW7", Nature. Mar. 3, 2011;471(7336):110-114.

Youle, R. and Strasser, A. "The BCL-2 protein family: opposing activities that mediate cell death", Nat Rev Mol Cell Biol. Jan. 2008;9(1):47-59.

Zoeller, J. et al. (2019), "Neutralization of BCL-2/XL Enhances the Cytotoxicity of T-DM1 In Vivo", Mol Cancer Ther. 18(6):1115-1126.

Intl. Search Report—Written Opinion dated Sep. 19, 2022 for Intl. Appl. No. PCT/US2022/032816.

Lombardi, P. et al. (2023), "Overview of Trop-2 in Cancer: From Pre-Clinical Studies to Future Directions in Clinical Settings", Cancers. 2023;15(6):1744.

Mcmahon, G. (2000), "VEGF Receptor Signaling in Tumor Angiogenesis", Oncologist. 2000;5 Suppl 1:3-10.

Pinedo, H.M. and Slamon, D. (2000), "Introduction: Translational Research: The Role of VEGF in Tumor Angiogenesis", Oncologist. 2000;5 Suppl 1:1-2.

Office Action dated Sep. 15, 2023 for Taiwanese Appl. No. 111121408.

Intl. Preliminary Report on Patentability dated Dec. 21, 2023 for Intl. Appl. No. PCT/US2022/032816.

\* cited by examiner

Paclitaxel Treatment Increases FBXW7 Protein and Decreases MCL1 Protein and MCL1-BAK and MCL1-BIM Protein Dimers in TNBC Cells HCC70 Inhibition and 95% CI Synergy Response Surfaces MDA-MB-468 Inhibition and 95% CI Synergy Response Surfaces HCC1806 Inhibition and 95% CI Synergy Response Surfaces TNBC PDX Model CTG-1909 Tumor Growth TNBC PDX Model CTG-2010 Tumor Growth MDA-MB-468 Tumor Growth

COMBINATION MCL-1 INHIBITORS WITH ANTI-BODY DRUG CONJUGATES

CROSS REFERENCE TO RELATED APPLICATIONS

This application claims the benefit of U.S. provisional application Ser. No. 63/209,667 filed on Jun. 11, 2021, and U.S. provisional application Ser. No. 63/322,509 filed on Mar. 22, 2022. The entire contents of these applications are incorporated herein by reference in their entireties.

FIELD

This application generally relates to combination therapies of MCL-1 inhibitors with antibody-drug conjugates (ADCs) for treatment of cancers. In particular, the antibody is an anti-Trop-2 antibody, and the drug is an anticancer agent.

BACKGROUND

Apoptosis (programmed cell death) is a process for elimination of unwanted or potentially dangerous cells from an organism. Avoidance of apoptosis is critical for the development and sustained growth of tumors. Myeloid cell leukemia 1 protein (MCL-1, also abbreviated Mcl-1 or MCL1) is an antiapoptotic member of the Bcl-2 family of proteins. MCL-1 is overexpressed in many cancers. Overexpression of MCL-1 prevents cancer cells from undergoing apoptosis.

Research has shown that MCL-1 inhibitors can be used to treat a variety of cancers. See, e.g., "The MCL1 inhibitor S63845 is tolerable and effective in diverse cancer models" by A. Kotschy et al., *Nature*, 2016(538): 477-482; "Structure Based Design of Non-Natural Peptidic Macrocyclic Mcl-1 Inhibitors" by J. Johannes et al., *ACS Med. Chem. Lett.*, 2017, 8(2):239-244 & *ACS Med. Chem. Lett.*, 2017, 8(11): 1204; "Synergistic action of the MCL-1 inhibitor S63845 with current therapies in preclinical models of triple-negative and HER2-amplified breast cancer" by D. Merino et al., *Sci. Transl. Med.*, 2017 Aug. 2, 9(401): eaam7049; "Discovery of Mcl-1-specific inhibitor AZD5991 and preclinical activity in multiple myeloma and acute myeloid leukemia" by A. Tron et al., *Nature Comm.* 2018(9): Article No. 5341; "AMG 176, a Selective MCL1 Inhibitor, Is Effective in Hematologic Cancer Models Alone and in Combination with Established Therapies" by S. Caenepeel et al., *Cancer Discov.*, 2018 Dec. 8(12):1582-1597; "Discovery of S64315, a Potent and Selective Mcl-1 Inhibitor" by Z. Szlavik at al., *J. Med. Chem.*, 2020, 63(22):13762-13795.

Recent years, ADCs that comprise tumor-associated monoclonal antibodies (MAbs) and anticancer agents have been developed in the therapy of cancer. For example, sacituzumab govitecan comprises an-Trop-2 antibody and SN-38, disclosed in U.S. Pat. No. 7,999,083.

There remains a need to provide more effective methods for treatment of cancers.

SUMMARY

In some embodiments, provided herein is a method of treating cancer, comprising administering to a human patient in need a therapeutically effective amount of an antibody-drug conjugate, and a therapeutically effective amount of an MCL-1 inhibitor;

wherein the antibody-drug conjugate comprises an anti-Trop-2 antibody and an anticancer agent; and wherein the MCL-1 inhibitor is of Formula (I), or a pharmaceutically acceptable salt thereof:

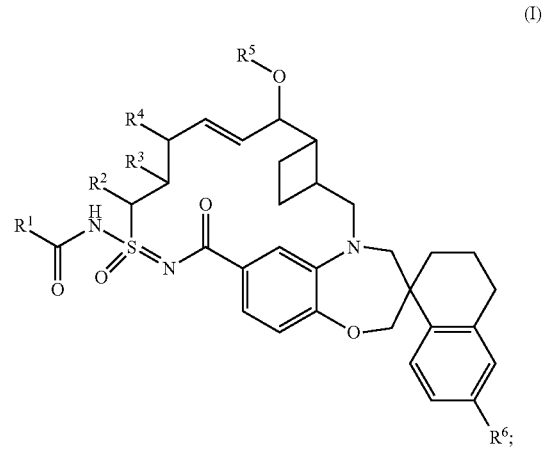

(I)

wherein $R^1$ is 5-10 membered heteroaryl containing 1-2 heteroatoms; wherein each heteroatom is independently selected from nitrogen, sulfur, and oxygen;
the 5-10 membered heteroaryl of $R^1$ is optionally substituted with 1-3 substituents independently selected from halo, hydroxyl, —CN, $C_{1-6}$alkyl, $C_{1-6}$haloalkyl, —$OR^a$, and $C_{3-6}$cycloalkyl; and
each $R^2$, $R^3$, $R^4$, and $R^5$ is independently hydrogen or $C_{1-6}$ alkyl;
$R^6$ is hydrogen or halo; and
$R^a$ is independently hydrogen, $C_{1-6}$alkyl, $C_{2-6}$alkenyl, and $C_{3-10}$cycloalkyl.

DETAILED DESCRIPTION

Definition

Figure 1:
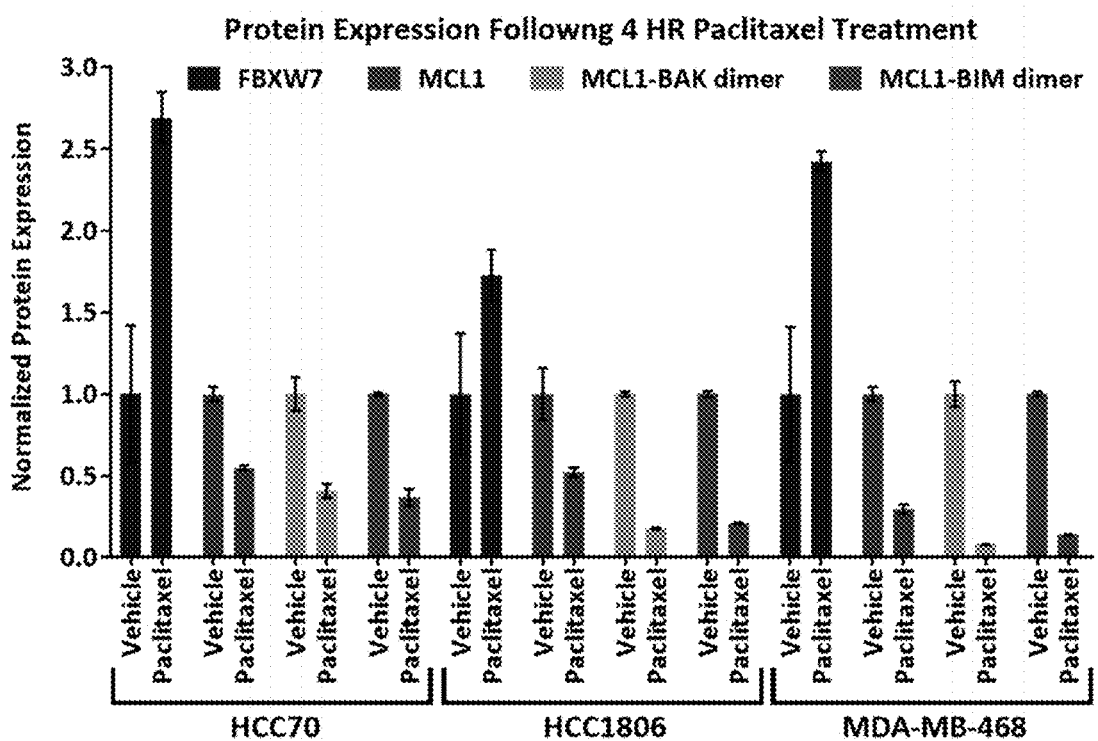
FIG. 1 Paclitaxel Treatment Increases FBXW7 Protein and Decreases MCL1 Protein and MCL1-BAK and MCL1-BIM Protein Dimers in TNBC Cells.

Unless the context requires otherwise, throughout the present specification and claims, the word "comprise" and variations thereof, such as, "comprises" and "comprising" are to be construed in an open, inclusive sense, that is as "including, but not limited to".

A prefix such as "$C_{u-v}$" or ($C_u$-$C_v$) indicates that the following group has from u to v carbon atoms, where u and v are integers. For example, "$C_{1-6}$ alkyl" indicates that the alkyl group has from 1 to 6 carbon atoms.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

The term "substituted" means that one or more hydrogen atoms on a hydrocarbon is replaced with one or more atoms or groups other than hydrogen, provided that the designated carbon atom's or atoms' normal valence is not exceeded. A "substituent" is an atom or group that replaces a hydrogen atom on a hydrocarbon when it is "substituted." Unless specified otherwise, where a group is described as optionally substituted, any substituents of the group are themselves unsubstituted.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). Examples of alkyl groups include, but are not limited to, methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C6-20 aryl), 6 to 12 carbon ring atoms (i.e., C6-12 aryl), or 6 to 10 carbon ring atoms (i.e., C6-10 aryl). Examples of aryl groups include, but are not limited to, phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cycloalkyl" refers to a saturated or partially saturated cyclic alkyl group having a single ring or multiple rings including fused, bridged, and spiro ring systems. Examples of cycloalkyl groups include cyclopropyl, cyclobutyl, cyclopentyl, and cyclohexyl.

"Halo" and "halogen" are used herein to refer to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halogen substituent, which may be the same or different. For example, $C_{1-6}$haloalkyl is a $C_{1-6}$alkyl wherein one or more of the hydrogen atoms of the $C_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

The term "heterocyclyl," "heterocycle," or "heterocyclic" refers to a monoradical or diradical saturated or unsaturated group having a single ring or multiple condensed rings having one or more heteroatoms selected from nitrogen, sulfur, phosphorus, and/or oxygen within the ring. The heteroatoms within the "heterocyclyl" may be oxidized, e.g. —N(O)—, —S(O)—, —S(O)$_2$—. A heterocyclyl may be a single ring or multiple rings wherein the multiple rings may be fused, bridged, or spiro.

"Isomers" are different compounds that have the same molecular formula. Isomers include stereoisomers, enantiomers and diastereomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

The term "prodrug" as used herein is a biologically inactive derivative of a drug that upon administration to the human body is converted to the biologically active parent drug according to some chemical or enzymatic pathway.

"Enantiomers" are a pair of stereoisomers that are non-superimposable mirror images of each other. A 1:1 mixture of a pair of enantiomers is a "racemic" mixture. The symbol "(±)" is used to designate a racemic mixture where appropriate.

"Diastereoisomers" are stereoisomers that have at least two asymmetric atoms, but which are not mirror-images of each other.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "prevention" or "preventing" refers to a regimen that protects against the onset of a disease or disorder such that the clinical symptoms of the disease or disorder do not develop. Thus, "prevention" relates to administration of a therapy to a subject before signs of the disease are detectable in the subject. The subject may be an individual at risk of developing the disease or disorder, such as an individual who has one or more risk factors known to be associated with development or onset of the disease or disorder.

As used herein, the term "therapeutically effective amount" or "effective amount" refers to an amount that is effective to elicit the desired biological or medical response, including the amount of an agent that, when administered to a subject for treating a disease, is sufficient to effect such treatment for the disease. The effective amount will vary depending on the particular agent, and characteristics of the subject to be treated, such as age, weight, etc. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered agents may optionally be lowered due to the combined action (e.g., additive or synergistic effects) of the agents.

As used herein, "co-administration" includes administration of unit dosages of the agents disclosed herein before or after administration of unit dosages of one or more additional therapeutic agents, for example, administration of the agents disclosed herein within seconds, minutes, or hours of the administration of one or more additional therapeutic agents. For example, in some embodiments, a unit dose of an agent of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "conjugate" or "antibody-drug conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in one embodiment, agent(s) or combination of agents described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in one embodiment, compound(s) or combination of compounds described herein may be administered by oral route alone or in combination with administration of certain components of the treatment regimen by IV or parenteral routes.

Also provided herein are pharmaceutically acceptable salts, hydrates, solvates, tautomeric forms, polymorphs, and prodrugs of the compounds of formula (I) described herein. "Pharmaceutically acceptable" or "physiologically acceptable" refer to compounds, salts, compositions, dosage forms and other materials which are suitable for human pharmaceutical use.

Compounds of Formula (I) described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Non-limiting examples of "pharmaceutically acceptable salts" of the compounds of formula (I) disclosed herein also include salts derived from an appropriate base, such as an alkali metal (for example, sodium, potassium), an alkaline earth metal (for example, magnesium), ammonium and NX$_4^+$ (wherein X is C$_1$-C$_4$ alkyl). Also included are base addition salts, such as sodium or potassium salts.

MCL-1 Inhibitors

Compounds

In some embodiments, provided herein is a method of treating cancer, comprising administering to a human patient in need a therapeutically effective amount of an antibody-drug conjugate, and a therapeutically effective amount of an MCL-1 inhibitor;

wherein the antibody-drug conjugate comprises an anti-Trop-2 antibody and an anticancer agent; and wherein the MCL-1 inhibitor is of Formula (I), or a pharmaceutically acceptable salt thereof:

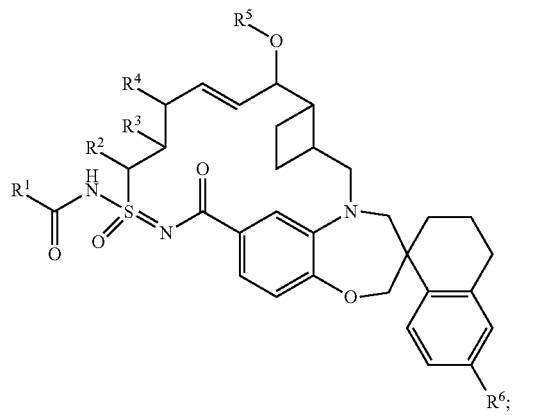

(I)

wherein R$^1$ is 5-10 membered heteroaryl containing 1-2 heteroatoms; wherein each heteroatom is independently selected from nitrogen, sulfur, and oxygen;
the 5-10 membered heteroaryl of R$^1$ is optionally substituted with 1-3 substituents independently selected from halo, hydroxyl, —CN, —OW, and C$_{3-6}$cycloalkyl; and each R$^2$, R$^3$, R$^4$, and R$^5$ is independently hydrogen or C$_{1-6}$ alkyl;
R$^6$ is hydrogen or halo; and
R$^7$ is independently hydrogen, C$_{1-6}$alkyl, C$_{2-6}$alkenyl, and C$_{3-10}$cycloalkyl.

In some embodiments of methods described herein, the MCL-1 inhibitor is a compound of Formula (II), or a pharmaceutically acceptable salt thereof:

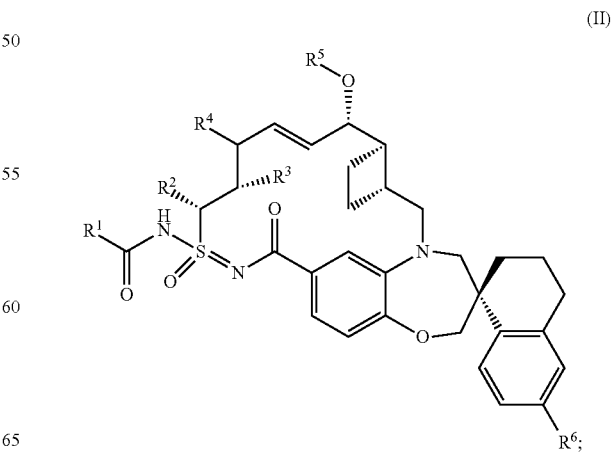

(II)

each $R^1$, $R^2$, $R^3$, $R^4$, $R^5$, and $R^6$ is defined as above, or elsewhere in this disclosure.

In some embodiments, the MCL-1 inhibitor is a compound of Formula (III),

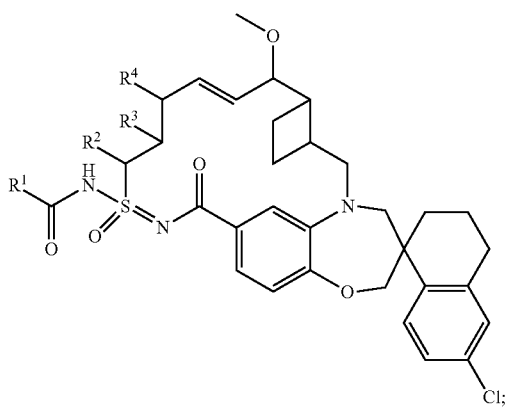

or a pharmaceutically acceptable salt thereof:

In some embodiments, the MCL-1 inhibitor is a compound of Formula (I), Formula (II), or Formula (III), or pharmaceutically acceptable salt thereof, $R^2$ is hydrogen. In some embodiments, $R^2$ is $C_{1-3}$alkyl. $R^2$ is methyl.

In some embodiments, the MCL-1 inhibitor is a compound of Formula (I), Formula (II), or Formula (III), or pharmaceutically acceptable salt thereof, $R^3$ is $C_{1-3}$alkyl. In some embodiments, $R^3$ is methyl.

In some embodiments, the MCL-1 inhibitor is a compound of Formula (I), Formula (II), or Formula (III), or pharmaceutically acceptable salt thereof, $R^4$ is hydrogen. In some embodiments, $R^5$ is $C_{1-3}$ alkyl. In some embodiments, $R^5$ is methyl. In some embodiments, $R^6$ is Cl.

In some embodiments, the MCL-1 inhibitor is a compound of Formula (I), Formula (II), or Formula (III), or pharmaceutically acceptable salt thereof, $R^1$ is

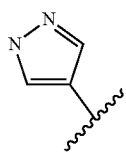

optionally substituted with $C_{1-4}$alkyl and $C_{1-4}$alkoxyl. In some embodiments, $R^1$ is

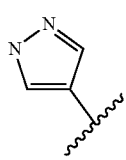

optionally substituted with —$CH_3$ and —$OCH_3$. In some embodiments, $R^1$ is

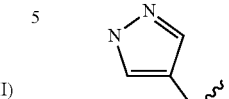

substituted with —$CH_3$ and —$OCH_3$. In some embodiments, $R^1$ is

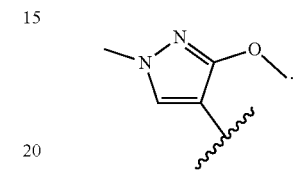

In some embodiments, the MCL-1 inhibitor is compound A, N-[(4S,7aR,9aR,10S,11E,14S)-6'-chloro-10-methoxy-14-methyl-16-oxido-18-oxo-3',4',7,7a,8,9,9a,10,13,14,15,18-dodecahydro-2'H-spiro[1,19-(ethanediylidene)-16λ⁴-cyclobuta[i][1,4]oxazepino[3,4-f][1,2,7]thiadiazacyclohexadecine-4,1'-naphthalen]-16-yl]-3-methoxy-1-methyl-1H-pyrazole-4-carboxamide, and has the following structure:

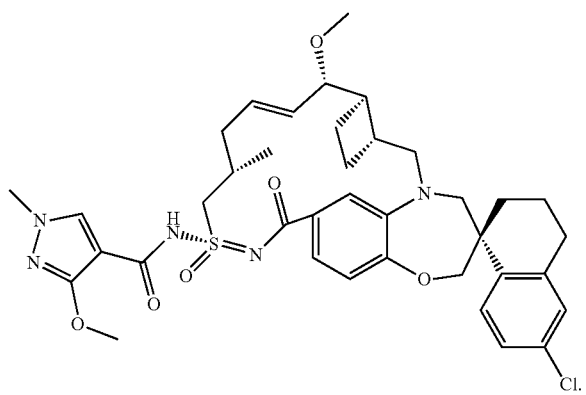

compound A is described in Example 154 of U.S. Pat. No. 10,703,733 and WO 2019/222112, which are incorporated herein by reference.

In some embodiments, the MCL-1 inhibitors that can be administered include, but are not limited to, the compounds disclosed in U.S. Pat. No. 10,703,733 (Gilead Sciences), AMG-397, AMG-176, PRT-1419, 564315, AZD59991, ABBV-467, the compounds disclosed in WO2019222112 (Gilead Sciences), WO2021096860 (Gilead Sciences), WO2017147410 (Amgen), WO2019046150 (Amgen), WO2019036575 (Amgen), WO2021021259 (Amgen), WO2019173181 (Amgen), WO2018183418 (Amgen), WO2016033486 (Amgen), WO2018178226 (AstraZeneca), WO2017182625 (AstraZeneca), WO2018178227 (AstraZeneca), WO2020099470 (AstraZeneca), WO2019211721 (AstraZeneca), WO2020097577 (Prelude), WO2020123994 (Prelude), WO2008104386 (AbbVie), WO2008104385 (AbbVie), WO2008131000 (AbbVie), WO2008130970 (AbbVie), WO2019035911 (AbbVie), WO2019035927 (AbbVie), WO2019035899 (AbbVie), WO2010049816 (Servier), WO2020160157 (Servier), WO2020115183 (Servier), WO2020099542 (Servier), WO2015097123 (Servier), WO2018078064 (Servier), WO2020254299 (Servier), WO2018127575 (Servier), WO2018234433 (Servier), WO2018015526 (Servier), WO2016207225 (Servier), WO2020078875 (Servier), WO2017125224 (Servier), WO2020236817 (Servier), WO2016207226 (Servier), WO2016207217 (Servier), WO2016207216 (Servier), and WO2007147613 (Novartis).

In some embodiments, the MCL-1 inhibitor is selected from AMG-397, AMG-176, PRT-1419, and 564315. In some embodiments, the MCL-1 inhibitor is AMG-176. In some embodiments, the MCL-1 inhibitor is AMG-397. In some embodiments, the MCL-1 inhibitor is PRT-1419. In some embodiments, the MCL-1 inhibitor is 564315.

The compounds disclosed herein may contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, as well as their racemic and optically pure forms. Optically active (+) and (−), or (R)- and (S)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Likewise, all tautomeric forms are also intended to be included.

Formulations

In the methods provided herein, the MCL-1 inhibitor can be administered as a pharmaceutical composition. In certain embodiments, the pharmaceutical composition comprises a compound of Formula (I), (II), (III), or compound A, or a pharmaceutically acceptable salt thereof, and a pharmaceutically acceptable excipient. In certain embodiments, the pharmaceutical composition comprises one or more additional therapeutic agents, as described in more detail below.

Pharmaceutical compositions comprising the MCL-1 inhibitors disclosed herein, or pharmaceutically acceptable salts thereof, may be prepared with one or more pharmaceutically acceptable excipients which may be selected in accord with ordinary practice. "Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In certain embodiments, pharmaceutical compositions are provided as a solid dosage form, including a solid oral dosage form, such as a tablet. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

Pharmaceutical compositions disclosed herein include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

In some embodiments, the tablets comprise the compound A in strengths of 5 mg and 25 mg. In some embodiments, the tablets contain copovidone, lactose monohydrate, microcrystalline cellulose, crospovidone, magnesium stearate, polyvinyl alcohol, titanium dioxide, polyethylene glycol, and talc.

Antibody-Drug Conjugate (ADC)

In some embodiments, the method of treating cancer disclosed herein comprises administering to a human patient in need a therapeutically effective amount of an antibody-drug conjugate, and a therapeutically effective amount of an MCL-1 inhibitor. In some embodiments, the antibody-drug conjugate comprises an anti-Trop-2 antibody and an anti-cancer agent.

In some embodiments, the antibody-drug conjugate is sacituzumab govitecan that is disclosed in U.S. Pat. No. 7,999,083. In some embodiments, the ADC includes the antibody-drug conjugates disclosed in U.S. Pat. No. 7,999,083, which is incorporated herein by reference. In some embodiments, sacituzumab govitecan is sacituzumab govitecan-hziy.

In some embodiments, the anti-Trop-2 antibody-drug conjugate is datopotamab deruxtecan. In some embodiments, the anti-Trop-2 antibody-drug conjugate that can be administered include, but not limited to, the conjugates disclosed in U.S. Pat. No. 9,850,312, WO 20240467, and WO 18036438.

In some embodiments, the antibody moiety of the ADC is an IgG antibody or antigen-binding antibody fragment. The antibody can be of various isotypes, preferably human IgG 1, 55 IgG2, IgG3 or IgG4, more preferably comprising human IgG 1 hinge and constant region sequences. The antibody or fragment thereof can be a chimeric human-mouse, a chimeric human-primate, a humanized (human framework and murine hypervariable (CDR) regions), or fully human anti-60 body, as well as variations thereof, such as half-IgG4 anti-bodies (referred to as "unibodies"), as described by van der Neut Kolfschoten et al. (Science 2007; 317:1554-1557). More preferably, the antibody or fragment thereof may be designed or selected to comprise human constant region 65 sequences that belong to specific allotypes, which may result in reduced immunogenicity when the antibody or ADC is administered to a human subject. Preferred allotypes for administration include a non-Glm1 allotype (nGlm1), such as Glm3, Glm3,1, Glm3,2 or Glm3, 1,2. More preferably, the allotype is selected from the group consisting of the nGlm1, Glm3, nGlm1, 2 and Km3 allotypes.

In some embodiments, the antibody moiety of the ADC is the anti-Trop-2 antibody. In some embodiments, the anti-Trop-2 antibody includes, but is not limited to, TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Klus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), and KD-065 (Nanjing KAEDI Biotech).

Further examples of anti-TROP-2 therapeutics include, but are not limited to, E1.BB.3z-92MI (Immunomedics/Gilead), anti-Trop-2 CAR-T (Gilead), Trop-2CAR-T (Hangzhou Lonzyme Biological Technology), ARB-001 (Arbele), and MT-103 (Myeloid Therapeutics).

Examples of anti-TROP-2 antibodies include, but are not limited to, those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Ser. No. 10/501,555 (Abruzzo Theranostic/Oncoxx), WO2018036428 (Sichuan Kelun Pharma), WO2013068946 (Pfizer), WO2007095749 (Roche), and WO2020094670 (SynAffix).

Further examples of anti-TROP-2 therapeutics include, but are not limited to, those described in WO2016201300 (Gilead), and CN108440674 (Hangzhou Lonzyme Biological Technology).

In some embodiments, the anti-Trop-2 antibody is selected from hRS7, Trop-2-XPAT, and BAT-8003.

In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. Additional disclosures of hRS7 include International Patent Publication WO2003074566.

In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A.

In some embodiments, the drug moiety of antibody-drug conjugate is a chemotherapeutic agent. In some embodiments, the chemotherapeutic agent is selected from doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38.

Formulation

Suitable routes of administration of the ADCs include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. Alternatively, one may administer the compound in a local rather than systemic manner, for example, via injection of the compound directly into a solid tumor.

ADCs can be formulated according to known methods to prepare pharmaceutically useful compo-sitions, whereby the ADC is combined in a mixture with a pharmaceutically suitable excipient. ADC can be formulated for intravenous administration via, for example, bolus injection, slow infusion or continuous infusion. In some embodiments, the antibody is infused over a period of less than about 4 hours. In some embodiments, the antibody is infused over a period of less than about 3 hours. For example, the first 25-50 mg could be infused within 30 minutes, or 15 minutes, and the remainder infused over the next 2-3 hrs. Formulations for injection can be presented in unit dosage form, e.g., in ampoules or in multidose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Methods of Treatment

In some embodiments, the present disclosure provides a combination of an MCL-1 inhibitor and an antibody-drug conjugate for treatment of cancers. In some embodiments, the antibody-drug conjugate is sacituzumab govitecan, and the MCL-1 inhibitor is compound A.

In some embodiments, the cancer is a Trop-2 expressing cancer.

In some embodiments, the cancer is selected from breast cancer, cervical cancer, colorectal, endometrial cancer, epithelial ovarian cancer, esophageal cancer, follicular thyroid cancer, gastric or gastroesophageal junction adenocarcinoma, head and neck cancers, hepatocellular carcinoma, non-small-cell lung cancer, ovarian cancer, prostatic cancer, renal cell cancer, small-cell lung cancer, urothelial cancer, and urinary cancer.

In some embodiments, the cancer is selected from triple-negative breast cancer (TNBC), HR+/HER2− breast cancer, urothelial cancer, nonsquamous non-small-cell lung cancer (NSCLC), small cell lung cancer (SCLC), head and neck squamous cell carcinoma (HNSCC), and muscle invasive bladder cancer (MIBC).

In some embodiments, the cancer is metastatic. In some embodiments, the cancer is refractory.

In some embodiments, the cancer is selected from metastatic nonsquamous non-small-cell lung cancer (mNSCLC), metastatic triple-negative breast cancer (mTNBC), and metastatic soft tissue sarcomas with nonspecific histologies.

In some embodiments, the cancer is metastatic nonsquamous non-small-cell lung cancer (mNSCLC). In some embodiments, the cancer is metastatic triple-negative breast cancer (mTNBC). In some embodiments, the cancer is metastatic soft tissue sarcomas with nonspecific histologies.

In some embodiments, the human patient has received at least one other therapy prior to treatment with the combination therapy of the MCL-1 inhibitor and the antibody-drug conjugate. In some embodiments, the human patient has failed to the other therapy prior to treatment disclosed herein. In some embodiments, the human patient has failed to one chemotherapy.

In some embodiments, the human patient has failed to therapy with an anti-PD1 or an anti-PDL1 agent prior to treatment with the combination therapy of the MCL-1 inhibitor and the antibody-drug conjugate.

In some embodiments, the compound of formula (I), or a pharmaceutically acceptable salt thereof, and the antibogy-drug conjugate are administered simultaneously, or separately.

In some embodiments, the MCL-1 inhibitor is the compound A. Generally, the dosage of an administered compound A for humans will vary depending upon such factors as the patient's age, weight, height, sex, general medical condition and previous medical history. It may be desirable to provide the recipient with a dosage of the antibody-conjugate that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. In some embodiments, dosages include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, 24 mg/kg, 26 mg/kg, 28 mg/kg, 30 mg/kg, 35 mg/kg, 40 mg/kg, 45 mg/kg, 50 mg/kg, 55 mg/kg, 65 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 220 mg/kg, 240 mg/kg, 250 mg/kg, 260 mg/kg, 280 mg/kg, 300 mg/kg, 350 mg/kg, 400 mg/kg, 450 mg/kg, 550 mg/kg, 600 mg/kg, 650 mg/kg, 700 mg/kg, 750 mg/kg, and 800 mg/kg. Any amount in the range of 1 to 300 mg/kg may be used. Any amount in the range of 1 to 100 mg/kg may be used.

In some embodiments, the dosage is administered multiple times, once or twice a week. A minimum dosage schedule of 4 weeks, 8 weeks, 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy ollowed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

In some embodiments, the compound of Formula (I) or a pharmaceutically acceptable salt thereof is administered orally.

In some embodiments, the amount of compound of Formula (I) or a pharmaceutically acceptable salt thereof is administered at a dosage of about 5 mg/kg, 15 mg/kg, or 50 mg/kg.

In some embodiments, the compound of Formula (I) or a pharmaceutically acceptable salt thereof is administered at a dosage of about 5 mg/kg.

In some embodiments, the compound of Formula (I) or a pharmaceutically acceptable salt thereof is administered in a 21-day cycle with 2 days dosing followed by 5 days off.

In some embodiments, the compound of Formula (I) or a pharmaceutically acceptable salt thereof is administered on days 1, 2, 8, 9, 15, and 16 of each 21-day cycle for up to 105 weeks.

In some embodiments, the antibody-drug conjugate is administered as an intravenous infusion.

Generally, the dosage of an administered the antibody-drug conjugate for humans will vary depending upon such factors as the patient's age, weight, height, sex, general medical condition and previous medical history. It may be desirable to provide the recipient with a dosage of the antibody-conjugate that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. In some embodiments, dosages include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg, and 24 mg/kg. Any amount in the range of 1 to 24 mg/kg may be used. In some embodiments, the dosage is administered multiple times, once or twice a week. A minimum dosage schedule of 4 weeks, 8 weeks, 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy ollowed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

In some embodiments, the antibody-drug conjugate may be administered as one dosage every 2 or 3 weeks, repeated for a total of at least 3 dosages. Or, twice per week for 4-6 weeks. If the dosage is lowered to approximately 200-300 mg/m² (340 mg per dosage for a 1.7-m patient, or 4.9 mg/kg for a 70 kg patient), it may be administered once or even twice weekly for 4 to 10 weeks. In some embodiments, the dosage schedule may be decreased, namely every 2 or 3 weeks for 2-3 months. It has been determined, however, that even higher doses, such as 2 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In some embodiments, the antibody-drug conjugate dosage is administered on days 1, and 8 of each 21-day cycle.

In some embodiments, the antibody-drug conjugate is administered as a dosage of between about 4 mg/kg and about 12 mg/kg. In some embodiments, the antibody-drug conjugate is administered as a dosage of between about 8 mg/kg and about 12 mg/kg.

In some embodiments, the antibody-drug conjugate is administered as a dosage of about 8 mg/kg, about 10 mg/kg, or about 12 mg/kg.

In some embodiments, the antibody-conjugate is sacituzumab govitecan. In some embodiments, the dosage of sacituzumab govitecan is in the range of from about 2 mg/kg to 20 mg/kg as a single intravenous infusion. In some embodiments, the dosage of sacituzumab govitecan is in the range of from about 6 mg/kg to 10 mg/kg as a single intravenous infusion. In some embodiments, dosages include 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg, 19.5 mg/kg, and 20 mg/kg. In some embodiments, the dosage of the antibody-conjugate is 7.5 mg/kg.

In some embodiments, the method further comprises one or more additional therapeutic modalities selected from antibodies, conjugates, gene therapy, chemotherapy, radiation therapy, surgery therapy, BTK inhibitors, and checkpoint inhibitors.

In some embodiments, the method further comprises radiation therapy.

In some embodiments, the method further comprises administering one or more additional therapeutic agents. In some embodiments, the additional therapeutic agent is selected from a chemotherapeutic agent, a checkpoint inhibitor, an FLT3 agonist, and a BTK inhibitor.

In some embodiments, the checkpoint inhibitor is selected from anti-PD-1 agents, anti-PD-L1 agents, anti PD-1/PD-L1 interaction inhibitors, anti-CTLA4 agents, and anti-TIGIT agents.

In some embodiments, FLT3 agonist is GS-3583. FLT3 agonist also includes CDX-301 and the agents disclosed in PCT publication WO2020/263830A1.

In some embodiments, FLT3 agonist is a Fc fusion protein disclosed in WO2022031876.

In some embodiments, the present disclosure provides a method for treatment of cancers. The method comprises administering an MCL-1 inhibitor and an antibody-drug conjugate for treatment of cancers; and the method further comprises administering one or more additional therapeutic agents, provided that the additional therapeutic agent is not an FLT3 agonist. In some embodiments, the additional therapeutic agent is not a FLT3-Fc fusion protein. In some embodiments, the antibody-drug conjugate is sacituzumab govitecan, and the MCL-1 inhibitor is compound A; and the additional therapeutic agent is not an FLT3 agonist. In some embodiment, the additional therapeutic agent is not an FLT3 agonists disclosed in WO2020/263830. In some embodiment, the additional therapeutic agent is not the fusion protein comprising the amino acid sequence of SEQ ID NO:14 in U.S. patent Ser. No. 11/124,582.

In some embodiments, the method comprises administering a checkpoint inhibitor. In some embodiments, the checkpoint inhibitor is selected from anti-PD-1 agents, anti-PD-L1 agents, anti PD-1/PD-L1 interaction inhibitors, anti-CTLA4 agents, and anti-TIGIT agents. In some embodiments, the checkpoint inhibitor is selected from nivolumab, pembrolizumab, atezolizumab, zimberelimab and pidilizumab. In some embodiments, the checkpoint inhibitor is selected from ipilimumab, lambrolizumab, tremelimumab, durvalumab, avelumab, domvanalimab, and tiragolumab.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, ALN-PDL, BMS-936559, CK-301, PF-06801591, BGB-108, BGB-A317 (tislelizumab), GLS-010 (WBP-3055), AK-103 (HX-008), GB-226, AK-105, CS-1003, HLX-10, MGA-012, BI-754091, PDR-001, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181, PD1-PIK, BAT-1306, RO-6084 (PD-L1 antisense oligonucleotide), STI-1110, GX-P2, RG-7446, mDX-400, (MSB0010718C), CX-072, CBT-502, TSR-042 (dostarlimab), MSB-2311, JTX-4014, BGB-A333, SHR-1316, CS-1001 (WBP-3155), MEDI-0680, envafolimab (KN-035), KD-033, KY-1003, IBI-308 (sintilimab), HLX-20, KL-A167, STI-A1014, STI-A1015 (IMC-001), BCD-135, FAZ-053, TQB-2450, MDX1105-01, MSB-0010718C, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), GNS-1480 (Epidermal growth factor receptor antagonist; Programmed cell death ligand 1 inhibitor), M-7824 (PD-L1/TGF-β bifunctional fusion protein), and INBRX-105 (4-1BB/PDL1).

Examples of PD-1 inhibitors include, but are not limited to, the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), and WO2018026971 (Arising International).

The PD-1/PD-L1 inhibitors can be administered in any suitable amount known by one of skill in the art. In some embodiments, the compound of Formula I is administered to the subject in an amount 0.1 to 1000 mg. Representative amounts of the PD-1/PD-L1 inhibitor administered to the subject include, but are not limited to, from 0.1 to 500 mg, 1 to 100 mg, 1 to 50 mg, or from 10 to 50 mg. Other amounts of the PD-1/PD-L1 inhibitor administered to the subject include, but are not limited to, about 1 mg, or 2, 3, 4, 5, 6, 7, 8, 9, 10, 15, 20, 25, 30, 35, 40, 45, 50, 55, 60, 65, 70, 75, 80, 85, 90, 95, or about 100 mg.

In some embodiments, the methods as described herein further comprises administering an anti-TIGIT antibody, such as BMS-986207, RG-6058, domvanalimab, AB308, or AGEN-1307.

In some embodiments, the methods as described herein further comprises administering a BTK (Bruton's Tyrosine kinase) inhibitor. An example of such BTK inhibitor is compounds disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951, tirabrutinib (ONO-4059), PRN-1008, spebrutinib (CC-292), and TAK-020. In some embodiments, the BTK inhibitor is selected from acalabrutinib, tirabrutinib, zanubrutinib, and PCI-32765.

In some embodiments, the method further comprises administering a chemotherapeutic agent. In some embodiments, the anti-cancer agent is selected from doxorubcin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic agent is docetaxel. In some embodiments, the chemotherapeutic agent is gemcitabine. In some embodiments, the chemotherapeutic agent is paclitaxel.

In certain embodiments, when an agent of the present disclosure is combined with one or more additional therapeutic agents as described herein, the components of the composition are administered as a simultaneous or sequential regimen. When administered sequentially, the combination may be administered in two or more administrations In certain embodiments, when an agent of the present disclosure is combined with one or more additional therapeutic agents as described herein, the components of the composition are administered as a simultaneous or sequential regimen. When administered sequentially, the combination may be administered in two or more administrations. In certain embodiments, when an agent of the present disclosure is combined with one or more additional therapeutic agents as described herein, the components of the composition are administered as a simultaneous or sequential regimen. When administered sequentially, the combination may be administered in two or more administrations.

Co-administration of an agent disclosed herein with one or more additional therapeutic agents generally refers to simultaneous or sequential administration of an agent disclosed herein and one or more additional therapeutic agents, such that therapeutically effective amounts of each agent are present in the body of the patient.

Co-administration includes administration of unit dosages of the agents disclosed herein before or after administration of unit dosages of one or more additional therapeutic agents. The agent disclosed herein may be administered within seconds, minutes, or hours of the administration of one or more additional therapeutic agents. For example, in some embodiments, a unit dose of an agent disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of an agent disclosed herein within seconds or minutes. In some embodiments, a unit dose of an agent disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an agent disclosed herein.

In some embodiments, the present disclosure provides a method of treating or preventing cancer. In certain embodiments, the present disclosure provides a method of treating or preventing cancer comprising administering to a patient a therapeutically effective amount a compound of Formula (I), or a pharmaceutically acceptable salt thereof, to the individual. In some embodiments, the cancer is a hematologic malignancy. In some embodiments, the cancer is multiple myeloma. In some embodiments, the cancer is selected from the group consisting of breast cancer, colorectal cancer, skin cancer, melanoma, ovarian cancer, kidney cancer, small cell lung cancer, non-small cell lung cancer, lymphoma, and leukemia. In some embodiments, the cancer is acute myeloid leukemia.

In some embodiments, the cancer is prostate cancer. In some embodiments, the cancer is bladder cancer.

EXAMPLES

Example 1: MCL-1 Inhibitor In Vitro Synergy with SN-38 in TNBC and NSCLC Cell Lines To test the combination potential between compound A and SN-38 (topoisomerase inhibitor), in vitro studies were performed in a panel of triple negative breast cancer (TNBC, n=3) and non-small cell lung cancer (NSCLC, n=2) cell lines using a Bliss Independence model of synergy. Cells were exposed to a dose titration matrix of each compound alone and in combination for 72 hours and then cell viability was determined by Cell Titer Glo reagent. Strong Bliss synergy scores (>100) were observed across all cell lines tested.

Materials and Methods
Cell Culture and Reagents

HCC70 (ATCC® CRL-2315), HCC1806 (ATCC® CRL-2335), HCC1187 (ATCC® CRL-2322), NCI-H522 (ATCC® CRL-5810) and H820 (ATCC® HTB-181) cell lines were thawed from liquid nitrogen storage and maintained according to ATCC guidelines in RPMI-1640 (Gibco-12633)+10% HI-FBI (Gibco-16140)+Pen/Strep (100× Gibco-15140). Cells were passaged according to ATCC guidelines with 0.25% Trypsin/EDTA (1× GIBCO-25200).

SN-38 and compound A stocks (provided by Gilead sample bank) were dispensed directly into treatment wells using D300e Digital Dispenser (vendor) with DMSO (Sigma-D2438) as vehicle control to 0.1% v/v.

Viability assessments were performed using Cell Titer Glo™ (Promega #G9241) according to manufactures microwell plate protocol and read for luminescence on Biotek Synergy Neo2 plate reader.

Cell Viability Combination Assays

For synergy matrix assays, cell lines were seeded 5,000 cells per well in clear-bottomed white 96-well plates (Corning #3909) in 100 µL of recommended cell culture medium. Treatment map consisted of single agent dose responses for the compound A (seven 3-fold dilutions plus no treatment control) or SN-38 (nine 3-fold dilutions plus no treatment control) and a checkerboard matrix of 63 distinct combinations. Concentration ranges were selected based on the relative sensitivities of each cell line to the compounds. Five plates were used for each combination to generate enough replicates to calculate synergy scores with a 95% confidence interval (95% CI).

Compounds and DMSO vehicle were applied to cells using an HP D300 dispenser to aliquot directly into media according to checkerboard matrix and incubated at 37° C./5% $CO_2$/100% Relative Humidity for 72 hours prior to measurement of viability by Cell Titer Glo.

Data Analysis

Combination viability data was evaluated for synergy using an excel template described by Prichard and Shipman {Prichard 1990}. Specifically, single component dose curves of SN-38 and compound A were normalized to percent viability on each plate and averaged across five technical replicates to calculate theoretical additive killing of combinations according to the principle of Bliss Independence. Calculated values were compared to experimental results generated in the sixty-three-concentration checkerboard. Synergy or antagonism scores were generated depending on whether the observed growth inhibition was greater than or less than the calculated values, respectively.

For example, if two compounds (B) and (C) at given concentrations each resulted in 60% inhibition, their theoretical additive inhibition would be 84% according the following Bliss Independence formula:

$$60\%_B + 60\%_C * (100\% - 60\%_B) = 84\%_{B+C}$$

If the experimental result was greater than calculated (e.g. 90% inhibition) then the difference [6%] would be added to the synergy score. If the result was less (e.g. 78% inhibition) then the difference [6%] would be added to the antagonism score.

These differences were summed up across the whole checkerboard (sixty-three wells) to give cumulative synergy and antagonism scores with units of $\mu M^2\%$ to reflect the 2D surface of the dose responses. A 95% confidence interval adjustment was applied to the synergy and antagonism scores and each sum was compared to a scale based on the original method: scores greater than 50 were considered moderate synergy and scores greater than 100 were considered strong synergy and likely to show combination effect in vivo {Prichard 1990}.

Data for combination assays is presented in three formats. Synergy score @ 95% confidence interval averaged from n=2 assays. Example tabulated and graphical percent inhibition matrix for each cell line. Example tabulated and graphical synergy matrix @ 95% confidence interval for each cell line.

To test the combination potential between compound A and SN-38 (topoisomerase inhibitor), in vitro studies were performed in a panel of TNBC (n=3) and NSCLC (n=2) cell lines using a Bliss Independence model of synergy. Cells were exposed to a dose titration matrix of each compound alone and in combination for 72 hours and then cell viability was determined by Cell Titer Glo reagent. Strong Bliss synergy scores (>100) were observed across all cell lines tested.

TABLE 1

Compound A + SN-38 Bliss Synergy Scores at 95% Confidence Interval

| Cancer Cell Line | 95% Bliss Synergy Scores | |
|---|---|---|
| | Average | Replicates |
| HCC70 (TNBC) | 442 | 348, 537 |
| HCC1806 (TNBC) | 246 | 247, 245 |
| HCC1187 (TNBC) | 245 | 194, 360, 180 |
| H522 (NSCLC) | 614 | 555, 672 |
| H820 (NSCLC) | 183 | 150, 216 |

TABLE 2

HCC70 Percent Inhibition Results (n = 5) 1$^{st}$ Replicate

| Compound | SN-38 (μM) | | | | | | | | | |
|---|---|---|---|---|---|---|---|---|---|---|
| A (μM) | 0.0000 | 0.0002 | 0.0005 | 0.0014 | 0.0041 | 0.0123 | 0.0370 | 0.1111 | 0.3333 | 1.0000 |
| 2.000 | 72.1 | 73.9 | 75.3 | 80.3 | 87.1 | 90.2 | 92.2 | 94.9 | 99.2 | 99.8 |
| 0.667 | 61.2 | 60.7 | 64.8 | 70.6 | 77.7 | 81.7 | 84.4 | 90.1 | 97.3 | 99.2 |
| 0.222 | 47.8 | 51.1 | 52.0 | 58.7 | 68.5 | 70.4 | 76.1 | 82.2 | 92.6 | 98.8 |
| 0.074 | 17.3 | 19.2 | 15.5 | 30.7 | 39.8 | 48.4 | 52.7 | 64.1 | 80.6 | 96.3 |
| 0.025 | −1.4 | 0.7 | −0.2 | −1.5 | 1.1 | 7.5 | 19.1 | 39.6 | 57.8 | 89.1 |
| 0.008 | −0.3 | −0.5 | −4.2 | −5.3 | −10.5 | −6.4 | 6.7 | 24.4 | 40.5 | 82.7 |
| 0.003 | 0.6 | 0.0 | −2.2 | −7.3 | −7.9 | −13.0 | −0.5 | 15.7 | 37.2 | 78.6 |
| 0.000 | 0.0 | −1.4 | −3.6 | −7.0 | −9.5 | −10.3 | 2.6 | 18.9 | 38.2 | 79.7 |

TABLE 3

HCC70 Percent Inhibition Results (n = 5) 2$^{nd}$ Replicate

| Compound | SN-38 (μM) | | | | | | | | | |
|---|---|---|---|---|---|---|---|---|---|---|
| A (μM) | 0.0000 | 0.0002 | 0.0005 | 0.0014 | 0.0041 | 0.0123 | 0.0370 | 0.1111 | 0.3333 | 1.0000 |
| 2.000 | 71.2 | 71.9 | 72.6 | 76.4 | 86.7 | 89.4 | 93.4 | 95.6 | 98.6 | 99.7 |
| 0.667 | 59.9 | 59.1 | 60.3 | 64.6 | 77.7 | 83.3 | 87.3 | 93.0 | 97.6 | 99.5 |
| 0.222 | 44.9 | 43.7 | 46.0 | 54.0 | 67.7 | 74.5 | 80.5 | 84.7 | 94.6 | 99.4 |
| 0.074 | 17.6 | 19.5 | 18.4 | 25.3 | 40.5 | 48.9 | 61.5 | 71.6 | 85.1 | 97.9 |
| 0.025 | 2.5 | 0.9 | 2.8 | −0.1 | 13.8 | 19.7 | 31.4 | 47.3 | 68.7 | 93.4 |
| 0.008 | 2.8 | −0.1 | 1.8 | −6.5 | −0.7 | 6.1 | 18.2 | 37.7 | 61.0 | 90.2 |
| 0.003 | −0.4 | −2.3 | 2.4 | −3.6 | −1.5 | 7.6 | 14.1 | 35.8 | 56.4 | 87.8 |
| 0.000 | 0.0 | −2.1 | −7.6 | 0.0 | 1.9 | 8.2 | 19.1 | 40.0 | 56.2 | 88.4 |

TABLE 4

HCC1806 Percent Inhibition Results (n = 5) 1$^{st}$ Replicate

| Compound | SN-38 (μM) | | | | | | | | | |
|---|---|---|---|---|---|---|---|---|---|---|
| A (μM) | 0.0000 | 0.00002 | 0.0001 | 0.0002 | 0.0005 | 0.0014 | 0.0041 | 0.0123 | 0.0370 | 0.1110 |
| 6.000 | 17.4 | 16.3 | 18.1 | 19.9 | 32.5 | 78.1 | 84.4 | 87.3 | 92.7 | 96.5 |
| 2.000 | 9.7 | 9.3 | 8.1 | 12.5 | 19.7 | 64.6 | 80.7 | 83.4 | 89.8 | 95.4 |
| 0.667 | 3.5 | 3.9 | 4.4 | 8.8 | 15.7 | 53.7 | 77.1 | 80.9 | 88.4 | 94.9 |
| 0.222 | 3.2 | 3.1 | 3.0 | 5.9 | 10.4 | 46.9 | 72.3 | 78.3 | 87.4 | 94.5 |
| 0.074 | −2.0 | −0.4 | 2.1 | −1.5 | 9.5 | 36.6 | 66.7 | 75.7 | 86.8 | 93.7 |
| 0.025 | 2.6 | 1.0 | 1.3 | −0.4 | 2.9 | 32.3 | 57.6 | 71.1 | 84.1 | 93.2 |
| 0.008 | −1.3 | 1.5 | 3.5 | 3.3 | 2.9 | 28.3 | 55.1 | 68.3 | 83.6 | 91.9 |
| 0.000 | 0.0 | −0.4 | 3.8 | 2.2 | 7.5 | 29.6 | 54.5 | 66.6 | 82.0 | 91.2 |

TABLE 5

HCC1806 Percent Inhibition Results (n = 5) 2$^{nd}$ Replicate

| Compound | SN-38 (μM) | | | | | | | | | |
|---|---|---|---|---|---|---|---|---|---|---|
| A (μM) | 0.0000 | 0.00002 | 0.0001 | 0.0002 | 0.0005 | 0.0014 | 0.0041 | 0.0123 | 0.0370 | 0.1110 |
| 6.000 | 15.5 | 14.2 | 19.0 | 21.1 | 32.6 | 69.8 | 85.3 | 87.4 | 92.6 | 96.8 |
| 2.000 | 3.2 | 5.0 | 10.6 | 8.8 | 18.9 | 55.6 | 81.4 | 83.8 | 90.4 | 95.4 |
| 0.667 | 6.9 | 2.2 | 9.6 | 7.9 | 13.3 | 43.4 | 76.2 | 80.8 | 88.4 | 94.9 |
| 0.222 | 2.0 | 0.9 | 4.1 | 1.9 | 7.7 | 35.6 | 68.3 | 77.9 | 87.3 | 94.6 |
| 0.074 | 5.4 | −1.0 | −2.6 | 5.8 | 11.4 | 28.9 | 61.1 | 71.6 | 86.1 | 92.9 |
| 0.025 | 0.2 | −2.3 | 3.3 | 2.8 | 3.6 | 25.2 | 55.7 | 65.8 | 82.1 | 91.9 |
| 0.008 | −2.0 | −2.2 | −3.2 | 0.5 | 4.1 | 25.9 | 53.2 | 63.7 | 80.1 | 90.9 |
| 0.000 | 0.0 | −0.9 | 6.0 | 1.2 | 8.2 | 26.9 | 48.7 | 61.5 | 79.8 | 90.3 |

TABLE 6

HCC1187 Percent Inhibition Results (n = 5) 1st Replicate

| Compound | SN-38 (µM) | | | | | | | | | |
|---|---|---|---|---|---|---|---|---|---|---|
| A (µM) | 0.0000 | 0.0002 | 0.0005 | 0.0014 | 0.0041 | 0.0123 | 0.0370 | 0.1111 | 0.3333 | 1.0000 |
| 2.000 | 99.2 | 99.3 | 99.4 | 99.2 | 99.2 | 99.3 | 99.4 | 99.5 | 99.5 | 99.9 |
| 0.667 | 99.2 | 99.2 | 99.2 | 99.3 | 99.1 | 99.7 | 99.5 | 99.8 | 99.9 | 99.8 |
| 0.222 | 97.0 | 98.1 | 98.2 | 98.3 | 98.5 | 99.0 | 99.3 | 99.5 | 99.6 | 99.5 |
| 0.074 | 67.1 | 76.1 | 81.1 | 85.7 | 89.0 | 90.6 | 96.6 | 97.9 | 99.1 | 99.3 |
| 0.025 | 4.2 | 13.3 | 24.1 | 37.2 | 54.3 | 64.0 | 78.9 | 87.1 | 92.8 | 96.2 |
| 0.008 | 0.0 | −3.6 | −0.1 | 8.0 | 13.5 | 25.3 | 56.8 | 73.1 | 79.9 | 88.3 |
| 0.003 | −1.7 | −0.5 | −1.3 | −1.4 | 7.6 | 12.2 | 36.6 | 58.2 | 71.1 | 82.2 |
| 0.000 | 0.0 | 1.9 | −0.3 | 0.0 | 1.5 | 12.3 | 36.7 | 56.0 | 71.0 | 82.6 |

TABLE 7

HCC1187 Percent Inhibition Results (n = 5) 2nd Replicate

| Compound | SN-38 (µM) | | | | | | | | | |
|---|---|---|---|---|---|---|---|---|---|---|
| A (µM) | 0.0000 | 0.0002 | 0.0005 | 0.0014 | 0.0041 | 0.0123 | 0.0370 | 0.1111 | 0.3333 | 1.0000 |
| 2.000 | 97.9 | 98.1 | 98.6 | 98.1 | 98.2 | 98.4 | 98.9 | 98.9 | 99.1 | 99.5 |
| 0.667 | 97.8 | 98.1 | 98.2 | 97.9 | 98.1 | 98.3 | 98.8 | 99.3 | 99.5 | 99.4 |
| 0.222 | 94.7 | 95.7 | 96.4 | 96.9 | 97.2 | 97.6 | 99.0 | 99.3 | 99.4 | 99.4 |
| 0.074 | 56.2 | 66.7 | 78.8 | 81.4 | 86.2 | 90.5 | 95.9 | 97.8 | 98.8 | 99.3 |
| 0.025 | 9.5 | 18.0 | 33.2 | 45.0 | 56.7 | 66.5 | 78.7 | 87.5 | 93.8 | 96.8 |
| 0.008 | −0.4 | 0.8 | 10.0 | 18.4 | 23.2 | 32.2 | 52.2 | 69.4 | 81.3 | 89.1 |
| 0.003 | −1.0 | −5.2 | 3.1 | 10.7 | 13.8 | 16.9 | 34.2 | 56.4 | 73.8 | 84.3 |
| 0.000 | 0.0 | 1.1 | 2.6 | 8.1 | 10.9 | 18.1 | 36.2 | 55.9 | 72.8 | 86.0 |

TABLE 8

HCC1187 Percent Inhibition Results (n = 5) 3rd Replicate

| Compound | SN-38 (µM) | | | | | | | | | |
|---|---|---|---|---|---|---|---|---|---|---|
| A (µM) | 0.0000 | 0.0002 | 0.0005 | 0.0014 | 0.0041 | 0.0123 | 0.0370 | 0.1111 | 0.3333 | 1.0000 |
| 2.000 | 99.6 | 99.4 | 99.6 | 99.3 | 99.5 | 99.3 | 100.1 | 100.1 | 100.0 | 100.1 |
| 0.667 | 99.4 | 99.2 | 99.3 | 99.3 | 99.5 | 99.6 | 99.8 | 99.8 | 99.7 | 100.1 |
| 0.222 | 98.2 | 98.7 | 98.6 | 98.2 | 99.1 | 99.5 | 99.9 | 99.9 | 99.4 | 100.0 |
| 0.074 | 81.4 | 85.1 | 87.7 | 87.6 | 92.7 | 95.0 | 97.2 | 97.9 | 98.8 | 99.4 |
| 0.025 | 38.4 | 41.8 | 53.9 | 55.0 | 63.9 | 73.4 | 81.3 | 87.2 | 91.3 | 94.8 |
| 0.008 | 6.0 | 15.6 | 24.4 | 22.8 | 32.0 | 41.8 | 57.0 | 68.1 | 76.0 | 85.5 |
| 0.003 | −1.0 | 10.1 | 17.7 | 6.9 | 10.7 | 16.8 | 36.1 | 50.0 | 63.1 | 76.6 |
| 0.000 | 0.0 | 10.2 | 11.6 | 10.1 | 10.1 | 17.9 | 32.7 | 43.5 | 60.8 | 75.5 |

TABLE 9

H522 Percent Inhibition Results (n = 5) 1st Replicate

| Compound | SN-38 (µM) | | | | | | | | | |
|---|---|---|---|---|---|---|---|---|---|---|
| A (µM) | 0.0000 | 0.0002 | 0.0005 | 0.0014 | 0.0041 | 0.0123 | 0.0370 | 0.1111 | 0.3333 | 1.0000 |
| 2.000 | 81.2 | 81.9 | 85.2 | 92.1 | 97.0 | 99.9 | 100.7 | 101.1 | 101.6 | 101.4 |
| 0.667 | 65.5 | 67.3 | 71.0 | 79.0 | 93.4 | 99.0 | 100.4 | 101.3 | 101.2 | 101.3 |
| 0.222 | 38.9 | 34.8 | 42.5 | 52.8 | 74.1 | 87.4 | 96.5 | 99.8 | 101.0 | 100.9 |
| 0.074 | 13.0 | 13.0 | 17.1 | 30.6 | 45.3 | 62.0 | 75.8 | 84.7 | 95.4 | 100.0 |
| 0.025 | 3.5 | 4.7 | 7.3 | 16.8 | 22.2 | 35.6 | 50.9 | 57.2 | 71.1 | 90.6 |
| 0.008 | 1.3 | −0.3 | 4.5 | 10.5 | 17.8 | 24.0 | 40.7 | 47.0 | 59.3 | 80.0 |
| 0.003 | −4.1 | 0.1 | 3.3 | 11.7 | 6.7 | 21.9 | 36.9 | 44.3 | 51.9 | 75.1 |
| 0.000 | 0.0 | 1.8 | 0.9 | 6.7 | 11.5 | 23.0 | 29.6 | 46.3 | 52.7 | 74.4 |

TABLE 10

H522 Percent Inhibition Results (n = 5) $2^{nd}$ Replicate

| Compound A (μM) | SN-38 (μM) | | | | | | | | | |
|---|---|---|---|---|---|---|---|---|---|---|
| | 0.0000 | 0.0002 | 0.0005 | 0.0014 | 0.0041 | 0.0123 | 0.0370 | 0.1111 | 0.3333 | 1.0000 |
| 2.000 | 77.2 | 78.6 | 83.3 | 90.5 | 96.3 | 98.8 | 100.2 | 99.9 | 100.1 | 100.3 |
| 0.667 | 62.5 | 65.0 | 68.5 | 79.9 | 93.5 | 97.6 | 99.5 | 100.3 | 100.3 | 100.2 |
| 0.222 | 28.3 | 34.7 | 38.4 | 53.1 | 78.5 | 91.2 | 96.6 | 99.9 | 100.4 | 100.4 |
| 0.074 | 14.7 | 6.7 | 11.8 | 25.5 | 43.4 | 63.6 | 75.9 | 86.3 | 96.6 | 99.7 |
| 0.025 | 4.4 | 6.7 | 8.3 | 12.9 | 22.0 | 34.7 | 50.1 | 57.7 | 73.2 | 91.4 |
| 0.008 | 4.0 | −0.4 | 2.3 | 10.2 | 13.0 | 24.7 | 39.2 | 46.2 | 58.0 | 78.5 |
| 0.003 | 2.2 | −0.3 | −1.7 | 6.1 | 12.7 | 24.4 | 33.7 | 44.5 | 50.9 | 71.8 |
| 0.000 | 0.0 | 5.2 | −1.9 | 9.6 | 13.5 | 21.2 | 31.6 | 43.6 | 51.2 | 70.0 |

TABLE 11

H820 Percent Inhibition Results (n = 5) $1^{st}$ Replicate

| Compound A (μM) | SN-38 (μM) | | | | | | | | | |
|---|---|---|---|---|---|---|---|---|---|---|
| | 0.0000 | 0.00002 | 0.0001 | 0.0002 | 0.0005 | 0.0014 | 0.0041 | 0.0123 | 0.0370 | 0.1110 |
| 6.000 | 75.6 | 72.1 | 70.8 | 71.9 | 74.9 | 77.7 | 76.8 | 87.0 | 96.3 | 100.0 |
| 2.000 | 46.7 | 45.3 | 45.5 | 46.4 | 46.6 | 52.8 | 60.5 | 73.5 | 91.1 | 98.3 |
| 0.667 | 38.9 | 36.9 | 36.9 | 37.1 | 42.0 | 44.1 | 55.3 | 64.9 | 87.5 | 97.5 |
| 0.222 | 35.0 | 31.0 | 35.0 | 29.7 | 33.2 | 38.1 | 46.0 | 56.9 | 82.3 | 96.8 |
| 0.074 | 16.8 | 17.2 | 15.8 | 19.2 | 23.4 | 23.1 | 34.4 | 47.9 | 78.2 | 94.7 |
| 0.025 | 3.6 | 11.2 | 4.5 | 2.1 | 11.9 | 11.4 | 20.0 | 36.6 | 68.3 | 88.5 |
| 0.008 | 3.0 | −1.5 | −1.0 | 8.0 | 5.1 | 6.3 | 9.2 | 27.2 | 60.7 | 84.3 |
| 0.000 | 0.0 | 1.9 | −2.2 | −2.9 | 0.2 | 2.3 | 3.3 | 23.2 | 51.1 | 78.5 |

TABLE 12

H820 Percent Inhibition Results (n = 5) $2^{nd}$ Replicate

| Compound A (μM) | SN-38 (μM) | | | | | | | | | |
|---|---|---|---|---|---|---|---|---|---|---|
| | 0.0000 | 0.0002 | 0.0005 | 0.0014 | 0.0041 | 0.0123 | 0.0370 | 0.1111 | 0.3333 * | 1.0000 * |
| 6.000 | 68.5 | 66.7 | 69.3 | 75.2 | 76.6 | 91.5 | 98.0 | 100.5 | 100.9 | 101.0 |
| 2.000 | 40.3 | 36.9 | 37.1 | 47.0 | 58.8 | 77.8 | 94.6 | 99.9 | 100.9 | 101.2 |
| 0.667 | 27.4 | 33.0 | 31.5 | 39.8 | 52.5 | 71.4 | 92.1 | 99.1 | 100.5 | 101.3 |
| 0.222 | 28.8 | 32.1 | 31.3 | 30.4 | 46.8 | 68.9 | 89.8 | 98.9 | 100.6 | 101.0 |
| 0.074 | 22.5 | 21.9 | 22.4 | 24.0 | 39.8 | 57.7 | 85.7 | 96.8 | 99.9 | 101.1 |
| 0.025 | 10.7 | 10.5 | 9.4 | 13.5 | 22.4 | 45.6 | 78.5 | 92.8 | 98.2 | 100.6 |
| 0.008 | 4.7 | −1.9 | 2.3 | 6.3 | 19.2 | 37.0 | 67.3 | 87.5 | 95.6 | 99.6 |
| 0.000 | 0.0 | −3.9 | 0.2 | 6.9 | 17.7 | 31.4 | 64.1 | 82.6 | 92.0 | 98.3 |

* SN-38 dose response shifted to 1.0 μM top concentration to capture a great potential range of synergistic activity

Example 2: MCL-1 Inhibitor In Vitro Synergy with Paclitaxel in TNBC Cells

Materials and Methods
Cell Culture and Reagents

HCC70 (ATCC® CRL-2315) and HCC1806 (ATCC® CRL-2335) were thawed from liquid nitrogen storage and maintained according to ATCC guidelines in RPMI-1640 (Gibco-12633)+10% HI-FBI (Gibco-16140)+Pen/Strep (100× Gibco-15140). MDA-MB-468 (ATCC® HTB-132) was thawed and maintained in DMEM (Gibco-11995)+10% HI-FBS+Pen/Strep. Cells were passaged according to ATCC guidelines with 0.25% Trypsin/EDTA (1× GIBCO-25200).

Paclitaxel and compound A stocks (provided by Gilead sample bank) were dispensed directly into treatment wells using D300e Digital Dispenser (vendor) with DMSO (Sigma-D2438) as vehicle control to 0.1% v/v.

Viability assessments were performed using Cell Titer Glo™ (Promega #G9241) according to manufactures microwell plate protocol and read for luminescence on Synergy Neo2 plate reader.

Cell lysates for MSD assays were generated using 1× Lysis Buffer (10× cell signaling CST-9803) 100× Protease Inhibitor, Phosphatase Inhibitor I, Phosphatase Inhibitor II (Meso Scale Discovery Inhibitor Pack R70AA-1, and PMSF (SIGMA cat #7626)

MCL-BAK and MCL1-BIM dimer assays and total MCL1 assay were developed by MSD Custom Assay Services and run using the MSD U-PLEX Development Pack (K15227N) and protocols' revision "2018Mar rev 2". GAPDH was determined by MSD using standard assay K151PWD. All plates were read on MSD SECTOR Imager 2400 using MSD Read Buffer T (R92TC).

Protein Simple reagents: EZ Standard Pack1 (PS-ST01EZ: Biotinylated ladder, FL standard and DTT), Peroxide (044-379), Luminal-S (043-311), Antibody Dilution Buffer (042-203), Streptavidin HRP (042-414), secondary antibodies: goat-anti-rabbit (042-206) and goat anti-mouse (042-205), Separation Matrix (042-512), Stacking Matrix (042-513), 10× Sample Buffer (042-195), Wash Buffer (042-520), Upper Running Buffer (043-163), Lower Running Buffer (043-162), 384-well plate (040-663), Size Capillaries (55700), Protein Simple Instruments Peggy Sue™ and Sally Sue™. Primary antibodies: MCL1 (CST-94296), FBXW7 (Abcam 109617 and Abcam 171961)

Cell Viability Combination Assays

For synergy matrix assays, TNBC cell lines were seeded 10,000 cells per well in clear-bottomed white 96-well plates (Corning #3909) in 100 µL of recommended cell culture medium. Plates were incubated at 37° C. and 100% RH for 20 hours prior to compound exposure. Treatment map consisted of single agent dose responses for compound A (seven 3-fold dilutions from 3 µM to 4 nM plus no treatment control) or paclitaxel (nine 3-fold dilutions from 3 µM to 0.5 nM plus no treatment control) and a checkerboard matrix of 63 distinct combinations. Five plates were used for each combination to generate enough replicates to calculate synergy scores with a 95% confidence interval (95% CI).

Paclitaxel and DMSO vehicle were first applied to cells using an HP D300 dispenser to aliquot directly into media according to checkerboard matrix. Paclitaxel was incubated for 4 hours then washed off by media removal and 2×200 µL washes with prewarmed complete media and final replacement with 100 µL prewarmed complete media. Cells were then exposed to compound A with the same checkerboard matrix using D300 dispenser and incubated for 48 hours prior to measurement of viability by Cell Titer Glo.

MSD Assays

For MSD assays, TNBC cell lines were seeded 25,000 cells per well in clear-bottomed white 96-well plates (Corning #3909) in recommended cell culture medium. Plates were incubated at 37° C. and 100% RH for 20 hours prior to compound exposure. Paclitaxel and DMSO vehicle were first applied to cells using an HP D300 dispenser to aliquot directly into media. Paclitaxel was incubated for 4 hours then washed off by media removal and 2×150 µL washes with prewarmed complete media and final replacement with 100 µL prewarmed complete media. After an additional 20 hours, samples were harvested by aspirating away supernatant and 125 µl of 1× lysis buffer was added to each well. Plates were set on ice briefly and transferred to a rocking platform at 4° C. for 20 minutes. Plates were placed on dry ice, snap frozen for 10 minutes then stored at −80° C. until tested.

MCL1 and MCL1-BAK and MCL1-BIM dimer assays were run using materials and protocols provided by MSD Custom Assay Services based on their U-Plex technology. Plates were first prepared using standard U-PLEX capture antibody coating protocol and then washed 3× with 150 uL MSD wash buffer. 25 µl of samples or standards were added directly to the plates, plates sealed and incubated with shaking at room temperature for 1 hour. Plates were washed 3× with 150 µl wash buffer per well and 50 µl of antibody detection solution was added to each well of the MSD plates, plates sealed and incubated with shaking at room temperature for 1 hours. Plates were again washed 3× with 150 µl wash buffer per well. 150 µl of 2× read buffer was added to each well and plates were read on an MSD SECTOR Imager 2400.

GAPDH assay kit (MSD) was run according to manufacturer protocols using 25 µL of lysate per sample added directly to the plates. Plates were sealed, incubated with shaking at room temperature for 1 hour and then washed 3× with 150 µl wash buffer per well. 25 µl of antibody detection solution was added to each well, plates were sealed, incubated with shaking at room temperature for 1 hour and then washed 3× with 150 µl wash buffer per well. 150 µl of 2× read buffer was then added to each well and plates were measured on an MSD SECTOR Imager 2400 for electrochemiluminescence (ECL).

Protein Simple (Simple Western)

Simple Western immunoassays take place in a capillary. Samples and reagents are loaded into an assay plate and placed in a Protein Simple Instrument. Cell lysates are loaded into the capillary automatically and separated by size as they migrate through a stacking and separation matrix. The separated proteins are then immobilized to the capillary wall via a proprietary, photoactivated capture chemistry. Target proteins are identified using a primary antibody and immunoprobed using an HRP-conjugated secondary antibody and chemiluminescent substrate. The resulting chemiluminescent signal is detected and quantitated.

FBXW7 expression was measured in cells lines after a 4 hour dose of 1 µM paclitaxel followed by washout and overnight incubation using Simple Western. Lysates were prepared, diluted to 0.5 ug/ml in 1× lysis buffer. Simple Western platform is run on a 384-well plate.

Markers, internal ladders and DTT are provided by Simple Western in lyophilized forms. Reagents are resuspended as protocol describes. 20 uL of water is added to the markers. 40 ul of water is added to DTT, 20 ul of 10× sample buffer and 20 ul of DTT is mixed and called Z buffer. Markers are loaded in 1A. 5 ul of lysate was added to 1.7 ml Eppendorf tube. 1.2 ul of Z reagent was added to each sample. The samples were heated at 100 C for 5 minutes, allowed to cool than spun in a microfuge for 30 seconds. Samples are loaded in wells A2-12. Primary antibodies were diluted 1:50 in Antibody dilution buffer (6 ul+294 ul dilution buffer). 20 ul of each antibody was loaded in lanes 2-12. A different antibody for each row up to 8 antibodies. Actin diluted 1:300 was used as a loading control. Additionally, secondary antibodies either goat-anti-rabbit or goat-anti-mouse are loaded as needed. The plate is spun 2.6 k 10 minutes RT and loaded into the instrument and allowed to run overnight. Target proteins are identified using a primary antibody and immunoprobed using an HRP-conjugated secondary antibody and chemiluminescent substrate. The resulting chemiluminescent signal is detected and quantitated.

Data Analysis

For Bliss Synergy

Combination viability data was evaluated for synergy using an excel template described by Prichard and Shipman {Prichard 1990}. Specifically, single component dose curves of paclitaxel and compound A were normalized to percent viability on each plate and averaged across 5 technical replicates to calculate theoretical additive killing of combinations according to the principle of Bliss Independence. Calculated values were compared to experimental results generated in the sixty-three-concentration checkerboard. Synergy or antagonism scores were generated depending on whether the observed growth inhibition was greater than or less than the calculated values, respectively.

For example, if two compounds (B) and (C) at given concentrations each resulted in 60% inhibition, their theoretical additive inhibition would be 84% according the following Bliss Independence formula:

$$60\%_B + 60\%_C * (100\% - 60\%_B) = 84\%_{B+C}$$

If the experimental result was greater than calculated (e.g. 90% inhibition) then the difference [6%] would be added to the synergy score. If the result was less (e.g. 78% inhibition) then the difference [6%] would be added to the antagonism score.

These differences were summed up across the whole checker-board (sixty-three wells) to give cumulative synergy and antagonism scores with units of $\mu M^2\%$ to reflect the 2D surface of the dose responses. A 95% confidence interval adjustment was applied to the synergy and antagonism scores and each sum was compared to a scale based on the original method: scores greater than 50 were considered moderate synergy and scores greater than 100 were considered strong synergy and likely to show combination effect in vivo {Prichard 1990}.

Data for combination assays is presented in three formats. Synergy score @ 95% confidence interval averaged from n=2 assays. Example tabulated and graphical percent inhibition matrix for each cell line. Example tabulated and graphical synergy matrix @ 95% confidence interval for each cell line.

MSD Assays

For total MCL1, ECL signal was recorded and converted to pg/mL as determined via 8 point standard dose range (0-10,000 pg/mL) with MSD developed calibration controls and using 4 parameter curve fit function in MSD WorkBench software. MCL1-BAK and MCL1-BIM dimer results were converted to pg/mL using the same process but with standard concentrations ranging from 0-50,000 pg/mL. GAPDH results were recorded and reported as ECL and used to normalize both MCL1 and the MCL1 dimers within each sample set. For graphical comparison between analytes for a given cell line, each pg/mL data set was normalized to vehicle control at 100% and no protein as 0%.

Paclitaxel has been reported to downregulate MCL1 protein levels, in part through elevation of the MCL1 E3-ligase FBXW7, which targets MCL1 for proteasomal degradation {Wertz 2011}. To confirm this observation HCC70, MDA-MB-468, and HCC1806 TNBC cell lines were treated with a clinically relevant concentration of paclitaxel (1 μM) for 4 hours {Gianni 1995}. Following paclitaxel treatment, cells were incubated overnight and protein levels were determined. Comparison of paclitaxel treatment to vehicle control revealed elevated FBXW7 protein levels and reduced MCL1 protein levels (Table 13 and FIG. 1). Paclitaxel treatment also lead to reduced protein levels of MCL1-BAK and MCL1-BIM dimers (Table 13 and FIG. 1). These results were observed across all three TNBC cell lines (n=3 biological replicates).

HCC70, MDA-MB-468, and HCC1806 TNBC cell lines were treated with a clinically relevant concentration of paclitaxel (1 μM) for 4 hours {Gianni 1995}. Paclitaxel treatment elevated FBXW7 protein levels, reduced MCL1 protein levels, and reduced protein levels of MCL1-BAK and MCL1-BIM dimers in all three cell lines. Bliss synergy (>100) was observed when HCC70, MDA-MB-468 and HCC1806 were pretreated with paclitaxel dose titration (including a protein adjusted $C_{max}=1$ μM) for 4 hours to mimic clinical exposure and then exposed to a dose titration of compound A for 72 hours.

TABLE 13

Percent (%) Change Relative to Vehicle Following Paclitaxel Treatment

| Cell line | FBXW7[a] | MCL1[a] | MCL1-BAK Dimer[a] | MCL1-BIM Dimer[a] |
|---|---|---|---|---|
| HCC70 | 269 ± 59 | 45 ± 2.6 | 59 ± 8.7 | 63 ± 10.1 |
| HCC1806 | 172 ± 27 | 48 ± 4.9 | 83 ± 11 | 79 ± 3.0 |
| MDA-MB-468 | 240 ± 11 | 70 ± 4.8 | 92 ± 0.5 | 86 ± 0.5 |

[a]Averaged normalized protein levels (n = 3 biological replicates)

Figure 2:
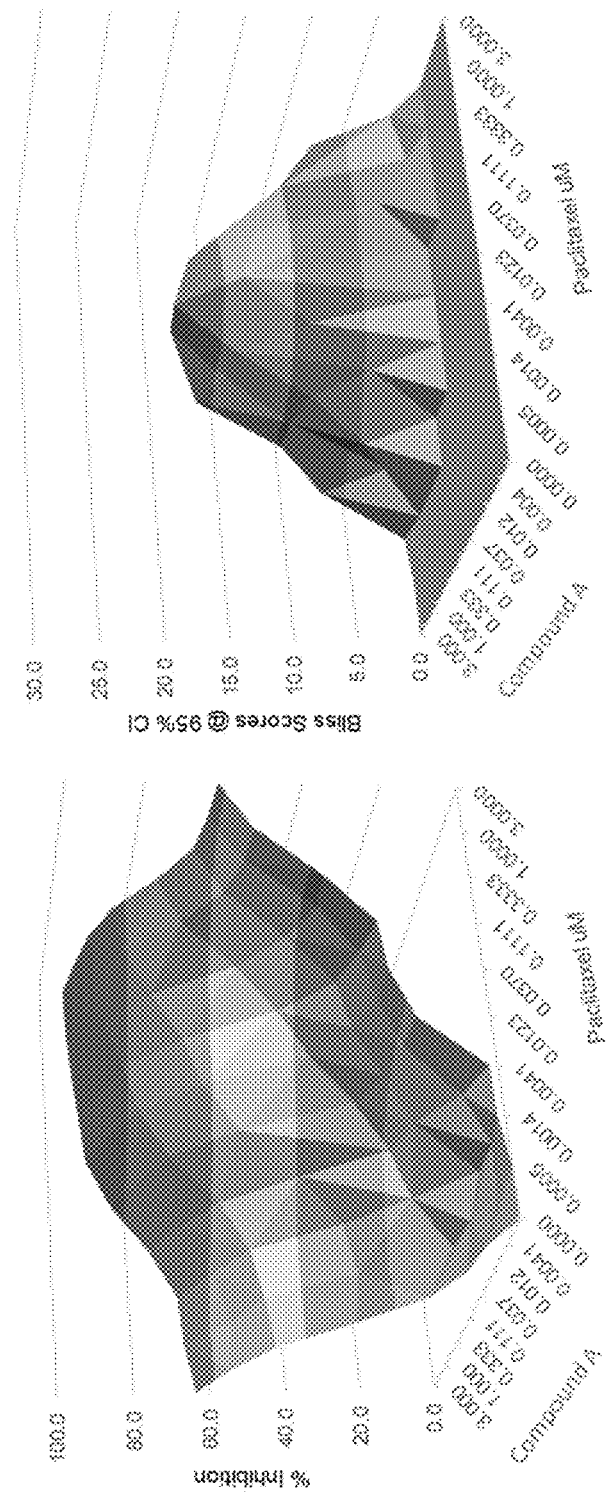
FIG. 2 HCC70 Inhibition and 95% CI Synergy Response Surfaces.
Figure 3:
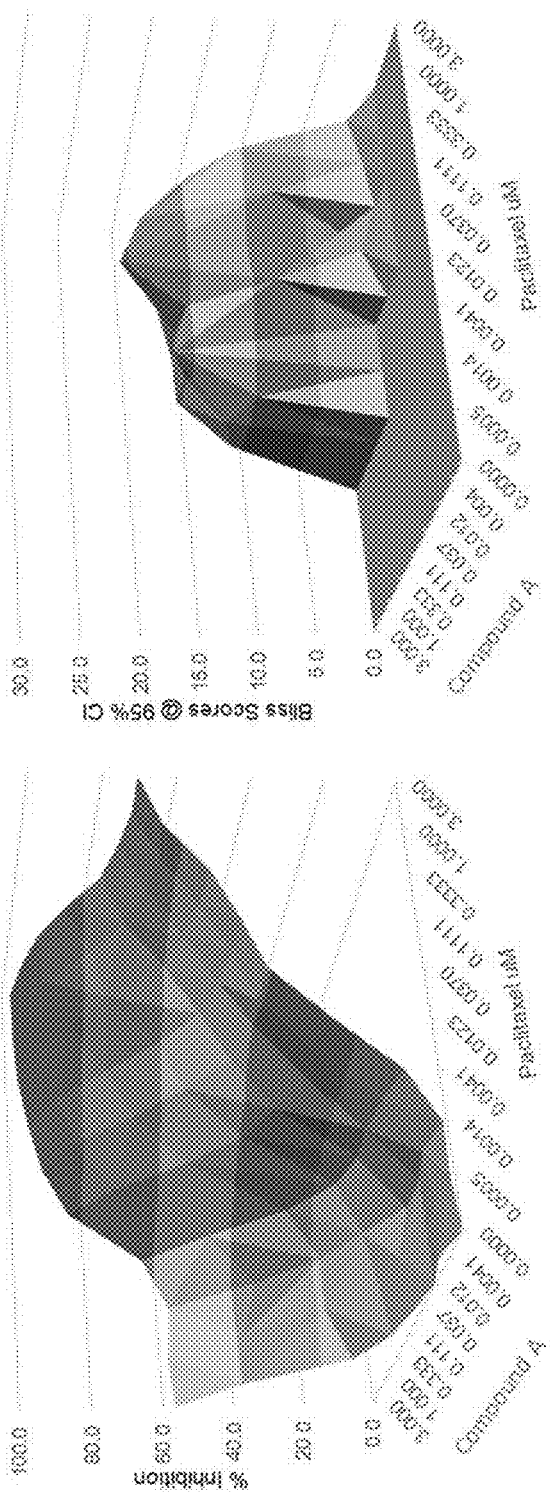
FIG. 3 MDA-MB-468 Inhibition and 95% CI Synergy Response Surfaces.
Figure 4:
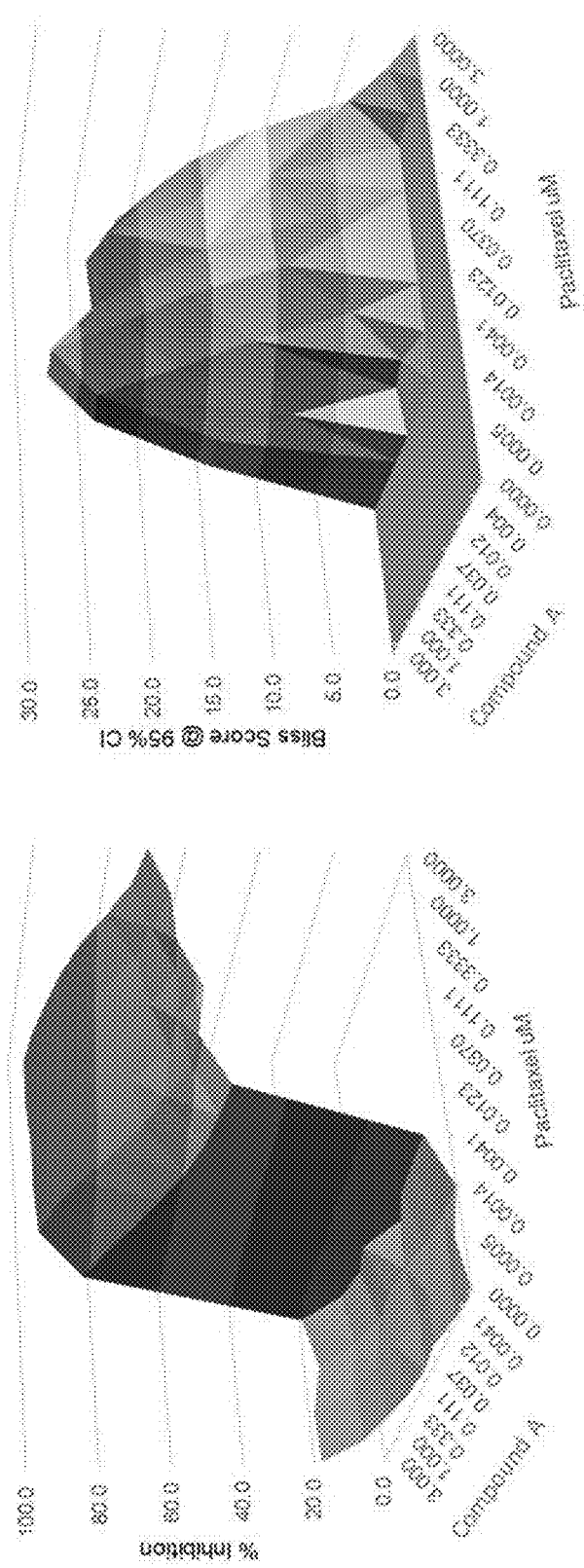
FIG. 4 HCC1806 Inhibition and 95% CI Synergy Response Surfaces.

To determine if reduced MCL1 protein levels following paclitaxel treatment resulted in enhanced sensitivity to compound A Bliss synergy was used. HCC70, MDA-MB-468 and HCC1806 were pretreated with a paclitaxel dose titration (including a protein adjusted $C_{max}=1$ μM) for 4 hours to mimic clinical exposure and then exposed to a dose titration of compound A. Cells were incubated for 72 hours and viability was determined using CTG reagent. Bliss synergy was observed across all three TNBC cell lines exposed to a combination of compound A and paclitaxel in vitro (Table 15, and FIGS. 2-4). Bliss synergy scores greater than 100 are considered strong synergy {Prichard 1990}.

TABLE 14

Compound A + paclitaxel Bliss Synergy Scores @ 95% Confidence Interval

| Cell Line | 95% Bliss Synergy Score (n = 2) |
|---|---|
| HCC70 | 330 |
| MDA-MB-468 | 300 |
| HCC1806 | 440 |

TABLE 15

HCC70 Percent Inhibition Results (n = 5)

| | | Paclitaxel (μM) | | | | | | | | |
|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |
| Compound A (μM) | 3.000 | 63.7 | 66.0 | 66.9 | 73.8 | 83.5 | 89.5 | 90.8 | 92.2 | 93.2 | 93.4 |
| | 1.000 | 56.6 | 55.3 | 59.1 | 67.1 | 76.7 | 84.3 | 87.0 | 88.9 | 90.2 | 91.3 |
| | 0.333 | 46.7 | 48.5 | 51.2 | 58.1 | 70.4 | 77.6 | 81.2 | 85.7 | 86.5 | 88.6 |
| | 0.111 | 28.5 | 26.7 | 29.3 | 39.2 | 53.6 | 62.2 | 66.6 | 74.2 | 81.1 | 83.1 |
| | 0.037 | 12.9 | 5.3 | 14.2 | 18.4 | 26.0 | 36.2 | 43.6 | 53.4 | 67.0 | 72.5 |
| | 0.012 | 6.5 | 3.9 | −0.2 | 14.7 | 21.1 | 27.7 | 30.7 | 42.2 | 57.4 | 64.4 |
| | 0.004 | 4.9 | 0.4 | −0.2 | 5.7 | 18.9 | 23.8 | 27.0 | 36.4 | 53.8 | 62.3 |
| | 0.000 | 0.0 | −2.3 | 1.9 | 2.0 | 18.3 | 23.7 | 25.1 | 37.4 | 53.3 | 61.4 |

TABLE 16

HCC70 Synergy Results (95% CI)

| | | Paclitaxel (μM) | | | | | | | | | |
|---|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |
| Compound A (μM) | 3.000 | 0.0 | 0.0 | 0.3 | 6.6 | 9.5 | 16.1 | 16.2 | 13.3 | 9.3 | 6.0 |
| | 1.000 | 0.0 | 0.0 | 0.0 | 2.1 | 9.5 | 14.3 | 18.4 | 15.3 | 9.5 | 6.8 |
| | 0.333 | 0.0 | 0.0 | 0.0 | 4.7 | 8.6 | 14.1 | 18.6 | 17.2 | 9.2 | 6.6 |
| | 0.111 | 0.0 | 0.0 | 0.0 | 0.0 | 4.5 | 8.8 | 13.7 | 12.6 | 10.2 | 7.1 |
| | 0.037 | 0.0 | 0.0 | 0.0 | 0.0 | 0.0 | 0.0 | 0.0 | 3.3 | 0.7 | 1.7 |
| | 0.012 | 0.0 | 0.0 | 0.0 | 0.0 | 0.0 | 0.0 | 0.0 | 0.0 | 0.0 | 0.0 |
| | 0.004 | 0.0 | 0.0 | 0.0 | 0.0 | 0.0 | 0.0 | 0.0 | 0.0 | 0.0 | 0.0 |
| | 0.000 | 0.0 | 0.0 | 0.0 | 0.0 | 0.0 | 0.0 | 0.0 | 0.0 | 0.0 | 0.0 |

TABLE 17

MDA-MB-468 Percent Inhibition Results (n = 5)

| | | Paclitaxel (μM) | | | | | | | | | |
|---|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |
| Compound A (μM) | 3.000 | 56.7 | 57.7 | 56.4 | 63.1 | 83.6 | 90.7 | 94.0 | 96.5 | 97.4 | 97.5 |
| | 1.000 | 39.6 | 38.1 | 34.0 | 46.0 | 71.4 | 82.2 | 86.6 | 92.2 | 94.6 | 95.3 |
| | 0.333 | 12.1 | 18.2 | 18.0 | 25.9 | 52.8 | 67.0 | 73.8 | 83.3 | 90.6 | 91.7 |
| | 0.111 | 4.4 | 6.3 | 9.0 | 14.9 | 39.2 | 54.5 | 60.7 | 74.5 | 77.7 | 84.7 |
| | 0.037 | 2.0 | 3.7 | 0.0 | 11.7 | 33.0 | 43.6 | 51.0 | 60.1 | 70.4 | 76.0 |
| | 0.012 | −0.6 | −1.6 | 0.0 | 12.6 | 26.4 | 38.4 | 48.1 | 56.6 | 65.6 | 72.6 |
| | 0.004 | 2.5 | 1.3 | 3.0 | 11.6 | 28.1 | 41.2 | 46.7 | 54.2 | 64.0 | 70.4 |
| | 0.000 | 0.0 | 1.1 | 0.9 | 8.7 | 25.6 | 41.0 | 46.6 | 53.4 | 65.1 | 70.5 |

TABLE 18

MDA-MB-468 Synergy Results (95% CI)

| | | Paclitaxel (μM) | | | | | | | | | |
|---|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |
| Compound A (μM) | 3.000 | 0.0 | 0.0 | 0.0 | 0.0 | 10.8 | 15.3 | 15.4 | 13.8 | 11.3 | 8.8 |
| | 1.000 | 0.0 | 0.0 | 0.0 | 0.0 | 11.9 | 15.2 | 15.7 | 17.6 | 13.5 | 12.3 |
| | 0.333 | 0.0 | 0.0 | 0.0 | 0.0 | 9.8 | 16.7 | 15.3 | 20.8 | 18.7 | 14.3 |
| | 0.111 | 0.0 | 0.0 | 0.0 | 0.0 | 0.0 | 0.0 | 8.2 | 1.7 | 7.6 | 10.5 |
| | 0.037 | 0.0 | 0.0 | 0.0 | 0.0 | 0.0 | 0.0 | 1.7 | 0.0 | 0.6 | 1.4 |
| | 0.012 | 0.0 | 0.0 | 0.0 | 0.0 | 0.0 | 0.0 | 0.0 | 0.0 | 0.0 | 0.0 |
| | 0.004 | 0.0 | 0.0 | 0.0 | 0.0 | 0.0 | 0.0 | 0.0 | 0.0 | 0.0 | 0.0 |
| | 0.000 | 0.0 | 0.0 | 0.0 | 0.0 | 0.0 | 0.0 | 0.0 | 0.0 | 0.0 | 0.0 |

TABLE 19

HCC1806 Percent Inhibition Results (n = 5)

| | | Paclitaxel (μM) | | | | | | | | | |
|---|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |
| Compound A (μM) | 3.000 | 17.9 | 18.5 | 15.7 | 19.2 | 81.4 | 93.4 | 94.4 | 94.5 | 95.5 | 95.4 |
| | 1.000 | 8.6 | 9.8 | 8.0 | 10.4 | 76.2 | 90.1 | 90.9 | 91.7 | 92.7 | 94.1 |
| | 0.333 | 5.3 | 6.7 | 4.0 | 8.1 | 70.2 | 83.9 | 86.9 | 87.6 | 90.1 | 91.4 |
| | 0.111 | 2.9 | 5.0 | 4.9 | 10.0 | 64.7 | 76.5 | 79.5 | 81.8 | 84.9 | 88.5 |
| | 0.037 | 1.8 | 1.2 | 3.4 | 2.9 | 59.5 | 69.8 | 72.0 | 74.5 | 78.3 | 84.2 |
| | 0.012 | 2.8 | 2.3 | 1.2 | 5.8 | 56.3 | 65.8 | 63.4 | 68.0 | 70.7 | 78.0 |
| | 0.004 | 0.7 | −0.8 | −1.2 | 6.2 | 54.8 | 60.8 | 63.5 | 62.4 | 68.4 | 72.5 |
| | 0.000 | 0.0 | 2.3 | 0.0 | 6.5 | 53.4 | 60.9 | 58.4 | 64.4 | 64.8 | 69.9 |

TABLE 20

| | | Paclitaxel (μM) | | | | | | | | |
|---|---|---|---|---|---|---|---|---|---|---|
| | | 0.000 | 0.0005 | 0.0014 | 0.0041 | 0.012 | 0.037 | 0.111 | 0.333 | 1.000 | 3.000 |

HCC1806 Synergy Results (95% CI)

| | | 0.000 | 0.0005 | 0.0014 | 0.0041 | 0.012 | 0.037 | 0.111 | 0.333 | 1.000 | 3.000 |
|---|---|---|---|---|---|---|---|---|---|---|---|
| Compound A (μM) | 3.000 | 0.0 | 0.0 | 0.0 | 0.0 | 14.1 | 23.6 | 27.4 | 23.1 | 22.9 | 18.9 |
| | 1.000 | 0.0 | 0.0 | 0.0 | 0.0 | 13.7 | 23.7 | 27.4 | 23.4 | 24.0 | 21.0 |
| | 0.333 | 0.0 | 0.0 | 0.0 | 0.0 | 8.4 | 17.5 | 21.7 | 19.3 | 22.2 | 18.4 |
| | 0.111 | 0.0 | 0.0 | 0.0 | 0.0 | 0.4 | 11.9 | 16.8 | 15.2 | 15.9 | 15.7 |
| | 0.037 | 0.0 | 0.0 | 0.0 | 0.0 | 1.0 | 4.5 | 9.4 | 6.9 | 9.9 | 11.2 |
| | 0.012 | 0.0 | 0.0 | 0.0 | 0.0 | 0.0 | 0.0 | 0.0 | 0.0 | 0.0 | 3.7 |
| | 0.004 | 0.0 | 0.0 | 0.0 | 0.0 | 0.0 | 0.0 | 0.0 | 0.0 | 0.0 | 1.3 |
| | 0.000 | 0.0 | 0.0 | 0.0 | 0.0 | 0.0 | 0.0 | 0.0 | 0.0 | 0.0 | 0.0 |

Example 3

The combination potential of compound A with targeted agents and chemotherapies was tested in a panel of breast cancer cell lines using a 72-hour in vitro proliferation assays. Results of combination testing are shown in Table 21.

TABLE 21

In vitro combination testing results

| Cell Line | Compound A × | Synergy Score | Best CI | Best CI Level | Bliss Volume | HSA volume | Loewe Volume |
|---|---|---|---|---|---|---|---|
| AU565 | A-1331852 | 31.87 | 0.24 | 180 | 18.19 | 15.43 | 16.98 |
| AU565 | Abemaciclib | 5.97 | 0.18 | 30 | 6.65 | −0.73 | −0.71 |
| AU565 | ABT-199 | 3.85 | 0.29 | 65 | 3.93 | −3.00 | 3.57 |
| AU565 | ABT-263 | 14.69 | 0.61 | 160 | 9.56 | 3.63 | 8.42 |
| AU565 | BMN 673 | 8.12 | 0.72 | 180 | 5.62 | 2.94 | 1.49 |
| AU565 | Carboplatin | 3.68 | 1.10 | 40 | 6.93 | −0.68 | −0.04 |
| AU565 | Cisplatin | 1.66 | 0.79 | 35 | 7.67 | −6.49 | −5.19 |
| AU565 | Docetaxel | 7.58 | 0.33 | 180 | 16.97 | 3.68 | 1.71 |
| AU565 | Doxorubicin Hcl | 7.34 | 0.59 | 125 | 15.78 | 5.51 | 3.87 |
| AU565 | Everolimus | 3.02 | 0.59 | 25 | 5.68 | 2.64 | 3.01 |
| AU565 | Fulvestrant | 3.43 | 0.90 | 105 | 6.82 | 2.40 | 4.57 |
| AU565 | GDC-0068 | 6.93 | 0.88 | 180 | 5.42 | 2.46 | 1.85 |
| AU565 | Gemcitabine Hydrochloride | 9.40 | 0.56 | 180 | 10.13 | 3.57 | 2.71 |
| AU565 | Lapatinib Ditosylate | 17.32 | 0.44 | 180 | 19.54 | 9.10 | 7.34 |
| AU565 | LEE011 | 1.58 | 1.01 | 50 | −1.41 | −6.50 | −4.57 |
| AU565 | Neratinib | 19.43 | 0.40 | 180 | 18.09 | 11.74 | 10.72 |
| AU565 | Olaparib | 2.27 | 0.75 | 30 | 2.11 | −1.92 | 0.98 |
| AU565 | Paclitaxel | 5.68 | 0.19 | 180 | 18.11 | 2.33 | 0.40 |
| AU565 | PD-0332991 | 1.50 | 1.01 | 40 | −1.48 | −4.75 | −4.99 |
| AU565 | Tamoxifen Citrate | 4.68 | 0.63 | 30 | 8.31 | −0.90 | 1.23 |
| BT-20 | A-1331852 | 162.62 | 0.01 | 170 | 68.96 | 70.29 | 70.26 |
| BT-20 | Abemaciclib | 16.79 | 0.79 | 165 | 3.95 | 5.53 | 5.32 |
| BT-20 | ABT-199 | 13.39 | 0.62 | 140 | 6.83 | 5.47 | 5.94 |
| BT-20 | ABT-263 | 84.06 | 0.05 | 165 | 36.91 | 37.77 | 37.81 |
| BT-20 | BMN 673 | 13.00 | 0.67 | 130 | 6.61 | 7.19 | 7.05 |
| BT-20 | Carboplatin | 5.46 | 0.66 | 170 | 7.81 | 1.55 | −0.31 |
| BT-20 | Cisplatin | 2.27 | 0.90 | 65 | 13.49 | −0.68 | −2.71 |
| BT-20 | Docetaxel | 39.72 | 0.05 | 170 | 27.23 | 21.05 | 19.90 |
| BT-20 | Doxorubicin Hcl | 8.20 | 0.71 | 180 | 18.53 | 5.68 | 3.58 |
| BT-20 | Everolimus | 11.08 | 0.48 | 115 | 8.37 | 8.23 | 7.02 |
| BT-20 | Fulvestrant | 8.19 | 0.88 | 110 | 3.55 | 3.62 | 3.44 |
| BT-20 | GDC-0068 | 26.99 | 0.15 | 160 | 14.37 | 13.36 | 11.91 |
| BT-20 | Gemcitabine Hydrochloride | 11.12 | 0.70 | 140 | 4.35 | 4.94 | 3.32 |
| BT-20 | Lapatinib Ditosylate | 36.25 | 0.18 | 170 | 18.16 | 17.05 | 16.93 |
| BT-20 | LEE011 | 2.30 | 0.78 | 50 | −2.26 | −1.79 | −2.17 |
| BT-20 | Neratinib | 58.64 | 0.05 | 180 | 38.29 | 28.06 | 28.33 |
| BT-20 | Olaparib | 4.78 | 0.88 | 160 | 0.80 | 0.38 | 0.63 |
| BT-20 | Paclitaxel | 31.95 | 0.05 | 165 | 21.83 | 16.17 | 14.29 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| BT-20 | PD-0332991 | 3.95 | 1.30 | 90 | −2.05 | −0.62 | −1.20 |
| BT-20 | Tamoxifen Citrate | 4.67 | 1.22 | 180 | 8.13 | 3.19 | 1.49 |
| BT-474 | A-1331852 | 89.30 | 0.02 | 175 | 43.35 | 40.44 | 42.32 |
| BT-474 | Abemaciclib | 2.01 | 0.79 | 40 | −4.59 | −7.14 | −6.22 |
| BT-474 | ABT-199 | 7.07 | 0.27 | 40 | 4.03 | 3.88 | 3.87 |
| BT-474 | ABT-263 | 28.39 | 0.22 | 170 | 12.98 | 13.30 | 13.24 |
| BT-474 | BMN 673 | 3.44 | 0.52 | 105 | −5.11 | −4.33 | −4.84 |
| BT-474 | Carboplatin | 2.18 | 1.30 | 45 | −3.87 | −5.02 | −4.61 |
| BT-474 | Cisplatin | 2.85 | 0.47 | 105 | −2.63 | −4.63 | −4.42 |
| BT-474 | Docetaxel | 14.51 | 0.24 | 140 | 16.39 | 9.80 | 8.62 |
| BT-474 | Doxorubicin Hcl | 13.22 | 0.18 | 170 | 10.20 | 3.53 | 3.33 |
| BT-474 | Everolimus | 2.41 | 1.27 | 35 | 3.26 | −1.26 | −2.71 |
| BT-474 | Fulvestrant | 6.48 | 0.79 | 125 | 2.68 | 1.47 | 1.42 |
| BT-474 | GDC-0068 | 26.12 | 0.09 | 170 | 19.73 | 11.84 | 10.58 |
| BT-474 | Gemcitabine Hydrochloride | 1.78 | 0.10 | 50 | −4.12 | −5.02 | −4.59 |
| BT-474 | Lapatinib Ditosylate | 33.06 | 0.02 | 180 | 36.82 | 16.41 | 13.78 |
| BT-474 | LEE011 | 3.21 | 0.90 | 50 | −2.38 | −1.88 | −1.90 |
| BT-474 | Neratinib | 39.01 | 0.05 | 170 | 28.98 | 20.36 | 18.83 |
| BT-474 | Olaparib | 4.68 | 0.44 | 30 | 0.14 | −1.01 | 0.72 |
| BT-474 | Paclitaxel | 15.03 | 0.16 | 145 | 14.99 | 6.99 | 6.64 |
| BT-474 | PD-0332991 | 10.13 | 0.99 | 160 | 1.73 | 0.72 | 0.25 |
| BT-474 | Tamoxifen Citrate | 7.16 | 0.67 | 50 | 14.23 | 5.21 | 5.46 |
| BT-549 | A-1331852 | 167.12 | 0.01 | 80 | 75.65 | 75.61 | 76.76 |
| BT-549 | Abemaciclib | 25.88 | 0.19 | 80 | 15.59 | 16.85 | 17.00 |
| BT-549 | ABT-199 | 8.34 | 0.61 | 80 | 6.96 | 8.94 | 9.13 |
| BT-549 | ABT-263 | 79.44 | 0.05 | 95 | 43.82 | 39.11 | 43.65 |
| BT-549 | BMN 673 | 14.59 | 0.17 | 95 | 11.56 | 12.37 | 12.52 |
| BT-549 | Carboplatin | 5.26 | 1.30 | 135 | 6.55 | 4.24 | 4.88 |
| BT-549 | Cisplatin | 6.80 | 1.01 | 160 | 7.35 | 2.86 | 4.16 |
| BT-549 | Docetaxel | 39.66 | 0.13 | 110 | 22.57 | 22.13 | 22.04 |
| BT-549 | Doxorubicin Hcl | 14.76 | 0.54 | 175 | 14.37 | 9.58 | 9.92 |
| BT-549 | Everolimus | 7.35 | 0.11 | 70 | 5.93 | 8.22 | 7.87 |
| BT-549 | Fulvestrant | 6.08 | 0.34 | 55 | 3.56 | 7.74 | 7.73 |
| BT-549 | GDC-0068 | 14.89 | 0.24 | 85 | 9.51 | 11.92 | 11.91 |
| BT-549 | Gemcitabine Hydrochloride | 18.17 | 0.05 | 135 | 13.68 | 11.18 | 11.37 |
| BT-549 | Lapatinib Ditosylate | 13.94 | 0.45 | 85 | 10.19 | 9.95 | 10.55 |
| BT-549 | LEE011 | 3.79 | 0.35 | 45 | 0.64 | 2.82 | 4.10 |
| BT-549 | Neratinib | 25.15 | 0.31 | 175 | 17.92 | 13.17 | 13.98 |
| BT-549 | Olaparib | 6.59 | 0.76 | 80 | 6.76 | 8.17 | 8.67 |
| BT-549 | Paclitaxel | 29.74 | 0.27 | 105 | 17.66 | 17.51 | 17.48 |
| BT-549 | PD-0332991 | 3.67 | 1.07 | 90 | 5.11 | 3.60 | 5.15 |
| BT-549 | Tamoxifen Citrate | 3.81 | 0.42 | 45 | 9.75 | 6.66 | 6.84 |
| CAL-120 | A-1331852 | 55.20 | 0.04 | 170 | 28.08 | 26.51 | 28.14 |
| CAL-120 | Abemaciclib | 1.03 | 1.78 | 60 | −5.16 | −5.98 | −5.00 |
| CAL-120 | ABT-199 | 0.62 | 0.85 | 20 | 3.85 | −1.21 | −0.16 |
| CAL-120 | ABT-263 | 24.96 | 0.21 | 50 | 15.10 | 15.51 | 16.04 |
| CAL-120 | BMN 673 | 0.01 | 2.73 | 20 | −3.70 | −7.12 | −9.94 |
| CAL-120 | Carboplatin | 0.49 | 0.58 | 20 | −0.19 | −1.52 | −0.25 |
| CAL-120 | Cisplatin | 1.13 | 0.19 | 35 | 1.51 | 0.51 | 1.48 |
| CAL-120 | Docetaxel | 11.63 | 0.87 | 95 | 8.92 | 7.98 | 8.39 |
| CAL-120 | Doxorubicin Hcl | 2.50 | 0.64 | 55 | 0.28 | −0.57 | 0.01 |
| CAL-120 | Everolimus | 0.53 | 0.11 | 20 | −2.79 | −1.61 | −1.62 |
| CAL-120 | Fulvestrant | 0.28 | 0.68 | 20 | −4.96 | −4.48 | −4.09 |
| CAL-120 | GDC-0068 | 1.05 | 0.04 | 25 | −1.18 | −0.50 | 0.09 |
| CAL-120 | Gemcitabine Hydrochloride | 0.88 | 0.21 | 35 | −5.00 | −5.87 | −4.98 |
| CAL-120 | Lapatinib Ditosylate | 0.86 | 1.36 | 35 | 1.71 | −2.16 | 1.68 |
| CAL-120 | LEE011 | 0.15 | 0.62 | 20 | −1.14 | −5.68 | −5.28 |
| CAL-120 | Neratinib | 11.20 | 0.82 | 115 | 4.43 | 4.29 | 3.99 |
| CAL-120 | Olaparib | 0.11 | 0.85 | 20 | 3.31 | −3.93 | −3.49 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| CAL-120 | Paclitaxel | 7.80 | 0.95 | 95 | 0.98 | 2.18 | 1.16 |
| CAL-120 | PD-0332991 | 0.11 | 1.81 | 20 | −0.11 | −7.17 | −6.92 |
| CAL-120 | Tamoxifen Citrate | 0.79 | 0.74 | 25 | −0.11 | −0.32 | −0.19 |
| CAL-148 | A-1331852 | 129.75 | 0.01 | 70 | 51.23 | 55.15 | 56.80 |
| CAL-148 | Abemaciclib | 15.50 | 0.70 | 135 | 6.48 | 5.91 | 6.28 |
| CAL-148 | ABT-199 | 2.74 | 0.47 | 55 | 3.32 | −0.66 | 3.11 |
| CAL-148 | ABT-263 | 51.82 | 0.10 | 70 | 28.25 | 22.50 | 27.96 |
| CAL-148 | BMN 673 | 51.37 | 0.03 | 85 | 32.27 | 30.51 | 33.70 |
| CAL-148 | Carboplatin | 24.09 | 0.27 | 125 | 11.40 | 12.06 | 11.89 |
| CAL-148 | Cisplatin | 37.06 | 0.13 | 140 | 19.20 | 19.03 | 18.76 |
| CAL-148 | Docetaxel | 28.74 | 0.18 | 145 | 15.94 | 13.90 | 12.92 |
| CAL-148 | Doxorubicin Hcl | 37.02 | 0.06 | 170 | 20.68 | 14.71 | 17.38 |
| CAL-148 | Everolimus | 18.16 | 0.07 | 80 | 5.67 | 9.58 | 8.56 |
| CAL-148 | Fulvestrant | 4.58 | 1.08 | 80 | −1.80 | −2.13 | −0.78 |
| CAL-148 | GDC-0068 | 22.09 | 0.20 | 180 | 15.98 | 11.23 | 11.35 |
| CAL-148 | Gemcitabine Hydrochloride | 35.99 | 0.36 | 85 | 19.19 | 20.88 | 20.22 |
| CAL-148 | Lapatinib Ditosylate | 8.14 | 0.38 | 60 | 2.28 | 4.93 | 4.85 |
| CAL-148 | LEE011 | 0.81 | 0.86 | 25 | −4.27 | −5.99 | −4.10 |
| CAL-148 | Neratinib | 29.60 | 0.21 | 180 | 18.81 | 13.97 | 17.68 |
| CAL-148 | Olaparib | 9.33 | 0.27 | 40 | 3.34 | 5.39 | 5.40 |
| CAL-148 | Paclitaxel | 19.91 | 0.25 | 160 | 14.13 | 10.57 | 10.51 |
| CAL-148 | PD-0332991 | 0.81 | 0.21 | 30 | −2.31 | −5.69 | −4.24 |
| CAL-148 | Tamoxifen Citrate | 1.93 | 0.69 | 30 | −2.30 | −4.25 | −4.43 |
| CAL-51 | A-1331852 | 118.96 | 0.01 | 20 | 56.43 | 55.36 | 56.58 |
| CAL-51 | Abemaciclib | 2.51 | 1.31 | 165 | 1.55 | −0.56 | 2.06 |
| CAL-51 | ABT-199 | 0.56 | 0.58 | 20 | 0.44 | −2.62 | 0.83 |
| CAL-51 | ABT-263 | 39.59 | 0.09 | 20 | 18.29 | 17.50 | 18.72 |
| CAL-51 | BMN 673 | 6.14 | 0.26 | 60 | 6.45 | 8.03 | 8.01 |
| CAL-51 | Carboplatin | 5.53 | 0.89 | 165 | 2.81 | 2.17 | 2.97 |
| CAL-51 | Cisplatin | 9.30 | 0.48 | 180 | 7.18 | 4.36 | 6.98 |
| CAL-51 | Docetaxel | 4.88 | 0.70 | 90 | 2.26 | 3.35 | 3.12 |
| CAL-51 | Doxorubicin Hcl | 16.62 | 0.21 | 150 | 7.78 | 6.53 | 7.74 |
| CAL-51 | Everolimus | 1.34 | 0.20 | 55 | −2.55 | 0.45 | 0.41 |
| CAL-51 | Fulvestrant | 0.47 | 0.70 | 20 | 0.71 | −1.89 | 0.82 |
| CAL-51 | GDC-0068 | 1.93 | 0.66 | 45 | 1.90 | 2.22 | 2.48 |
| CAL-51 | Gemcitabine Hydrochloride | 5.10 | 0.47 | 90 | 3.26 | 3.22 | 3.49 |
| CAL-51 | Lapatinib Ditosylate | 0.65 | 1.14 | 45 | 1.57 | −1.26 | 1.38 |
| CAL-51 | LEE011 | 0.34 | 0.77 | 20 | −1.68 | −1.56 | −1.27 |
| CAL-51 | Neratinib | 14.86 | 0.29 | 180 | 6.99 | 4.62 | 6.71 |
| CAL-51 | Olaparib | 1.89 | 0.55 | 50 | 1.50 | 1.03 | 2.21 |
| CAL-51 | Paclitaxel | 5.26 | 0.50 | 95 | 2.63 | 3.93 | 3.88 |
| CAL-51 | PD-0332991 | 0.38 | 0.82 | 20 | −3.23 | −1.09 | −1.26 |
| CAL-51 | Tamoxifen Citrate | 0.43 | 1.06 | 40 | −0.44 | −1.18 | −0.56 |
| CAL-85-1 | A-1331852 | 114.90 | 0.01 | 85 | 49.08 | 54.69 | 53.39 |
| CAL-85-1 | Abemaciclib | 6.47 | 0.77 | 125 | 2.60 | 3.28 | 3.04 |
| CAL-85-1 | ABT-199 | 1.08 | 0.83 | 70 | −1.49 | −2.11 | −1.27 |
| CAL-85-1 | ABT-263 | 29.64 | 0.17 | 65 | 13.36 | 16.06 | 15.97 |
| CAL-85-1 | BMN 673 | 13.48 | 0.10 | 80 | 9.61 | 13.84 | 13.04 |
| CAL-85-1 | Carboplatin | 4.18 | 1.11 | 110 | 4.84 | 3.68 | 3.42 |
| CAL-85-1 | Cisplatin | 6.29 | 1.09 | 115 | 6.84 | 4.63 | 4.66 |
| CAL-85-1 | Docetaxel | 19.64 | 0.27 | 145 | 13.68 | 11.86 | 11.10 |
| CAL-85-1 | Doxorubicin Hcl | 7.42 | 0.48 | 170 | 5.45 | 3.18 | 3.69 |
| CAL-85-1 | Everolimus | 16.26 | 0.04 | 80 | 10.37 | 14.41 | 13.60 |
| CAL-85-1 | Fulvestrant | 2.63 | 0.64 | 75 | −4.57 | −0.20 | −0.68 |
| CAL-85-1 | GDC-0068 | 4.37 | 0.22 | 80 | −1.63 | 2.26 | 1.63 |
| CAL-85-1 | Gemcitabine Hydrochloride | 10.96 | 0.58 | 105 | 9.98 | 8.91 | 7.81 |
| CAL-85-1 | Lapatinib Ditosylate | 22.90 | 0.58 | 165 | 15.87 | 16.23 | 15.59 |
| CAL-85-1 | LEE011 | 0.23 | 0.64 | 25 | −5.58 | −9.15 | −7.95 |
| CAL-85-1 | Neratinib | 28.31 | 0.13 | 150 | 22.07 | 18.05 | 16.51 |
| CAL-85-1 | Olaparib | 5.10 | 0.67 | 75 | 4.52 | 5.66 | 6.67 |
| CAL-85-1 | Paclitaxel | 15.51 | 0.23 | 150 | 10.82 | 7.76 | 6.83 |
| CAL-85-1 | PD-0332991 | 0.30 | 0.75 | 20 | −7.60 | −8.20 | −7.47 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| CAL-85-1 | Tamoxifen Citrate | 3.03 | 0.49 | 35 | 4.60 | 1.09 | 2.25 |
| CAMA-1 | A-1331852 | 89.71 | 0.02 | 180 | 41.48 | 38.74 | 40.35 |
| CAMA-1 | Abemaciclib | 1.56 | 0.32 | 60 | −6.25 | −10.24 | −10.33 |
| CAMA-1 | ABT-199 | 15.23 | 0.38 | 180 | 8.30 | 4.83 | 8.10 |
| CAMA-1 | ABT-263 | 41.66 | 0.14 | 180 | 19.67 | 17.49 | 19.32 |
| CAMA-1 | BMN 673 | 16.77 | 0.44 | 180 | 14.84 | 11.15 | 11.46 |
| CAMA-1 | Carboplatin | 12.48 | 0.46 | 180 | 9.50 | 6.02 | 6.21 |
| CAMA-1 | Cisplatin | 18.49 | 0.23 | 180 | 16.63 | 9.61 | 9.28 |
| CAMA-1 | Docetaxel | 13.30 | 0.06 | 180 | 29.57 | 6.98 | 4.88 |
| CAMA-1 | Doxorubicin Hcl | 18.00 | 0.15 | 180 | 28.11 | 9.62 | 8.10 |
| CAMA-1 | Everolimus | 7.90 | 0.44 | 150 | 10.06 | 2.71 | 3.20 |
| CAMA-1 | Fulvestrant | 2.09 | 0.50 | 55 | 4.38 | −0.63 | −0.83 |
| CAMA-1 | GDC-0068 | 27.46 | 0.11 | 180 | 26.60 | 14.33 | 13.52 |
| CAMA-1 | Gemcitabine Hydrochloride | 40.36 | 0.06 | 180 | 26.55 | 18.50 | 18.89 |
| CAMA-1 | Lapatinib Ditosylate | 4.06 | 0.90 | 175 | 2.37 | −1.25 | 0.83 |
| CAMA-1 | LEE011 | 1.09 | 0.73 | 30 | −3.85 | −6.33 | −6.51 |
| CAMA-1 | Neratinib | 6.88 | 0.40 | 180 | 26.19 | 5.28 | 3.50 |
| CAMA-1 | Olaparib | 4.78 | 1.12 | 150 | 5.62 | 2.59 | 3.95 |
| CAMA-1 | Paclitaxel | 11.56 | 0.05 | 180 | 27.04 | 6.70 | 4.55 |
| CAMA-1 | PD-0332991 | 0.99 | 0.49 | 75 | −4.96 | −11.74 | −11.95 |
| CAMA-1 | Tamoxifen Citrate | 1.26 | 0.27 | 35 | 5.26 | −4.27 | −4.60 |
| DU-4475 | A-1331852 | 49.81 | 0.41 | 180 | 34.50 | 31.29 | 31.62 |
| DU-4475 | Abemaciclib | 5.07 | 1.25 | 125 | 6.92 | 5.32 | 5.72 |
| DU-4475 | ABT-199 | 10.64 | 1.15 | 160 | 10.43 | 8.46 | 10.37 |
| DU-4475 | ABT-263 | 35.34 | 0.48 | 175 | 24.62 | 22.37 | 22.67 |
| DU-4475 | BMN 673 | 12.59 | 0.90 | 130 | 14.54 | 11.67 | 11.80 |
| DU-4475 | Carboplatin | 8.88 | 0.76 | 180 | 10.04 | 7.26 | 6.59 |
| DU-4475 | Cisplatin | 7.00 | 0.29 | 40 | 14.10 | 5.48 | 5.54 |
| DU-4475 | Docetaxel | 20.30 | 0.25 | 165 | 19.28 | 13.68 | 12.74 |
| DU-4475 | Doxorubicin Hcl | 13.23 | 0.46 | 170 | 20.94 | 7.65 | 6.93 |
| DU-4475 | Everolimus | 2.43 | 0.64 | 25 | 4.29 | 1.94 | 0.97 |
| DU-4475 | Fulvestrant | 2.58 | 1.08 | 80 | 4.93 | 0.13 | 4.51 |
| DU-4475 | GDC-0068 | 0.20 | | 20 | −5.18 | −7.77 | −5.05 |
| DU-4475 | Gemcitabine Hydrochloride | 0.17 | | 20 | −3.76 | −3.58 | −2.68 |
| DU-4475 | Lapatinib Ditosylate | 10.33 | 0.65 | 180 | 10.51 | 6.40 | 6.21 |
| DU-4475 | LEE011 | 0.98 | 0.47 | 30 | 1.64 | 0.20 | 1.04 |
| DU-4475 | Neratinib | 2.06 | 0.43 | 20 | 10.55 | 1.06 | 0.39 |
| DU-4475 | Olaparib | 4.61 | 1.00 | 100 | 7.40 | 5.68 | 5.80 |
| DU-4475 | Paclitaxel | 13.63 | 0.57 | 180 | 13.03 | 8.70 | 7.85 |
| DU-4475 | PD-0332991 | 0.30 | 0.97 | 20 | 0.05 | −1.86 | −0.06 |
| DU-4475 | Tamoxifen Citrate | 2.35 | 0.80 | 180 | 7.28 | 0.20 | −0.16 |
| EVSA-T | A-1331852 | 63.11 | 0.11 | 180 | 31.72 | 28.03 | 29.10 |
| EVSA-T | Abemaciclib | 0.77 | 0.64 | 20 | 0.41 | −2.86 | −2.48 |
| EVSA-T | ABT-199 | 4.67 | 1.07 | 155 | 1.29 | −0.86 | 0.99 |
| EVSA-T | ABT-263 | 28.16 | 0.36 | 180 | 15.42 | 14.19 | 14.63 |
| EVSA-T | BMN 673 | 7.17 | 0.76 | 130 | 12.51 | 5.77 | 5.78 |
| EVSA-T | Carboplatin | 4.72 | 0.84 | 180 | 9.55 | −0.13 | −0.33 |
| EVSA-T | Cisplatin | 2.53 | 0.39 | 25 | 20.06 | 3.60 | 1.90 |
| EVSA-T | Docetaxel | 24.87 | 0.28 | 180 | 32.24 | 12.42 | 12.22 |
| EVSA-T | Doxorubicin Hcl | 5.36 | 0.19 | 40 | 29.57 | 3.98 | 3.12 |
| EVSA-T | Everolimus | 1.85 | 0.99 | 45 | 10.56 | −0.76 | −1.22 |
| EVSA-T | Fulvestrant | 3.72 | 1.10 | 160 | 6.75 | 1.08 | 1.59 |
| EVSA-T | GDC-0068 | 18.16 | 0.27 | 180 | 38.10 | 10.77 | 8.56 |
| EVSA-T | Gemcitabine Hydrochloride | 5.11 | 1.07 | 155 | 9.65 | 2.02 | 1.29 |
| EVSA-T | Lapatinib Ditosylate | 7.46 | 0.77 | 180 | 11.52 | 4.07 | 3.83 |
| EVSA-T | LEE011 | 0.34 | 0.63 | 30 | −0.43 | −2.18 | −1.37 |
| EVSA-T | Neratinib | 1.92 | 0.51 | 25 | 2.50 | 1.44 | 1.31 |
| EVSA-T | Olaparib | 4.47 | 1.17 | 130 | 6.05 | 3.16 | 3.21 |
| EVSA-T | Paclitaxel | 21.77 | 0.26 | 180 | 29.14 | 9.72 | 9.35 |
| EVSA-T | PD-0332991 | 0.21 | 0.77 | 20 | −4.20 | −6.37 | −5.67 |
| EVSA-T | Tamoxifen Citrate | 2.53 | 0.68 | 155 | 19.96 | 2.04 | 0.09 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| HCC1143 | A-1331852 | 89.24 | 0.00 | 90 | 53.10 | 51.70 | 52.79 |
| HCC1143 | Abemaciclib | 7.43 | 0.41 | 70 | 10.33 | 2.87 | 9.43 |
| HCC1143 | ABT-199 | 3.01 | 0.82 | 45 | 2.43 | −2.65 | −1.50 |
| HCC1143 | ABT-263 | 43.54 | 0.05 | 90 | 27.56 | 26.07 | 27.51 |
| HCC1143 | BMN 673 | 4.91 | 0.53 | 65 | 0.82 | 2.15 | 1.38 |
| HCC1143 | Carboplatin | 3.59 | 0.82 | 105 | −4.47 | −2.24 | −2.60 |
| HCC1143 | Cisplatin | 2.45 | 0.39 | 55 | −0.20 | −5.78 | −3.31 |
| HCC1143 | Docetaxel | 18.84 | 1.22 | 115 | 11.00 | 9.41 | 8.32 |
| HCC1143 | Doxorubicin Hcl | 10.49 | 0.42 | 175 | 6.14 | 3.98 | 4.06 |
| HCC1143 | Everolimus | 9.36 | 0.64 | 95 | 8.68 | 8.45 | 10.21 |
| HCC1143 | Fulvestrant | 2.79 | 1.54 | 115 | 0.82 | −4.16 | 0.02 |
| HCC1143 | GDC-0068 | 3.73 | 0.56 | 40 | 1.41 | −1.97 | 1.22 |
| HCC1143 | Gemcitabine Hydrochloride | 9.41 | 0.15 | 90 | 4.32 | 8.39 | 7.81 |
| HCC1143 | Lapatinib Ditosylate | 15.37 | 0.54 | 95 | 8.05 | 8.81 | 9.03 |
| HCC1143 | LEE011 | 1.30 | | 55 | −3.25 | −7.75 | −9.95 |
| HCC1143 | Neratinib | 12.39 | 0.47 | 75 | 14.84 | 7.69 | 8.83 |
| HCC1143 | Olaparib | 4.20 | 0.24 | 45 | 4.87 | 3.84 | 3.62 |
| HCC1143 | Paclitaxel | 13.36 | 0.35 | 140 | 9.86 | 4.50 | 5.40 |
| HCC1143 | PD-0332991 | 1.96 | 0.75 | 60 | −2.16 | −3.77 | −0.95 |
| HCC1143 | Tamoxifen Citrate | 5.15 | 0.19 | 60 | 11.08 | −0.45 | 8.13 |
| HCC1569 | A-1331852 | 86.99 | 0.01 | 180 | 43.44 | 40.52 | 40.04 |
| HCC1569 | Abemaciclib | 19.73 | 0.18 | 85 | 14.07 | 13.17 | 14.38 |
| HCC1569 | ABT-199 | 14.35 | 0.51 | 90 | 15.86 | 14.50 | 16.04 |
| HCC1569 | ABT-263 | 46.64 | 0.13 | 165 | 27.53 | 24.55 | 26.18 |
| HCC1569 | BMN 673 | 10.50 | 0.55 | 95 | 9.55 | 11.82 | 11.51 |
| HCC1569 | Carboplatin | 2.85 | 0.43 | 30 | 4.84 | 2.05 | 2.91 |
| HCC1569 | Cisplatin | 1.82 | 0.43 | 25 | 1.33 | −1.41 | −2.74 |
| HCC1569 | Docetaxel | 11.65 | 0.24 | 100 | 6.58 | 8.56 | 9.52 |
| HCC1569 | Doxorubicin Hcl | 16.62 | 0.49 | 115 | 12.86 | 10.97 | 11.79 |
| HCC1569 | Everolimus | 3.45 | 0.83 | 75 | 2.35 | 5.10 | 4.65 |
| HCC1569 | Fulvestrant | 5.92 | 0.86 | 95 | 3.84 | 4.70 | 5.59 |
| HCC1569 | GDC-0068 | 15.41 | 0.24 | 105 | 9.34 | 10.52 | 10.52 |
| HCC1569 | Gemcitabine Hydrochloride | 5.52 | 0.68 | 85 | 3.74 | 6.80 | 6.28 |
| HCC1569 | Lapatinib Ditosylate | 14.44 | 0.53 | 110 | 11.57 | 11.98 | 12.21 |
| HCC1569 | LEE011 | 3.87 | 0.47 | 35 | 5.70 | 1.89 | 5.08 |
| HCC1569 | Neratinib | 23.33 | 0.76 | 140 | 17.69 | 11.68 | 14.89 |
| HCC1569 | Olaparib | 4.98 | 0.84 | 95 | 7.47 | 5.26 | 8.00 |
| HCC1569 | Paclitaxel | 11.74 | 0.41 | 95 | 7.47 | 9.85 | 10.17 |
| HCC1569 | PD-0332991 | 5.78 | 0.78 | 85 | 8.10 | 4.93 | 8.19 |
| HCC1569 | Tamoxifen Citrate | 4.62 | 0.50 | 45 | 9.08 | 4.62 | 6.10 |
| HCC1806 | A-1331852 | 183.39 | 0.00 | 80 | 83.58 | 85.67 | 85.91 |
| HCC1806 | Abemaciclib | 4.43 | 1.09 | 125 | 4.89 | 0.30 | 3.10 |
| HCC1806 | ABT-199 | 6.31 | 0.83 | 75 | 3.80 | 4.70 | 5.23 |
| HCC1806 | ABT-263 | 90.68 | 0.03 | 70 | 45.40 | 46.37 | 46.26 |
| HCC1806 | BMN 673 | 26.09 | 0.15 | 45 | 15.34 | 21.19 | 21.61 |
| HCC1806 | Carboplatin | 9.06 | 0.33 | 80 | 11.43 | 4.44 | 9.76 |
| HCC1806 | Cisplatin | 7.76 | 0.22 | 70 | 8.46 | 3.81 | 5.93 |
| HCC1806 | Docetaxel | 25.50 | 0.14 | 175 | 17.46 | 12.45 | 12.66 |
| HCC1806 | Doxorubicin Hcl | 17.07 | 0.61 | 160 | 13.65 | 10.25 | 11.15 |
| HCC1806 | Everolimus | 2.52 | 1.14 | 55 | 5.19 | 2.88 | 5.59 |
| HCC1806 | Fulvestrant | 2.60 | 0.80 | 65 | −0.20 | −0.86 | 1.90 |
| HCC1806 | GDC-0068 | 2.21 | 0.83 | 60 | 4.78 | −2.22 | 2.14 |
| HCC1806 | Gemcitabine Hydrochloride | 30.81 | 0.13 | 110 | 17.89 | 18.06 | 17.74 |
| HCC1806 | Lapatinib Ditosylate | 22.18 | 0.74 | 135 | 16.71 | 16.19 | 17.69 |
| HCC1806 | LEE011 | 0.65 | 0.56 | 35 | −3.98 | −8.72 | −4.05 |
| HCC1806 | Neratinib | 37.41 | 0.15 | 180 | 25.34 | 19.39 | 21.61 |
| HCC1806 | Olaparib | 7.73 | 0.21 | 60 | 7.25 | 8.26 | 8.49 |
| HCC1806 | Paclitaxel | 25.66 | 0.10 | 170 | 16.84 | 12.59 | 12.37 |
| HCC1806 | PD-0332991 | 0.99 | 0.02 | 20 | −1.37 | −4.31 | −1.04 |
| HCC1806 | Tamoxifen Citrate | 3.03 | 0.84 | 125 | 4.65 | 0.35 | 2.24 |
| HCC1937 | A-1331852 | 157.43 | 0.00 | 80 | 69.83 | 71.58 | 71.06 |
| HCC1937 | Abemaciclib | 28.56 | 0.26 | 65 | 16.67 | 12.85 | 16.44 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| HCC1937 | ABT-199 | 1.43 | 0.22 | 20 | 8.42 | 2.68 | 4.59 |
| HCC1937 | ABT-263 | 43.69 | 0.18 | 85 | 26.87 | 22.28 | 26.31 |
| HCC1937 | BMN 673 | 3.27 | 0.51 | 60 | 5.18 | 0.65 | 4.96 |
| HCC1937 | Carboplatin | 4.59 | 0.44 | 25 | 5.97 | 3.52 | 4.56 |
| HCC1937 | Cisplatin | 1.75 | 1.07 | 105 | 1.32 | −1.15 | −0.59 |
| HCC1937 | Docetaxel | 11.60 | 0.12 | 80 | 10.96 | 11.56 | 11.67 |
| HCC1937 | Doxorubicin Hcl | 8.57 | 0.15 | 110 | 5.83 | 6.29 | 6.21 |
| HCC1937 | Everolimus | 4.89 | 0.54 | 75 | 1.96 | 3.68 | 4.63 |
| HCC1937 | Fulvestrant | 2.38 | 0.98 | 80 | 2.31 | −0.65 | 2.38 |
| HCC1937 | GDC-0068 | 6.18 | 0.44 | 80 | 8.88 | 6.08 | 8.48 |
| HCC1937 | Gemcitabine Hydrochloride | 2.33 | 0.45 | 60 | 2.34 | 0.77 | 2.36 |
| HCC1937 | Lapatinib Ditosylate | 4.88 | 1.22 | 125 | 6.63 | 3.46 | 5.12 |
| HCC1937 | LEE011 | 2.13 | 0.74 | 65 | 2.31 | −2.66 | 1.04 |
| HCC1937 | Neratinib | 13.10 | 0.84 | 180 | 13.93 | 5.77 | 10.37 |
| HCC1937 | Olaparib | 1.77 | 0.63 | 70 | 2.27 | −1.83 | 3.06 |
| HCC1937 | Paclitaxel | 8.79 | 0.18 | 85 | 8.79 | 8.44 | 8.53 |
| HCC1937 | PD-0332991 | 21.45 | 0.28 | 75 | 14.96 | 11.05 | 14.74 |
| HCC1937 | Tamoxifen Citrate | 1.66 | 1.02 | 80 | 1.39 | −0.84 | −0.54 |
| HCC1954 | A-1331852 | 121.26 | 0.01 | 175 | 53.64 | 55.54 | 55.53 |
| HCC1954 | Abemaciclib | 12.74 | 0.89 | 175 | 1.45 | −0.39 | −1.29 |
| HCC1954 | ABT-199 | 17.16 | 0.60 | 165 | 12.55 | 10.72 | 12.18 |
| HCC1954 | ABT-263 | 76.44 | 0.03 | 160 | 36.37 | 36.78 | 37.10 |
| HCC1954 | BMN 673 | 9.80 | 0.56 | 135 | 7.66 | 7.39 | 8.33 |
| HCC1954 | Carboplatin | 5.12 | 1.07 | 125 | 2.26 | 2.07 | 0.71 |
| HCC1954 | Cisplatin | 5.58 | 0.84 | 180 | 5.89 | −0.89 | −1.88 |
| HCC1954 | Docetaxel | 25.34 | 0.07 | 165 | 25.28 | 14.25 | 12.73 |
| HCC1954 | Doxorubicin Hcl | 9.19 | 0.20 | 50 | 12.81 | 6.34 | 5.15 |
| HCC1954 | Everolimus | 36.09 | 0.12 | 145 | 20.04 | 23.41 | 21.71 |
| HCC1954 | Fulvestrant | 16.73 | 0.95 | 160 | 11.35 | 12.18 | 11.84 |
| HCC1954 | GDC-0068 | 33.91 | 0.16 | 180 | 19.16 | 18.41 | 17.07 |
| HCC1954 | Gemcitabine Hydrochloride | 7.13 | 0.28 | 80 | 3.78 | 5.17 | 5.09 |
| HCC1954 | Lapatinib Ditosylate | 36.40 | 0.07 | 170 | 26.26 | 21.00 | 19.03 |
| HCC1954 | LEE011 | 4.48 | 0.72 | 145 | −0.75 | −1.44 | −1.17 |
| HCC1954 | Neratinib | 38.93 | 0.06 | 175 | 37.73 | 19.30 | 19.31 |
| HCC1954 | Olaparib | 4.49 | 0.92 | 160 | 1.68 | 0.48 | 1.64 |
| HCC1954 | Paclitaxel | 24.52 | 0.05 | 170 | 21.82 | 13.19 | 11.20 |
| HCC1954 | PD-0332991 | 1.20 | 0.47 | 35 | −7.91 | −8.72 | −7.32 |
| HCC1954 | Tamoxifen Citrate | 4.16 | 0.18 | 35 | 10.16 | 3.65 | 1.88 |
| HCC2218 | A-1331852 | 99.88 | 0.01 | 165 | 47.29 | 47.84 | 46.72 |
| HCC2218 | Abemaciclib | 4.14 | 1.44 | 135 | −2.40 | −5.74 | −6.61 |
| HCC2218 | ABT-199 | 15.06 | 0.43 | 155 | 7.82 | 8.19 | 7.59 |
| HCC2218 | ABT-263 | 59.76 | 0.07 | 160 | 28.59 | 29.77 | 28.05 |
| HCC2218 | BMN 673 | 5.35 | 0.90 | 95 | 1.41 | 0.71 | 0.15 |
| HCC2218 | Carboplatin | 5.27 | 0.70 | 45 | 2.59 | 0.49 | −1.33 |
| HCC2218 | Cisplatin | 7.99 | 0.54 | 165 | 9.34 | 2.71 | −0.66 |
| HCC2218 | Docetaxel | 10.71 | 0.42 | 130 | 11.69 | 6.53 | 5.20 |
| HCC2218 | Doxorubicin Hcl | 8.60 | 0.35 | 180 | 13.67 | 0.99 | −0.88 |
| HCC2218 | Everolimus | 3.37 | 0.99 | 115 | −0.77 | −0.63 | −2.03 |
| HCC2218 | Fulvestrant | 3.85 | | 160 | 1.16 | 1.89 | −1.02 |
| HCC2218 | GDC-0068 | 22.09 | 0.13 | 165 | 10.70 | 8.89 | 7.71 |
| HCC2218 | Gemcitabine Hydrochloride | 6.54 | 0.36 | 90 | 5.46 | 4.02 | 2.80 |
| HCC2218 | Lapatinib Ditosylate | 42.84 | 0.02 | 165 | 44.16 | 21.76 | 19.27 |
| HCC2218 | LEE011 | 1.69 | 0.73 | 75 | −5.40 | −4.99 | −5.90 |
| HCC2218 | Neratinib | 20.85 | 0.05 | 175 | 30.06 | 10.84 | 8.50 |
| HCC2218 | Olaparib | 2.66 | 0.88 | 70 | −1.34 | −1.12 | −1.71 |
| HCC2218 | Paclitaxel | 11.32 | 0.55 | 135 | 10.74 | 7.96 | 6.01 |
| HCC2218 | PD-0332991 | 7.27 | 1.10 | 150 | −0.96 | −1.25 | −3.22 |
| HCC2218 | Tamoxifen Citrate | 8.45 | 0.45 | 50 | 13.34 | 5.23 | 2.51 |
| HCC38 | A-1331852 | 60.48 | 0.03 | 170 | 36.56 | 31.80 | 30.82 |
| HCC38 | Abemaciclib | 6.14 | 0.83 | 120 | −4.64 | −4.71 | −4.54 |
| HCC38 | ABT-199 | 5.65 | 0.77 | 120 | −3.14 | −0.71 | 0.50 |
| HCC38 | ABT-263 | 37.11 | 0.13 | 145 | 27.10 | 22.24 | 20.66 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| HCC38 | BMN 673 | 20.73 | 0.09 | 115 | 12.68 | 14.90 | 13.43 |
| HCC38 | Carboplatin | 9.07 | 0.63 | 130 | 5.43 | 5.68 | 3.81 |
| HCC38 | Cisplatin | 6.47 | 0.60 | 115 | 8.46 | 3.08 | 2.06 |
| HCC38 | Docetaxel | 29.56 | 0.13 | 140 | 23.64 | 16.36 | 14.95 |
| HCC38 | Doxorubicin Hcl | 14.77 | 0.27 | 130 | 20.04 | 8.16 | 7.85 |
| HCC38 | Everolimus | 2.18 | 0.46 | 65 | −6.70 | −1.96 | −2.56 |
| HCC38 | Fulvestrant | 2.63 | 0.60 | 45 | −3.19 | −1.37 | −1.82 |
| HCC38 | GDC-0068 | 5.92 | 1.04 | 95 | 3.63 | 6.49 | 5.61 |
| HCC38 | Gemcitabine Hydrochloride | 14.50 | 0.51 | 165 | 21.72 | 8.18 | 6.75 |
| HCC38 | Lapatinib Ditosylate | 9.33 | 0.87 | 160 | 8.58 | 6.78 | 6.13 |
| HCC38 | LEE011 | 1.12 | 0.44 | 60 | −4.85 | −8.61 | −9.77 |
| HCC38 | Neratinib | 11.55 | 1.06 | 170 | 17.98 | 8.02 | 11.04 |
| HCC38 | Olaparib | 8.69 | 0.72 | 110 | 6.78 | 7.48 | 7.01 |
| HCC38 | Paclitaxel | 24.34 | 0.21 | 145 | 20.50 | 13.59 | 11.65 |
| HCC38 | PD-0332991 | 0.01 | 0.19 | 20 | −13.23 | −17.15 | −16.79 |
| HCC38 | Tamoxifen Citrate | 3.33 | 0.98 | 125 | 6.63 | 3.06 | 2.12 |
| HCC70 | A-1331852 | 173.58 | 0.00 | 180 | 73.73 | 74.12 | 74.78 |
| HCC70 | Abemaciclib | 18.15 | 0.92 | 180 | 10.18 | 6.99 | 8.33 |
| HCC70 | ABT-199 | 28.95 | 0.43 | 180 | 15.68 | 14.46 | 15.44 |
| HCC70 | ABT-263 | 97.06 | 0.03 | 180 | 44.63 | 44.49 | 44.97 |
| HCC70 | BMN 673 | 26.62 | 0.39 | 160 | 15.24 | 15.02 | 15.13 |
| HCC70 | Carboplatin | 7.72 | 0.31 | 60 | 12.67 | 3.84 | 3.02 |
| HCC70 | Cisplatin | 9.16 | 0.45 | 175 | 18.00 | 4.42 | 2.24 |
| HCC70 | Docetaxel | 39.82 | 0.14 | 180 | 25.33 | 22.90 | 20.81 |
| HCC70 | Doxorubicin Hcl | 18.12 | 0.34 | 125 | 21.36 | 11.58 | 10.35 |
| HCC70 | Everolimus | 11.30 | 0.64 | 120 | 9.56 | 8.83 | 6.84 |
| HCC70 | Fulvestrant | 17.18 | 0.68 | 160 | 10.34 | 9.70 | 10.67 |
| HCC70 | GDC-0068 | 27.63 | 0.30 | 180 | 19.29 | 14.42 | 13.10 |
| HCC70 | Gemcitabine Hydrochloride | 26.37 | 0.26 | 140 | 18.66 | 18.52 | 17.52 |
| HCC70 | Lapatinib Ditosylate | 25.42 | 0.35 | 170 | 17.29 | 14.60 | 13.28 |
| HCC70 | LEE011 | 6.12 | 0.93 | 95 | −0.15 | 0.16 | 0.49 |
| HCC70 | Neratinib | 42.47 | 0.09 | 155 | 36.07 | 21.70 | 21.51 |
| HCC70 | Olaparib | 12.18 | 0.94 | 130 | 6.93 | 6.07 | 6.54 |
| HCC70 | Paclitaxel | 31.20 | 0.14 | 165 | 20.09 | 17.61 | 15.72 |
| HCC70 | PD-0332991 | 8.66 | 0.68 | 95 | 4.80 | 3.64 | 4.83 |
| HCC70 | Tamoxifen Citrate | 5.37 | 0.50 | 40 | 8.94 | 2.32 | 0.77 |
| HDQ-P1 | A-1331852 | 132.76 | 0.01 | 85 | 58.35 | 61.13 | 60.82 |
| HDQ-P1 | Abemaciclib | 2.48 | 0.82 | 75 | −0.79 | −0.19 | 0.43 |
| HDQ-P1 | ABT-199 | 0.96 | 0.04 | 25 | 1.77 | 0.38 | 1.74 |
| HDQ-P1 | ABT-263 | 52.33 | 0.09 | 50 | 27.19 | 27.41 | 28.17 |
| HDQ-P1 | BMN 673 | 1.09 | 0.91 | 35 | 0.31 | −0.95 | −0.15 |
| HDQ-P1 | Carboplatin | 0.54 | 0.92 | 35 | −3.17 | −3.06 | −3.13 |
| HDQ-P1 | Cisplatin | 1.46 | 0.60 | 30 | 0.53 | −0.23 | 0.64 |
| HDQ-P1 | Docetaxel | 11.43 | 0.23 | 110 | 7.85 | 8.96 | 8.67 |
| HDQ-P1 | Doxorubicin Hcl | 3.52 | 1.48 | 130 | −0.97 | −1.23 | −0.68 |
| HDQ-P1 | Everolimus | 2.04 | 0.01 | 20 | 6.97 | −1.39 | 6.48 |
| HDQ-P1 | Fulvestrant | 0.42 | 0.00 | 20 | −5.92 | −6.15 | −5.56 |
| HDQ-P1 | GDC-0068 | 1.94 | 1.46 | 50 | −1.34 | −1.27 | −2.21 |
| HDQ-P1 | Gemcitabine Hydrochloride | 2.05 | 0.40 | 30 | −3.49 | −0.19 | 0.42 |
| HDQ-P1 | Lapatinib Ditosylate | 7.98 | 0.87 | 75 | 9.40 | 6.45 | 9.04 |
| HDQ-P1 | LEE011 | 0.15 | 0.04 | 20 | −2.80 | −6.22 | −9.02 |
| HDQ-P1 | Neratinib | 17.02 | 0.57 | 85 | 10.17 | 9.28 | 9.93 |
| HDQ-P1 | Olaparib | 1.22 | 0.51 | 25 | 3.81 | −0.38 | 3.65 |
| HDQ-P1 | Paclitaxel | 9.30 | 0.82 | 80 | 9.64 | 8.90 | 9.42 |
| HDQ-P1 | PD-0332991 | 0.17 | 0.36 | 20 | 0.47 | −6.53 | −11.86 |
| HDQ-P1 | Tamoxifen Citrate | 0.22 | 0.94 | 20 | −1.65 | −3.36 | −2.59 |
| HMC-1-8 | A-1331852 | 39.01 | 0.11 | 180 | 21.81 | 19.39 | 20.77 |
| HMC-1-8 | Abemaciclib | 24.23 | 0.30 | 180 | 24.27 | 13.46 | 13.14 |
| HMC-1-8 | ABT-199 | 9.51 | 0.90 | 145 | 6.70 | 5.15 | 6.08 |
| HMC-1-8 | ABT-263 | 21.09 | 0.20 | 180 | 13.21 | 10.36 | 11.80 |
| HMC-1-8 | BMN 673 | 19.54 | 0.22 | 180 | 22.38 | 11.38 | 11.09 |
| HMC-1-8 | Carboplatin | 9.60 | 0.72 | 155 | 9.25 | 4.09 | 3.94 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| HMC-1-8 | Cisplatin | 14.62 | 0.35 | 180 | 20.03 | 7.01 | 6.38 |
| HMC-1-8 | Docetaxel | 16.44 | 0.15 | 175 | 31.00 | 8.49 | 7.43 |
| HMC-1-8 | Doxorubicin Hcl | 13.53 | 0.18 | 180 | 32.10 | 7.22 | 6.68 |
| HMC-1-8 | Everolimus | 9.41 | 0.77 | 150 | 9.19 | 5.60 | 5.97 |
| HMC-1-8 | Fulvestrant | 13.30 | 0.63 | 150 | 10.58 | 7.21 | 7.81 |
| HMC-1-8 | GDC-0068 | 21.76 | 0.26 | 180 | 17.75 | 12.01 | 12.08 |
| HMC-1-8 | Gemcitabine Hydrochloride | 17.19 | 0.19 | 165 | 24.97 | 9.34 | 8.40 |
| HMC-1-8 | Lapatinib Ditosylate | 14.95 | 0.50 | 180 | 10.46 | 7.22 | 7.67 |
| HMC-1-8 | LEE011 | 9.01 | 0.81 | 155 | 9.82 | 5.13 | 5.78 |
| HMC-1-8 | Neratinib | 30.76 | 0.24 | 180 | 19.74 | 14.99 | 15.17 |
| HMC-1-8 | Olaparib | 10.86 | 0.78 | 140 | 10.54 | 5.78 | 6.22 |
| HMC-1-8 | Paclitaxel | 17.66 | 0.11 | 180 | 31.62 | 9.10 | 8.08 |
| HMC-1-8 | PD-0332991 | 12.76 | 0.47 | 165 | 13.91 | 7.82 | 8.09 |
| HMC-1-8 | Tamoxifen Citrate | 6.49 | 0.58 | 160 | 16.40 | 5.95 | 3.81 |
| JIMT-1 | A-1331852 | 126.70 | 0.01 | 75 | 57.07 | 57.74 | 57.21 |
| JIMT-1 | Abemaciclib | 1.34 | 1.23 | 110 | 1.74 | 1.30 | 1.54 |
| JIMT-1 | ABT-199 | 0.53 | 0.14 | 20 | −1.41 | −2.60 | −1.93 |
| JIMT-1 | ABT-263 | 19.55 | 0.18 | 20 | 18.71 | 12.60 | 14.35 |
| JIMT-1 | BMN 673 | 1.28 | 0.13 | 20 | −0.56 | −1.70 | −1.62 |
| JIMT-1 | Carboplatin | 0.69 | 0.96 | 25 | 3.78 | −0.17 | 1.92 |
| JIMT-1 | Cisplatin | 1.21 | 0.61 | 20 | 0.69 | −1.64 | −0.53 |
| JIMT-1 | Docetaxel | 6.23 | 0.71 | 80 | 4.03 | 4.64 | 3.81 |
| JIMT-1 | Doxorubicin Hcl | 4.98 | 1.05 | 100 | 2.41 | 0.73 | 1.97 |
| JIMT-1 | Everolimus | 1.56 | 0.23 | 30 | 5.29 | 2.41 | 1.96 |
| JIMT-1 | Fulvestrant | 1.26 | 0.11 | 20 | 5.80 | 0.54 | 4.52 |
| JIMT-1 | GDC-0068 | 1.19 | 0.26 | 20 | 2.76 | 1.18 | 1.53 |
| JIMT-1 | Gemcitabine Hydrochloride | 1.80 | 0.05 | 30 | 4.37 | 3.74 | 3.50 |
| JIMT-1 | Lapatinib Ditosylate | 3.49 | 0.29 | 50 | 2.54 | 1.96 | 2.82 |
| JIMT-1 | LEE011 | 0.28 | 0.00 | 20 | 0.29 | −2.46 | −4.06 |
| JIMT-1 | Neratinib | 17.62 | 0.18 | 175 | 10.52 | 11.00 | 11.11 |
| JIMT-1 | Olaparib | 0.61 | 0.59 | 25 | −1.42 | −0.34 | −1.35 |
| JIMT-1 | Paclitaxel | 7.65 | 0.50 | 100 | 3.72 | 4.19 | 4.00 |
| JIMT-1 | PD-0332991 | 0.48 | 0.01 | 20 | −2.69 | −2.73 | −2.74 |
| JIMT-1 | Tamoxifen Citrate | 0.64 | 0.38 | 20 | 0.23 | −2.28 | 0.10 |
| KPL-1 | A-1331852 | 36.44 | 0.03 | 105 | 26.84 | 25.88 | 26.65 |
| KPL-1 | Abemaciclib | 1.28 | 0.77 | 110 | −3.02 | −1.63 | −2.87 |
| KPL-1 | ABT-199 | 3.31 | 1.23 | 45 | −1.15 | −2.69 | −0.11 |
| KPL-1 | ABT-263 | 13.50 | 0.14 | 100 | 9.39 | 9.18 | 9.39 |
| KPL-1 | BMN 673 | 1.84 | 0.53 | 50 | −2.58 | 0.29 | 0.06 |
| KPL-1 | Carboplatin | 2.66 | 0.89 | 105 | 0.04 | 1.33 | 0.65 |
| KPL-1 | Cisplatin | 4.51 | 0.76 | 110 | −0.41 | 0.95 | 0.45 |
| KPL-1 | Docetaxel | 10.20 | 0.49 | 110 | 5.18 | 8.06 | 7.67 |
| KPL-1 | Doxorubicin Hcl | 5.09 | 0.27 | 100 | −0.58 | −1.11 | −0.82 |
| KPL-1 | Everolimus | 6.00 | 0.45 | 95 | 2.85 | 5.14 | 4.93 |
| KPL-1 | Fulvestrant | 2.75 | 0.75 | 110 | 0.30 | 1.12 | 1.04 |
| KPL-1 | GDC-0068 | 10.58 | 0.15 | 100 | 6.29 | 8.36 | 7.30 |
| KPL-1 | Gemcitabine Hydrochloride | 3.05 | 0.39 | 75 | −0.16 | 2.32 | 2.03 |
| KPL-1 | Lapatinib Ditosylate | 7.99 | 0.65 | 120 | 2.56 | 2.45 | 1.74 |
| KPL-1 | LEE011 | 1.43 | 0.65 | 25 | 0.36 | −0.31 | 0.24 |
| KPL-1 | Neratinib | 9.97 | 0.55 | 180 | 9.37 | 2.11 | 2.47 |
| KPL-1 | Olaparib | 2.49 | 0.50 | 65 | 0.48 | 1.49 | 1.44 |
| KPL-1 | Paclitaxel | 6.00 | 0.32 | 100 | 3.22 | 5.73 | 4.40 |
| KPL-1 | PD-0332991 | 1.39 | 0.18 | 35 | −3.50 | −2.01 | −2.32 |
| KPL-1 | Tamoxifen Citrate | 2.78 | 0.54 | 40 | 7.91 | 1.91 | 2.83 |
| MCF7 | A-1331852 | 40.75 | 0.02 | 140 | 25.26 | 25.62 | 25.95 |
| MCF7 | Abemaciclib | 8.46 | 1.06 | 165 | 4.62 | 4.76 | 3.74 |
| MCF7 | ABT-199 | 1.43 | 1.10 | 80 | 0.64 | −0.19 | −0.54 |
| MCF7 | ABT-263 | 13.72 | 0.22 | 125 | 8.32 | 8.72 | 8.25 |
| MCF7 | BMN 673 | 14.01 | 0.29 | 100 | 10.82 | 11.85 | 11.69 |
| MCF7 | Carboplatin | 6.10 | 0.40 | 75 | 8.40 | 5.66 | 4.40 |
| MCF7 | Cisplatin | 6.98 | 0.45 | 150 | 11.15 | 4.64 | 3.51 |
| MCF7 | Docetaxel | 17.93 | 0.26 | 145 | 14.35 | 11.99 | 11.64 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| MCF7 | Doxorubicin Hcl | 9.78 | 0.52 | 65 | 13.22 | 5.75 | 5.43 |
| MCF7 | Everolimus | 9.72 | 0.33 | 105 | 6.88 | 7.73 | 6.93 |
| MCF7 | Fulvestrant | 15.23 | 0.60 | 130 | 11.46 | 11.54 | 11.41 |
| MCF7 | GDC-0068 | 19.76 | 0.13 | 150 | 15.15 | 12.23 | 11.29 |
| MCF7 | Gemcitabine Hydrochloride | 11.61 | 0.18 | 110 | 8.58 | 8.28 | 8.26 |
| MCF7 | Lapatinib Ditosylate | 16.16 | 0.34 | 155 | 12.56 | 9.97 | 8.60 |
| MCF7 | LEE011 | 2.78 | 0.49 | 75 | 0.50 | 0.31 | 0.36 |
| MCF7 | Neratinib | 13.05 | 0.44 | 175 | 20.28 | 8.47 | 8.60 |
| MCF7 | Olaparib | 4.43 | 0.65 | 85 | 3.44 | 2.89 | 3.34 |
| MCF7 | Paclitaxel | 12.79 | 0.32 | 90 | 12.91 | 10.02 | 8.74 |
| MCF7 | PD-0332991 | 2.42 | 0.74 | 40 | −3.21 | −2.51 | −2.27 |
| MCF7 | Tamoxifen Citrate | 4.12 | 0.41 | 35 | 9.82 | 2.71 | 3.29 |
| MDA-MB-175-VII | A-1331852 | 151.19 | 0.01 | 180 | 69.57 | 66.81 | 64.96 |
| MDA-MB-175-VII | Abemaciclib | 7.13 | 0.43 | 70 | 10.19 | 1.17 | 6.90 |
| MDA-MB-175-VII | ABT-199 | 10.85 | 0.80 | 100 | 12.15 | 6.27 | 11.70 |
| MDA-MB-175-VII | ABT-263 | 87.79 | 0.11 | 175 | 44.52 | 40.81 | 43.73 |
| MDA-MB-175-VII | BMN 673 | 10.05 | 0.24 | 80 | 12.96 | 7.86 | 10.40 |
| MDA-MB-175-VII | Carboplatin | 9.73 | 0.60 | 80 | 15.45 | 7.97 | 12.14 |
| MDA-MB-175-VII | Cisplatin | 4.03 | 0.49 | 60 | 9.70 | −1.47 | 2.49 |
| MDA-MB-175-VII | Docetaxel | 15.31 | 0.50 | 50 | 16.97 | 10.22 | 12.14 |
| MDA-MB-175-VII | Doxorubicin Hcl | 10.14 | 0.29 | 40 | 12.79 | 2.91 | 4.89 |
| MDA-MB-175-VII | Everolimus | 10.26 | 0.84 | 55 | 9.10 | 4.72 | 4.62 |
| MDA-MB-175-VII | Fulvestrant | 7.62 | 1.21 | 140 | 11.56 | 1.65 | 10.58 |
| MDA-MB-175-VII | GDC-0068 | 12.46 | 0.40 | 80 | 14.86 | 9.10 | 8.45 |
| MDA-MB-175-VII | Gemcitabine Hydrochloride | 10.44 | 0.18 | 30 | 14.01 | 3.16 | 4.30 |
| MDA-MB-175-VII | Lapatinib Ditosylate | 10.79 | 0.32 | 55 | 21.28 | 7.26 | 4.84 |
| MDA-MB-175-VII | LEE011 | 5.95 | 0.12 | 50 | 1.46 | −7.43 | 0.70 |
| MDA-MB-175-VII | Neratinib | 11.07 | 0.64 | 85 | 18.28 | 8.80 | 7.95 |
| MDA-MB-175-VII | Olaparib | 6.22 | 0.83 | 55 | 10.94 | 6.31 | 10.32 |
| MDA-MB-175-VII | Paclitaxel | 18.38 | 0.13 | 120 | 14.12 | 9.64 | 10.16 |
| MDA-MB-175-VII | PD-0332991 | 8.13 | 1.01 | 65 | 9.82 | −1.59 | 8.08 |
| MDA-MB-175-VII | Tamoxifen Citrate | 4.62 | 0.36 | 50 | 11.95 | 2.09 | 6.27 |
| MDA-MB-231 | A-1331852 | 84.95 | 0.01 | 180 | 38.81 | 37.61 | 37.35 |
| MDA-MB-231 | Abemaciclib | 15.52 | 0.24 | 90 | 5.49 | 8.28 | 7.26 |
| MDA-MB-231 | ABT-199 | 1.75 | 0.73 | 45 | 0.79 | 0.26 | 2.67 |
| MDA-MB-231 | ABT-263 | 50.86 | 0.14 | 160 | 27.51 | 25.23 | 27.27 |
| MDA-MB-231 | BMN 673 | 5.59 | 0.03 | 40 | 5.73 | 8.77 | 8.65 |
| MDA-MB-231 | Carboplatin | 1.89 | 0.91 | 50 | 3.11 | 2.11 | 3.30 |
| MDA-MB-231 | Cisplatin | 4.48 | 0.34 | 70 | 5.98 | 4.74 | 6.47 |
| MDA-MB-231 | Docetaxel | 11.57 | 0.14 | 90 | 5.15 | 7.49 | 6.89 |
| MDA-MB-231 | Doxorubicin Hcl | 6.52 | 0.30 | 55 | 4.81 | 3.10 | 4.23 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| MDA-MB-231 | Everolimus | 2.06 | 0.99 | 30 | 0.30 | 2.64 | 3.33 |
| MDA-MB-231 | Fulvestrant | 1.17 | 0.88 | 45 | 1.26 | −0.76 | 1.50 |
| MDA-MB-231 | GDC-0068 | 2.30 | 0.55 | 40 | 4.95 | 2.34 | 5.29 |
| MDA-MB-231 | Gemcitabine Hydrochloride | 9.99 | 0.42 | 65 | 9.60 | 9.39 | 10.28 |
| MDA-MB-231 | Lapatinib Ditosylate | 2.98 | 0.77 | 85 | 4.49 | 2.62 | 4.10 |
| MDA-MB-231 | LEE011 | 1.62 | 0.58 | 35 | −2.91 | 0.54 | 0.24 |
| MDA-MB-231 | Neratinib | 4.59 | 1.06 | 100 | 6.82 | 2.87 | 5.05 |
| MDA-MB-231 | Olaparib | 2.48 | 0.74 | 45 | 5.54 | 3.02 | 5.23 |
| MDA-MB-231 | Paclitaxel | 10.67 | 0.33 | 95 | 6.86 | 7.50 | 7.27 |
| MDA-MB-231 | PD-0332991 | 1.48 | 0.75 | 50 | −2.68 | 2.04 | 1.10 |
| MDA-MB-231 | Tamoxifen Citrate | 2.13 | 1.06 | 80 | 4.73 | 0.79 | 4.38 |
| MDA-MB-361 | A-1331852 | 71.10 | 0.04 | 140 | 34.44 | 32.54 | 32.83 |
| MDA-MB-361 | Abemaciclib | 0.59 | 1.06 | 30 | −11.97 | −13.22 | −11.93 |
| MDA-MB-361 | ABT-199 | 2.05 | 0.99 | 25 | −0.07 | −2.07 | −1.96 |
| MDA-MB-361 | ABT-263 | 22.56 | 0.40 | 135 | 11.97 | 11.78 | 12.68 |
| MDA-MB-361 | BMN 673 | 2.49 | 0.85 | 70 | −0.43 | −1.67 | −0.12 |
| MDA-MB-361 | Carboplatin | 7.41 | 0.82 | 135 | 2.52 | 1.01 | 1.40 |
| MDA-MB-361 | Cisplatin | 3.36 | 0.81 | 165 | 3.24 | −1.91 | −2.31 |
| MDA-MB-361 | Docetaxel | 4.61 | 0.35 | 125 | −0.86 | −2.31 | −3.71 |
| MDA-MB-361 | Doxorubicin Hcl | 3.75 | 0.48 | 150 | 2.69 | −1.72 | −3.11 |
| MDA-MB-361 | Everolimus | 8.70 | 0.42 | 135 | 5.72 | 4.93 | 3.91 |
| MDA-MB-361 | Fulvestrant | 3.34 | 0.93 | 50 | −3.29 | −1.23 | −0.47 |
| MDA-MB-361 | GDC-0068 | 14.81 | 0.15 | 160 | 11.41 | 7.13 | 5.39 |
| MDA-MB-361 | Gemcitabine Hydrochloride | 4.94 | 0.64 | 100 | −0.94 | −0.78 | 0.09 |
| MDA-MB-361 | Lapatinib Ditosylate | 7.87 | 0.87 | 135 | 3.24 | 4.28 | 2.77 |
| MDA-MB-361 | LEE011 | 2.03 | 0.39 | 50 | −4.99 | −7.47 | −5.93 |
| MDA-MB-361 | Neratinib | 10.96 | 0.18 | 100 | 8.05 | 9.22 | 8.69 |
| MDA-MB-361 | Olaparib | 1.87 | 0.85 | 35 | −4.71 | −4.15 | −3.25 |
| MDA-MB-361 | Paclitaxel | 7.33 | 0.50 | 40 | 5.85 | 1.78 | 3.40 |
| MDA-MB-361 | PD-0332991 | 3.26 | 0.25 | 55 | −5.98 | −6.08 | −4.81 |
| MDA-MB-361 | Tamoxifen Citrate | 4.20 | 0.48 | 50 | 1.45 | −2.46 | 0.13 |
| MDA-MB-436 | A-1331852 | 34.98 | 0.03 | 85 | 31.88 | 29.49 | 32.20 |
| MDA-MB-436 | Abemaciclib | 2.06 | 0.78 | 30 | 0.64 | −1.15 | −0.06 |
| MDA-MB-436 | ABT-199 | 2.99 | 1.08 | 60 | 5.30 | 2.17 | 5.33 |
| MDA-MB-436 | ABT-263 | 15.15 | 0.14 | 85 | 15.60 | 12.44 | 15.52 |
| MDA-MB-436 | BMN 673 | 4.30 | 1.04 | 85 | 1.92 | 4.93 | 4.15 |
| MDA-MB-436 | Carboplatin | 2.53 | 1.72 | 135 | 1.31 | 1.06 | 1.16 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| MDA-MB-436 | Cisplatin | 2.45 | 1.18 | 120 | 2.08 | 1.62 | 1.58 |
| MDA-MB-436 | Docetaxel | 1.52 | 0.58 | 30 | 1.49 | 1.67 | 1.48 |
| MDA-MB-436 | Doxorubicin Hcl | 2.79 | 0.38 | 95 | −0.34 | 1.81 | 1.09 |
| MDA-MB-436 | Everolimus | 2.25 | 0.26 | 35 | 2.45 | 4.01 | 3.66 |
| MDA-MB-436 | Fulvestrant | 3.30 | 0.48 | 35 | 1.52 | 2.87 | 2.94 |
| MDA-MB-436 | GDC-0068 | 4.55 | 0.88 | 90 | 1.35 | 4.48 | 4.23 |
| MDA-MB-436 | Gemcitabine Hydrochloride | 1.02 | 0.58 | 20 | −1.38 | −0.39 | −0.49 |
| MDA-MB-436 | Lapatinib Ditosylate | 3.30 | 0.51 | 80 | 1.32 | 0.02 | 1.15 |
| MDA-MB-436 | LEE011 | 2.00 | 0.89 | 25 | 0.22 | −1.01 | 0.11 |
| MDA-MB-436 | Neratinib | 4.11 | 0.26 | 40 | 5.24 | −0.69 | 0.79 |
| MDA-MB-436 | Olaparib | 3.26 | 0.43 | 30 | 6.22 | 5.77 | 6.71 |
| MDA-MB-436 | Paclitaxel | 3.82 | 0.68 | 30 | 4.24 | 4.96 | 4.31 |
| MDA-MB-436 | PD-0332991 | 1.03 | 0.94 | 25 | −0.95 | −2.05 | 0.16 |
| MDA-MB-436 | Tamoxifen Citrate | 1.41 | 0.30 | 30 | 4.56 | 0.00 | 1.78 |
| MDA-MB-453 | A-1331852 | 128.51 | 0.01 | 180 | 57.57 | 56.79 | 56.98 |
| MDA-MB-453 | Abemaciclib | 8.76 | 1.15 | 135 | 4.24 | 2.64 | 0.75 |
| MDA-MB-453 | ABT-199 | 10.47 | 0.95 | 140 | 6.86 | 3.17 | 5.22 |
| MDA-MB-453 | ABT-263 | 58.72 | 0.04 | 180 | 27.88 | 26.73 | 27.44 |
| MDA-MB-453 | BMN 673 | 29.35 | 0.44 | 165 | 20.23 | 19.38 | 18.41 |
| MDA-MB-453 | Carboplatin | 10.04 | 1.12 | 150 | 9.75 | 5.44 | 6.37 |
| MDA-MB-453 | Cisplatin | 9.66 | 0.34 | 70 | 13.82 | 4.06 | 4.70 |
| MDA-MB-453 | Docetaxel | 44.90 | 0.03 | 175 | 30.81 | 22.87 | 21.87 |
| MDA-MB-453 | Doxorubicin Hcl | 10.21 | 0.23 | 50 | 21.74 | 5.47 | 4.39 |
| MDA-MB-453 | Everolimus | 5.75 | 1.06 | 115 | 3.87 | 0.04 | −0.98 |
| MDA-MB-453 | Fulvestrant | 4.79 | 0.95 | 75 | −0.77 | −3.96 | −1.85 |
| MDA-MB-453 | GDC-0068 | 6.04 | 0.78 | 50 | 6.63 | −1.13 | −0.82 |
| MDA-MB-453 | Gemcitabine Hydrochloride | 20.56 | 0.41 | 150 | 16.80 | 12.68 | 12.53 |
| MDA-MB-453 | Lapatinib Ditosylate | 13.89 | 0.45 | 180 | 15.41 | 7.33 | 5.38 |
| MDA-MB-453 | LEE011 | 5.21 | 0.45 | 85 | 0.42 | −1.86 | −1.45 |
| MDA-MB-453 | Neratinib | 16.63 | 0.35 | 80 | 19.67 | 10.24 | 8.51 |
| MDA-MB-453 | Olaparib | 10.79 | 0.58 | 110 | 7.22 | 5.85 | 5.82 |
| MDA-MB-453 | Paclitaxel | 41.82 | 0.07 | 180 | 29.92 | 20.75 | 20.54 |
| MDA-MB-453 | PD-0332991 | 6.98 | 1.08 | 100 | 2.50 | 1.27 | −0.53 |
| MDA-MB-453 | Tamoxifen Citrate | 6.85 | 0.45 | 45 | 13.38 | 1.53 | 3.01 |
| MDA-MB-468 | A-1331852 | 83.51 | 0.02 | 180 | 44.88 | 40.75 | 39.58 |
| MDA-MB-468 | Abemaciclib | 6.06 | 0.62 | 175 | 15.71 | 0.40 | −0.05 |
| MDA-MB-468 | ABT-199 | 12.47 | 0.64 | 135 | 7.63 | 6.49 | 8.34 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| MDA-MB-468 | ABT-263 | 42.71 | 0.10 | 180 | 24.89 | 23.11 | 22.29 |
| MDA-MB-468 | BMN 673 | 24.75 | 0.21 | 165 | 20.96 | 16.43 | 15.68 |
| MDA-MB-468 | Carboplatin | 7.68 | 0.56 | 135 | 19.05 | 4.48 | 3.36 |
| MDA-MB-468 | Cisplatin | 8.65 | 0.53 | 105 | 27.91 | 5.89 | 4.42 |
| MDA-MB-468 | Docetaxel | 20.73 | 0.08 | 165 | 28.07 | 11.28 | 10.11 |
| MDA-MB-468 | Doxorubicin Hcl | 8.76 | 0.51 | 70 | 27.73 | 6.61 | 4.84 |
| MDA-MB-468 | Everolimus | 15.60 | 0.35 | 145 | 11.63 | 9.14 | 7.97 |
| MDA-MB-468 | Fulvestrant | 14.13 | 0.57 | 150 | 6.94 | 6.17 | 7.22 |
| MDA-MB-468 | GDC-0068 | 35.74 | 0.16 | 170 | 22.06 | 20.01 | 18.96 |
| MDA-MB-468 | Gemcitabine Hydrochloride | 13.66 | 0.31 | 65 | 18.82 | 8.33 | 6.65 |
| MDA-MB-468 | Lapatinib Ditosylate | 12.66 | 0.36 | 180 | 16.38 | 7.88 | 6.42 |
| MDA-MB-468 | LEE011 | 9.17 | 0.25 | 75 | 5.67 | 6.14 | 6.67 |
| MDA-MB-468 | Neratinib | 19.05 | 0.18 | 165 | 34.71 | 11.03 | 9.11 |
| MDA-MB-468 | Olaparib | 14.61 | 0.51 | 150 | 13.61 | 10.77 | 11.92 |
| MDA-MB-468 | Paclitaxel | 20.07 | 0.27 | 145 | 24.80 | 12.02 | 10.67 |
| MDA-MB-468 | PD-0332991 | 8.69 | 0.84 | 150 | 7.72 | 6.49 | 5.45 |
| MDA-MB-468 | Tamoxifen Citrate | 9.07 | 0.61 | 175 | 15.81 | 6.82 | 5.97 |
| SK-BR-3 | A-1331852 | 42.86 | 0.07 | 165 | 23.56 | 22.70 | 23.17 |
| SK-BR-3 | Abemaciclib | 7.71 | 0.62 | 160 | 5.11 | 2.53 | 1.04 |
| SK-BR-3 | ABT-199 | 5.72 | 0.92 | 150 | 4.43 | 3.31 | 4.22 |
| SK-BR-3 | ABT-263 | 20.50 | 0.26 | 150 | 10.74 | 9.87 | 10.64 |
| SK-BR-3 | BMN 673 | 8.10 | 0.67 | 105 | 8.68 | 5.38 | 5.03 |
| SK-BR-3 | Carboplatin | 6.87 | 0.35 | 160 | 11.97 | 1.74 | 1.40 |
| SK-BR-3 | Cisplatin | 10.90 | 0.14 | 150 | 19.53 | 6.00 | 5.11 |
| SK-BR-3 | Docetaxel | 7.33 | 0.32 | 155 | 14.70 | 4.18 | 2.95 |
| SK-BR-3 | Doxorubicin Hcl | 10.51 | 0.16 | 160 | 19.25 | 6.65 | 5.23 |
| SK-BR-3 | Everolimus | 4.58 | 0.76 | 125 | 7.76 | 3.46 | 2.55 |
| SK-BR-3 | Fulvestrant | 2.05 | 1.06 | 20 | −2.14 | −3.78 | −2.67 |
| SK-BR-3 | GDC-0068 | 3.48 | 1.32 | 140 | 5.66 | 1.15 | 0.35 |
| SK-BR-3 | Gemcitabine Hydrochloride | 17.69 | 0.11 | 165 | 15.51 | 10.65 | 9.24 |
| SK-BR-3 | Lapatinib Ditosylate | 20.30 | 0.15 | 160 | 21.22 | 11.46 | 9.48 |
| SK-BR-3 | LEE011 | 1.72 | 0.68 | 45 | −2.93 | −3.37 | −3.50 |
| SK-BR-3 | Neratinib | 22.77 | 0.12 | 180 | 28.46 | 11.39 | 11.10 |
| SK-BR-3 | Olaparib | 2.89 | 1.26 | 130 | 3.67 | 0.39 | 2.20 |
| SK-BR-3 | Paclitaxel | 6.10 | 0.70 | 110 | 16.38 | 4.37 | 2.51 |
| SK-BR-3 | PD-0332991 | 1.28 | 1.54 | 135 | −2.33 | −5.69 | −5.46 |
| SK-BR-3 | Tamoxifen Citrate | 3.84 | 0.66 | 20 | 9.91 | 1.15 | 0.42 |
| SUM159PT | A-1331852 | 222.82 | 0.00 | 90 | 97.01 | 95.02 | 97.01 |
| SUM159PT | Abemaciclib | 9.35 | 0.51 | 180 | 5.06 | 2.12 | 3.04 |
| SUM159PT | ABT-199 | 15.16 | 0.56 | 85 | 13.19 | 9.29 | 12.24 |
| SUM159PT | ABT-263 | 124.52 | 0.03 | 90 | 57.91 | 55.55 | 57.69 |
| SUM159PT | BMN 673 | 1.99 | 0.90 | 90 | 1.75 | 1.20 | 1.38 |
| SUM159PT | Carboplatin | 0.81 | 0.52 | 20 | 1.33 | −1.99 | −0.01 |
| SUM159PT | Cisplatin | 0.41 | 0.79 | 20 | −1.91 | −4.36 | −4.20 |
| SUM159PT | Docetaxel | 33.03 | 0.22 | 95 | 18.66 | 18.88 | 17.94 |
| SUM159PT | Doxorubicin Hcl | 12.91 | 0.28 | 165 | 9.26 | 7.46 | 6.92 |
| SUM159PT | Everolimus | 1.12 | 0.62 | 20 | 0.61 | 1.27 | 0.66 |
| SUM159PT | Fulvestrant | 1.23 | 1.32 | 65 | 2.51 | 0.14 | 2.16 |
| SUM159PT | GDC-0068 | 2.15 | 0.96 | 90 | 1.86 | 1.02 | 1.50 |
| SUM159PT | Gemcitabine Hydrochloride | 22.96 | 0.41 | 115 | 12.69 | 11.94 | 10.95 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| SUM159PT | Lapatinib Ditosylate | 5.14 | 1.37 | 145 | 9.56 | 2.82 | 7.11 |
| SUM159PT | LEE011 | 0.85 | 1.27 | 50 | 2.23 | 0.11 | 1.98 |
| SUM159PT | Neratinib | 22.98 | 0.17 | 180 | 15.93 | 11.51 | 12.90 |
| SUM159PT | Olaparib | 1.75 | 1.56 | 75 | 4.11 | 1.77 | 4.00 |
| SUM159PT | Paclitaxel | 30.74 | 0.06 | 115 | 17.49 | 16.62 | 16.31 |
| SUM159PT | PD-0332991 | 1.23 | 0.52 | 20 | 1.41 | 1.84 | 1.45 |
| SUM159PT | Tamoxifen Citrate | 1.32 | 0.20 | 20 | 4.38 | 1.32 | 1.56 |
| T47D | A-1331852 | 101.21 | 0.03 | 85 | 43.55 | 43.58 | 44.81 |
| T47D | Abemaciclib | 1.95 | 0.37 | 45 | −3.69 | −0.69 | −1.28 |
| T47D | ABT-199 | 1.56 | 0.89 | 80 | −3.22 | −3.46 | −1.94 |
| T47D | ABT-263 | 16.87 | 0.44 | 70 | 7.32 | 3.47 | 7.08 |
| T47D | BMN 673 | 2.58 | 0.62 | 70 | 0.61 | 1.26 | 1.88 |
| T47D | Carboplatin | 1.42 | 1.01 | 30 | 0.78 | −1.67 | 0.98 |
| T47D | Cisplatin | 3.05 | 0.79 | 80 | −0.02 | 0.03 | 0.73 |
| T47D | Docetaxel | 6.53 | 0.18 | 90 | −1.55 | 2.30 | 1.76 |
| T47D | Doxorubicin Hcl | 10.31 | 0.70 | 125 | 4.37 | 3.89 | 4.94 |
| T47D | Everolimus | 3.70 | 0.34 | 75 | −0.21 | 2.87 | 2.69 |
| T47D | Fulvestrant | 4.16 | 0.31 | 55 | 0.17 | 2.12 | 3.30 |
| T47D | GDC-0068 | 2.92 | 0.54 | 95 | 2.03 | 3.77 | 2.65 |
| T47D | Gemcitabine Hydrochloride | 1.93 | 0.70 | 80 | 0.61 | 0.03 | 0.69 |
| T47D | Lapatinib Ditosylate | 5.13 | 0.41 | 65 | 2.29 | 5.53 | 5.20 |
| T47D | LEE011 | 2.59 | 0.25 | 30 | 4.75 | 4.16 | 5.07 |
| T47D | Neratinib | 11.73 | 0.40 | 180 | 7.67 | 2.55 | 5.95 |
| T47D | Olaparib | 2.41 | 0.84 | 70 | 1.98 | 0.34 | 2.18 |
| T47D | Paclitaxel | 7.08 | 0.08 | 80 | 5.97 | 5.65 | 6.40 |
| T47D | PD-0332991 | 3.09 | 0.56 | 65 | −2.26 | 3.46 | 2.50 |
| T47D | Tamoxifen Citrate | 3.00 | 0.42 | 45 | 7.48 | −0.47 | 5.38 |
| ZR-75-1 | A-1331852 | 161.11 | 0.01 | 105 | 71.14 | 70.80 | 72.60 |
| ZR-75-1 | Abemaciclib | 4.36 | 0.82 | 105 | 3.01 | 5.62 | 4.85 |
| ZR-75-1 | ABT-199 | 23.55 | 0.38 | 105 | 16.30 | 14.84 | 17.02 |
| ZR-75-1 | ABT-263 | 90.09 | 0.05 | 90 | 48.65 | 42.73 | 47.17 |
| ZR-75-1 | BMN 673 | 5.18 | 0.85 | 100 | 4.21 | 5.00 | 5.86 |
| ZR-75-1 | Carboplatin | 7.91 | 0.88 | 100 | 4.99 | 6.14 | 6.57 |
| ZR-75-1 | Cisplatin | 12.40 | 0.88 | 155 | 9.45 | 7.38 | 8.42 |
| ZR-75-1 | Docetaxel | 25.42 | 0.13 | 115 | 16.15 | 16.66 | 17.29 |
| ZR-75-1 | Doxorubicin Hcl | 11.38 | 0.37 | 170 | 9.07 | 6.64 | 6.44 |
| ZR-75-1 | Everolimus | 5.68 | 0.79 | 110 | 3.52 | 5.12 | 4.67 |
| ZR-75-1 | Fulvestrant | 4.22 | 0.72 | 95 | 5.80 | 4.00 | 6.17 |
| ZR-75-1 | GDC-0068 | 22.00 | 0.15 | 130 | 11.51 | 11.77 | 11.34 |
| ZR-75-1 | Gemcitabine Hydrochloride | 25.70 | 0.04 | 100 | 15.92 | 18.68 | 18.63 |
| ZR-75-1 | Lapatinib Ditosylate | 8.41 | 0.73 | 95 | 3.60 | 4.21 | 4.72 |
| ZR-75-1 | LEE011 | 1.55 | 0.57 | 25 | 1.95 | 1.27 | 2.41 |
| ZR-75-1 | Neratinib | 10.39 | 0.86 | 140 | 13.55 | 6.49 | 7.51 |
| ZR-75-1 | Olaparib | 3.14 | 0.97 | 50 | 4.08 | 2.51 | 4.47 |
| ZR-75-1 | Paclitaxel | 23.41 | 0.07 | 100 | 11.25 | 13.75 | 12.91 |
| ZR-75-1 | PD-0332991 | 1.76 | 0.39 | 40 | 0.17 | 2.00 | 1.74 |
| ZR-75-1 | Tamoxifen Citrate | 3.29 | 0.99 | 120 | 4.69 | 0.35 | 1.26 |
| ZR-75-30 | A-1331852 | 134.95 | 0.01 | 130 | 63.14 | 64.00 | 65.08 |
| ZR-75-30 | Abemaciclib | 19.88 | 0.42 | 135 | 2.74 | 3.90 | 4.55 |
| ZR-75-30 | ABT-199 | 28.05 | 0.03 | 125 | 15.29 | 15.23 | 15.50 |
| ZR-75-30 | ABT-263 | 69.59 | 0.04 | 135 | 38.04 | 36.45 | 37.00 |
| ZR-75-30 | BMN 673 | 13.36 | 0.18 | 125 | 7.67 | 8.07 | 8.54 |
| ZR-75-30 | Carboplatin | 12.96 | 0.30 | 100 | 8.34 | 6.81 | 5.78 |
| ZR-75-30 | Cisplatin | 16.44 | 0.24 | 95 | 14.77 | 8.48 | 9.66 |
| ZR-75-30 | Docetaxel | 8.08 | 0.52 | 130 | 6.48 | 3.70 | 2.62 |
| ZR-75-30 | Doxorubicin Hcl | 12.54 | 0.16 | 95 | 10.86 | 8.97 | 7.91 |
| ZR-75-30 | Everolimus | 7.22 | 0.61 | 110 | 3.82 | 4.76 | 4.25 |
| ZR-75-30 | Fulvestrant | 4.50 | 0.54 | 65 | 1.91 | 1.18 | 1.80 |
| ZR-75-30 | GDC-0068 | 25.94 | 0.08 | 120 | 11.88 | 12.52 | 12.03 |
| ZR-75-30 | Gemcitabine Hydrochloride | 20.25 | 0.05 | 110 | 10.07 | 11.89 | 12.53 |
| ZR-75-30 | Lapatinib Ditosylate | 34.14 | 0.31 | 100 | 30.36 | 19.58 | 16.94 |

TABLE 21-continued

In vitro combination testing results

| Cell Line | Compound A × | Synergy Score | Best CI | Best CI Level | Bliss Volume | HSA volume | Loewe Volume |
|---|---|---|---|---|---|---|---|
| ZR-75-30 | LEE011 | 3.12 | 0.24 | 60 | −2.99 | −3.04 | −1.24 |
| ZR-75-30 | Neratinib | 30.49 | 0.41 | 110 | 32.84 | 16.20 | 14.61 |
| ZR-75-30 | Olaparib | 9.05 | 0.43 | 115 | 6.70 | 5.47 | 6.57 |
| ZR-75-30 | Paclitaxel | 8.63 | 0.41 | 120 | 5.07 | 3.33 | 2.47 |
| ZR-75-30 | PD-0332991 | 10.28 | 0.62 | 130 | 6.01 | 3.40 | 3.98 |
| ZR-75-30 | Tamoxifen Citrate | 1.30 | 1.00 | 55 | −0.33 | −6.28 | −8.68 |

Example 4

The combination potential of compound A with BTK inhibitors was tested in a panel of haematalogical cancer cell lines using a 72-hour in vitro proliferation assays. Results of combination testing are shown in Table 22.

TABLE 22

In vitro combination testing results

| Cell Line | Compound A × | Synergy Score | Best CI | Best CI Level | HSA Volume | Bliss Volume | Loewe Volume |
|---|---|---|---|---|---|---|---|
| HBL-1 | Acalabrutinib | 7.28 | 0.09 | 55 | 9.39 | 4.86 | 9.09 |
| HBL-1 | Tirabrutinib | 7.02 | 0.06 | 60 | 8.94 | 3.09 | 8.17 |
| HBL-1 | PCI-32765 | 6.94 | 0.09 | 55 | 9.06 | 4.85 | 8.78 |
| HBL-1 | Zanubrutinib | 8.18 | 0.05 | 55 | 10.34 | 5.13 | 9.75 |
| OCI-Ly10 | Acalabrutinib | 1.59 | 0.69 | 80 | 0.62 | −1.82 | −0.84 |
| OCI-Ly10 | Tirabrutinib | 2.72 | 0.63 | 80 | 3.22 | 0.21 | 1.63 |
| OCI-Ly10 | PCI-32765 | 3.36 | 0.60 | 80 | 3.18 | 0.61 | 2.26 |
| OCI-Ly10 | Zanubrutinib | 4.04 | 0.50 | 80 | 3.82 | 1.36 | 3.55 |
| SU-DHL-2 | Acalabrutinib | 1.76 | 0.39 | 20 | 1.30 | 1.10 | 2.29 |
| SU-DHL-2 | Tirabrutinib | 0.98 | 0.42 | 20 | −0.97 | 0.39 | 1.23 |
| SU-DHL-2 | PCI-32765 | 1.21 | 0.51 | 30 | 1.32 | 1.98 | 2.33 |
| SU-DHL-2 | Zanubrutinib | 0.72 | 0.86 | 40 | 0.63 | 1.42 | 1.23 |
| SU-DHL-4 | Acalabrutinib | 1.02 | 0.90 | 80 | −3.54 | 0.66 | −2.10 |
| SU-DHL-4 | Tirabrutinib | 1.10 | 0.84 | 20 | −2.97 | 1.52 | −0.81 |
| SU-DHL-4 | PCI-32765 | 0.34 | 0.96 | 20 | −3.44 | −2.02 | −2.13 |
| SU-DHL-4 | Zanubrutinib | 0.76 | 1.06 | 20 | −4.15 | 0.06 | −4.24 |
| SU-DHL-8 | Acalabrutinib | 0.52 | 0.79 | 20 | −5.31 | 3.28 | −3.08 |
| SU-DHL-8 | Tirabrutinib | 0.60 | 0.45 | 20 | −6.01 | 4.13 | −3.72 |
| SU-DHL-8 | PCI-32765 | 0.90 | 0.39 | 20 | −1.62 | 0.57 | 0.54 |
| SU-DHL-8 | Zanubrutinib | 0.66 | 0.52 | 30 | −5.32 | −5.98 | −5.81 |
| TMD8 | Acalabrutinib | 3.60 | 0.09 | 80 | 3.89 | 2.07 | 2.90 |
| TMD8 | Tirabrutinib | 2.92 | 0.87 | 20 | 3.05 | 1.28 | 1.96 |
| TMD8 | PCI-32765 | 3.39 | 0.30 | 80 | 3.86 | 2.21 | 2.89 |
| TMD8 | Zanubrutinib | 3.91 | 0.07 | 80 | 4.24 | 2.31 | 3.33 |
| U-2932 | Acalabrutinib | 4.74 | 0.49 | 65 | 7.07 | 5.67 | 7.67 |
| U-2932 | Tirabrutinib | 3.69 | 0.62 | 65 | 4.85 | 1.92 | 4.66 |
| U-2932 | PCI-32765 | 5.17 | 0.38 | 65 | 7.47 | 3.53 | 6.94 |
| U-2932 | Zanubrutinib | 4.92 | 0.54 | 65 | 7.71 | 5.21 | 7.67 |

Example 5

The combination potential of Compound A with SN-38 was tested in a panel of TNBC and NSCLC cancer cell lines using a 72-hour in vitro proliferation assays. Results of combination testing are shown in Table 23.

TABLE 23

In vitro combination testing results

| Cancer Cell Line | Bliss Synergy Score |
| --- | --- |
| HCC70 (TNBC) | 442 |
| HCC1806 (TNBC) | 246 |
| HCC1187 (TNBC) | 245 |
| H522 (NSCLC) | 614 |
| H820 (NSCLC) | 183 |

Example 6

Figure 5:
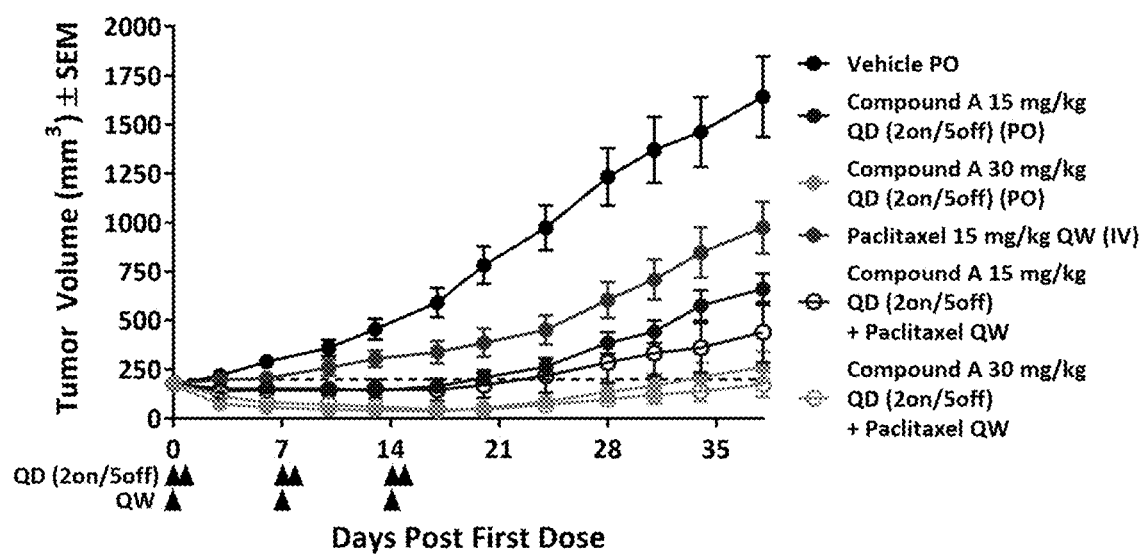
FIG. 5 TNBC PDX Model CTG-1909 Tumor Growth.
Figure 6:
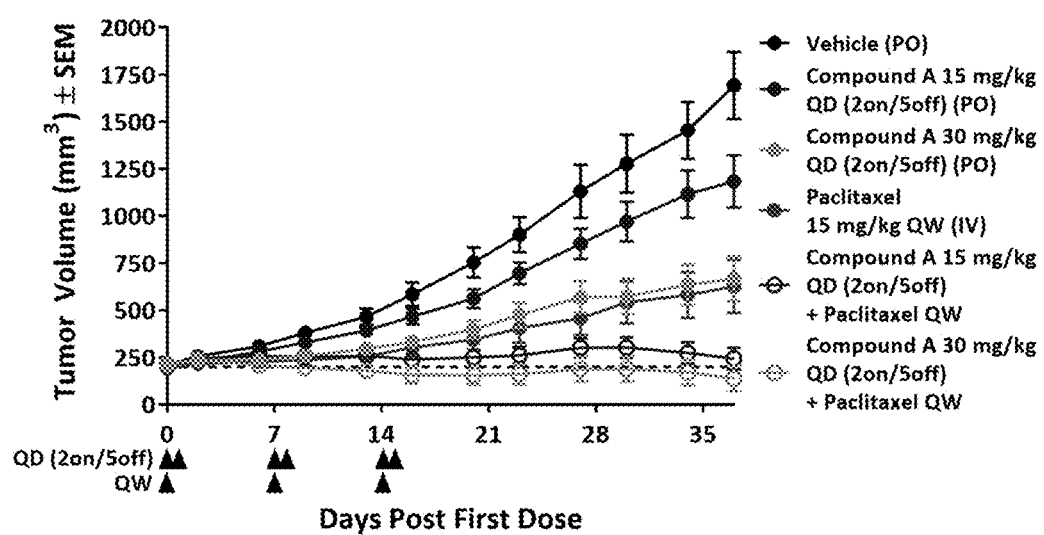
FIG. 6 TNBC PDX Model CTG-2010 Tumor Growth.

The combination potential of Compound A with paclitaxel was testing in TNBC PDX models in vivo in antitumor efficacy studies (FIGS. 5 and 6).

Example 7

A Phase 1a/b Study to Evaluate the Safety, Tolerability, and Pharmacokinetics compound A as Monotherapy and in Combination with Anticancer Therapies in Subjects with Solid Malignancies A study will be run to characterize the safety and tolerability of the compound A and the compound A in combination with anticancer therapies in subjects with advanced solid malignancies.

Study Design

This is an open-label, multicenter, dose-escalation, and dose-expansion Phase 1a/1b study to evaluate the safety, tolerability, and PK profiles of compound A and to document any DLTs (Dose-limiting toxicity) as well as determine the MTD (maximum tolerated dose) and/or RP2D (recommended Phase 2 dose) of the compound A as monotherapy and in combination with anticancer therapies in subjects with advanced solid malignancies. The RP2D will be dose level(s) with acceptable tolerability, exposure, efficacy, and biomarker activities. The study will consist of 2 phases, Phase 1a (dose escalation), followed by Phase 1b (dose expansion):

Phase 1a dose escalation: Part A: dose escalation of the compound A as monotherapy Phase 1b dose expansion: Part B: optional disease specific cohorts of the compound A in combination with anticancer therapies in parallel with Part A Part C: safety run in and expansion of the compound A in combination with anticancer therapies after Part A and Part B Each part of the study will consist of a screening, treatment, and follow-up period. Screening will occur up to 28 days before the first dose of study treatment, during which time the subject's eligibility and baseline characteristics will be determined.

Part A: Phase 1a Dose Escalation of Compound A as Monotherapy

Subjects with advanced solid tumors who have failed or are intolerant to standard therapy or for whom no standard therapy exists, will be sequentially enrolled to receive compound A as monotherapy at progressively higher dose levels.

Dose escalation will be conducted with a 3+3 rule-based dose-escalation design.

Compound A will be administered orally on Days 1, 2, 8, 9, 15, and 16 of each 21-day cycle for up to 105 weeks.

Up to 6 cohorts (ie, 6 dose levels) with 3 to 6 subjects each will receive escalating dose levels of compound A as monotherapy. The planned starting dose for compound A is 5 mg, with target doses of 15 mg and 50 mg for the following 2 cohorts. Subsequent dose levels following the starting dose will be determined based on all available clinical data, including safety, tolerability, and PK (pharmacokinetics) from prior cohorts and approved by the SRT (safety review team) and potentially up to 300 mg. Dose level increases will be half-log or less in each subsequent dose escalation.

The safety and tolerability of each dose level will be assessed by the SRT after all subjects in the cohort have been followed for at least 21 days after the first dose of compound A or subjects had DLTs during the first 21 days of study drug dosing.

The initial block of each dose consists of 3 subjects. Dose escalation will occur if no subjects experience DLT during the first 21 days of study drug dosing. If 1 subject within the initial cohort of 3 subjects experiences a DLT during the first 21 days of study drug dosing, an additional 3 subjects will be enrolled at the same dose level. If no DLTs are observed in the additional 3 subjects, dose escalation will occur. If 2 or more subjects experience DLTs within the first 21 days, dose de-escalation to a lower dose will occur. The MTD is the highest dose level with a subject incidence of DLTs of less than 33% during the first 21 days of study drug dosing.

21 days of treatment with a consistent regimen at any given cohort for decision rules to apply.

Throughout the study, subjects who have biopsy accessible malignancies may undergo optional tumor biopsies. These subjects must agree to and give a separate, specific written consent.

Dose-Escalation Criteria

For any given cohort, the sponsor may elect to hold dosing, select an intermediate dose, or stop study enrollment at any time based on review of the preliminary safety and available PK and/or pharmacodynamic data.

Based on review of relevant safety and available PK and/or pharmacodynamics data by the SRT, escalation to a higher dose cohort will occur only in the absence of DLT and/or meeting any prespecified stopping criteria. Dose escalation to a succeeding cohort with a magnitude greater than a half-log will require affirmation by at least a two-thirds majority of the SRT.

Dose limiting toxicity is defined as the following compound A related events with onset within the first 21 days (following the first dose of compound A:

Grade 4 hematologic toxicity lasting more than 21 days

All compound A related Grade 3 nonhematologic toxicities lasting for >7 days and all compound A-related Grade 4 nonhematologic toxicities regardless of duration are considered DLTs Part B: Optional Disease-Specific Cohorts of Compound A in Combination with Anticancer Therapies in Parallel with Part A During monotherapy dose escalation in Part A and prior to formal dose expansion of sponsor-nominated and endorsed disease-specific cohorts featuring combination therapy with compound A in Part C, the Sponsor may elect to nominate and endorse 1 or more of the following cohorts aligned with those in Part C for combination therapy with compound A in any previously evaluated dose in Part A deemed safe and tolerable by the SRT:

Cohort B1: metastatic NSCLC (compound A+docetaxel)
Cohort B2: metastatic NSCLC (compound A+sacituzumab govitecan)
Cohort B3: metastatic TNBC (compound A+docetaxel)
Cohort B4: metastatic TNBC (compound A+sacituzumab govitecan)
Cohort B5: mSTS with nonspecific histologies (compound A+docetaxel and gemcitabine Each additional cohort will consist of a single such population with a specific combination.

Part C: Safety Run-In and Dose Expansion of Compound A in Combination with Other Anticancer Therapies This is an open-label Phase 1b study with compound A given in combination with other anticancer therapies of 1 or more of the 5 following disease-specific cohorts, nominated and endorsed by the Sponsor after completion of Parts A and B:

Cohort C1: metastatic NSCLC (compound A+docetaxel)
Cohort C2: metastatic NSCLC (compound A+sacituzumab govitecan)
Cohort C3: metastatic TNBC (compound A+docetaxel)
Cohort C4: metastatic TNBC (compound A+sacituzumab govitecan)
Cohort C5: mSTS with nonspecific histologies (compound A+docetaxel and gemcitabine)

The RP2D will be dose level(s) with acceptable tolerability, exposure, and biomarker activities.

The SRT will recommend an initial dose of compound A for use in combination for each cohort based on the totality of clinical, safety, PK, and pharmacodynamic data. A safety run-in group of at least 3 subjects and no more than 6 subjects will be enrolled to ensure that combination therapy is safe and tolerable in each subject population.

The safety run-in will employ the same 3+3 design and dose-escalation rules as Part A and use the same DLT criteria and DLT evaluation window as Part A to determine MTD and/or RP2D. A minimum of 6 subjects need to be treated at a dose level before this dose level can be expanded. If a cognate disease-specific cohort from Part B was explored at the RP2D, those subjects may be counted and considered toward the safety run-in group requirements.

Expansion will include approximately 30 subjects less any disease-specific cognate subjects treated with an identical regimen explored in combination under Part B and in any safety run-in. For each disease-specific cohort (B1+C1, B2+C2, B3+C3, B4+C4, B5+C5), a minimum of 20 subjects at the RP2D will be enrolled, including any subjects from Part B and/or the safety run-in.

Cohort C1: Compound A in Combination with Docetaxel in Metastatic NSCLC Following a Single Line of Therapy for Metastatic Disease Cohort C1 will assess safety and tolerability and define the DLT(s) as well as the MTD and/or RP2D of compound A in combination with docetaxel in subjects with metastatic NSCLC following a single line of therapy for metastatic disease.

Compound A will be dosed on Days 1, 2, 8, 9, 15, and 16 of every 21-day cycle.

Docetaxel will be dosed 75 mg/m² of body surface area (BSA) administered as an IV infusion over 1 hour on Day 1 of every 21-day cycle provided that the subject's neutrophil count is permissive on the day of administration, specifically ≥1500 cells/mm³.

Treatment will continue for a maximum of 105 weeks unless 1 or more discontinuation criteria are met.

Cohort C2: Compound A in Combination with Sacituzumab Govitecan in Metastatic NSCLC Following a Single Line of Therapy for Metastatic Disease Cohort C2 will assess safety and tolerability and define the DLT(s) as well as the MTD and/or RP2D of compound A in combination with sacituzumab govitecan in subjects with metastatic NSCLC following a single line of therapy for metastatic disease.

Compound A will be dosed on Days 1, 2, 8, 9, 15, and 16 of every 21-day cycle.

Sacituzumab govitecan will be dosed 10 mg/kg administered as an IV infusion once weekly on Days 1 and 8 of every 21-day cycle, provided that the subject's neutrophil count is permissive on the day of administration, specifically ≥1500 cells/mm³ on Day 1 of any cycle or absolute neutrophil count (ANC)≥1000 cells/mm³ on Day 8 of any cycle. The first infusion should be administered over 3 hours, with subjects observed both during the infusion and for at least 30 minutes following the infusion for signs or symptoms of infusion-related reactions. Subsequent infusions should be administered over 1 to 2 hours if prior infusions were tolerated, with subjects observed both during the infusion and for at least 30 minutes following the infusion.

Treatment will continue for a maximum of 105 weeks unless 1 or more discontinuation criteria are met.

Cohort C3: Compound a in Combination with Docetaxel in Metastatic TNBC Following a Single Line of Therapy for Metastatic Disease.

Cohort C3 will assess safety and tolerability and define the DLT(s) as well as the MTD and/or RP2D of compound A in combination with docetaxel in subjects with metastatic TNBC following a single line of therapy for metastatic disease.

Compound A will be dosed on Days 1, 2, 8, 9, 15, and 16 of every 21-day cycle.

Docetaxel will be dosed 75 mg/m² of BSA administered as an IV infusion over 1 hour on Day 1 of every 21-day cycle provided that the subject's neutrophil count is permissive on the day of administration, specifically ≥1500 cells/mm³.

Treatment will continue for a maximum of 105 weeks unless 1 or more discontinuation criteria are met.

Cohort C4: Compound a Combination with Sacituzumab Govitecan in Metastatic TNBC Following a Single Line of Therapy for Metastatic Disease Cohort C4 will assess safety and tolerability and define the DLT(s) as well as the MTD and/or RP2D of compound A in combination with sacituzumab govitecan in subjects with metastatic TNBC following a single line of therapy for metastatic disease.

Compound A will be dosed on Days 1, 2, 8, 9, 15, and 16 of every 21-day cycle.

Sacituzumab govitecan will be dosed 10 mg/kg administered as an IV infusion once weekly on Days 1 and 8 of every 21-day cycle provided that the subject's neutrophil count is permissive on the day of administration, specifically ≥1500 cells/mm³ on Day 1 of any cycle or ANC≥1000 cells/mm³ on Day 8 of any cycle. The first infusion should be administered over 3 hours, with subjects observed both during the infusion and for at least 30 minutes following the infusion for signs or symptoms of infusion-related reactions. Subsequent infusions should be administered over 1 to 2 hours if prior infusions were tolerated, with subjects observed both during the infusion and for at least 30 minutes following the infusion.

Treatment will continue for a maximum of 105 weeks unless 1 or more discontinuation criteria are met.

Cohort C5: Metastatic Soft Tissue Sarcomas with Nonspecific Histologies Previously Untreated for Metastatic Disease Cohort C5 will assess safety and tolerability and define the DLT(s) as well as the MTD and/or RP2D of compound A in combination with gemcitabine and docetaxel in subjects with previously untreated soft tissue sarcomas.

Compound A will be dosed on Days 1, 2, 8, 9, 15, and 16 of every 21-day cycle.

Gemcitabine will be dosed per a fixed dose rate of 900 mg/m2 of BSA as an IV infusion over 90 minutes on Days 1 and 8, with docetaxel dosed 100 mg/m2 BSA IV over 60 minutes on Day 8 of every 21-day cycle.

Treatment will continue for a maximum of 105 weeks unless 1 or more discontinuation criteria are met.

Duration of Treatment

Study drug compound A will be administered for up to 105 weeks, or until disease progression, unacceptable toxicity, substantial noncompliance with study procedures or study drug, study discontinuation, withdrawal from study, or other reasons whichever occurs first.

Example 8: In Vitro Combination Screen to Test Compound A with SN-38 in Bladder and Prostate Cancer This study evaluated the combination potential of Compound A with SN-38 in a panel of bladder and prostate cancer cell lines using a 72-hour proliferation assays. All testing was performed and reported by Horizon Discovery (Cambridge, United Kingdom). Compounds were tested for both single agent dose responses as well as in 9×9 combination matrices with Compound A. Combination results were ranked using synergy score metrics.

Materials and Methods

All cell lines and compounds (excluding Compound A) were supplied and maintained by Horizon Discovery. Compound A was provided to Horizon Discovery by Gilead Sciences.

TABLE 24

Bladder and Prostate Cancer Cell Lines Tested

| Cell Line Name | Indication |
|---|---|
| 5637 | Bladder |
| RT-112 | Bladder |
| RT4 | Bladder |
| T-24 | Bladder |
| DU-145 | Prostate |
| PC-3 | Prostate |

TABLE 25

Compounds Tested

| Compound | Target or Class | Top Concentration μM |
|---|---|---|
| Compound A | MCL1 (small molecule) | 6 |
| SN-38 | Topoisomerase I (small molecule) | 1 |

Assays

Cells were thawed from a liquid nitrogen preserved state and expanded until dividing at their expected doubling times. Cells were seeded in growth media in black 384-well tissue culture treated plates and equilibrated via centrifugation. At the time of treatment, a "time zero" set of assay plates (which do not receive treatment) were collected and measured. Treated assay plates were incubated with compounds (in replicates of 3) for 3 days. After the required treatment time Cell Titer Glow (Promega) procedure and data point collection were performed via automated processes. Data was subject to quality control and analyzed using Horizon's proprietary software.

Data Analysis

Horizon utilized Growth Inhibition (GI) as a measure of cell growth. The GI percentages are calculated by applying the following test and equation:

If $T < V\_0: 100*(1-(T-V\_0)/V\_0)$

If $T \geq V\_0: 100*(1-(T-V\_0)/(V-V\_0))$ where T is the signal measure for a test article, V is the untreated/vehicle-treated control measure, and V_0 is the untreated/vehicle control measure at time zero (also colloquially referred as T0 plates). This formula is derived from the Growth Inhibition calculation used in the National Cancer Institute's NCI-60 high throughput screen.

A GI reading of 0% represents no growth inhibition and would occur in instances where the T reading at 3 days is comparable to the V reading at the respective time period. A GI of 100% represents complete growth inhibition (cytostasis) and in this case cells treated with compound for 3 days would have the same endpoint reading as T0 control cells. A GI of 200% represents complete death (cytotoxicity) of all cells in the culture well and in this case the T reading at 3 days will be lower than the T0 control (values near or at zero).

Single agent Compound A activity is provided using the GI50 value from the Growth Inhibition measure. Maximum observed response is the highest growth inhibition measured with Compound A. Both end points are reported as means of 20 independent results, being taken from the single agent Compound A curves across the 20 combinations tested.

Horizon provided a proprietary Synergy Score based on the principles of Loewe additivity to characterize the strength of synergistic interactions for tested combinations. Horizon also generates synergy results based on three standard models of combination effects: Highest Single Agent (HSA), Bliss Independence, and the above-mentioned Loewe Additivity. All methods rely on comparison of the single agent dose response curves to the matrix of combinations. For the purposes of this study report, we focus on the Horizon Synergy Score because it is a comprehensive measure of combination effects. Any positive score reported is indicative of a synergistic interaction. Bliss Independence scores—which are related to in house methods of evaluating synergy—are included in the appendix as an alternate presentation of combination results.

Results

The combination of Compound A and SN-38 testing was determined in 72 hour in vitro cellular viability assays. The combination activity of Compound A and SN-38 was determined using multiple synergy models (Table 26). In vitro synergy of Compound A and SN-38 was observed in multiple bladder cancer cell line models.

TABLE 26

Compound A + SN-38 Combination Activity

| Cell Line | Synergy Score | Loewe Volume | Bliss Volume | HAS Volume |
|---|---|---|---|---|
| RT4 | 23.6 | 12.2 | 28.8 | 12.9 |
| RT-112 | 23.4 | 10.8 | 17.9 | 12.3 |
| 5637 | 15.4 | 7.97 | 9.11 | 7.19 |
| T-24 | 5.05 | 2.18 | 3.58 | 2.8 |
| DU-145 | 3.64 | 1.99 | 2.89 | 2.09 |
| PC-3 | 2.35 | 0.431 | 0.506 | 1.6 |

Example 9: In Vivo Activity of Compound AF in Combination with Sacituzumab Govitecan Against the TNBC Cancer Cell Line Model, MDA-MB-468

Materials and Methods

One hundred and sixty-eight female athymic nude mice were inoculated orthotopically with 5.0×10^6 MDA-MB-468 cells into the third fat pad (using matrigel). Animals were randomized based on tumor volume when the mean tumor size reaches approximately 200 mm^3. Dosing commenced on Study Day 0.

TABLE 27

Test Agents and Treatment Groups

| Group (N = 12 animals) | Test Agents | Dose/Schedule |
|---|---|---|
| 1 | Vehicles (50% Imwitor 742, 50% Tween 80, 0.9% Saline) | PO QD (2on/5off) × 6, IV QW (2on/1off) × 2 |
| 2 | 50% Imwitor 742, 50% Tween 80, h679-SN-38 | PO QD (2on/5off) × 6, IV QW (2on/1off) × 2 |
| 3 | Compound A (15 mg/kg), h679-SN-38 | PO QD (2on/5off) × 6, IV QW (2on/1off) × 2 |
| 4 | Compound A (30 mg/kg), h679-SN-38 | PO QD (2on/5off) × 6, IV QW (2on/1off) × 2 |
| 5 | 50% Imwitor 742, 50% Tween 80, sacituzumab govitecan | PO QD (2on/5off) × 6, IV QW (2on/1off) × 2 |
| 6 | Compound A (15 mg/kg), Sacituzumab govitecan | PO QD (2on/5off) × 6, IV QW (2on/1off) × 2 |
| 7 | Compound A (30 mg/kg), Sacituzumab govitecan | PO QD (2on/5off) × 6, IV QW (2on/1off) × 2 |

In-Life Observations

General observations were performed daily. Body weight, tumor volume, and clinical observations were recorded two times per week.

Data Analysis

Descriptive statistics were generated from Study data. Data were assessed to determine whether parametric or non-parametric analysis is appropriate. For parametric data, analysis of variance (ANOVA) followed by post-hoc tests were performed to determine significant differences between treatments, time points, and/or groups. For non-parametric data, appropriate statistical analyses were performed (e.g., Kaplan-Meier Survival, Kruskal-Wallis One-way ANOVA, Mann-Whitney or Wilcoxon Rank Sum, etc.).

Results

Figure 7:
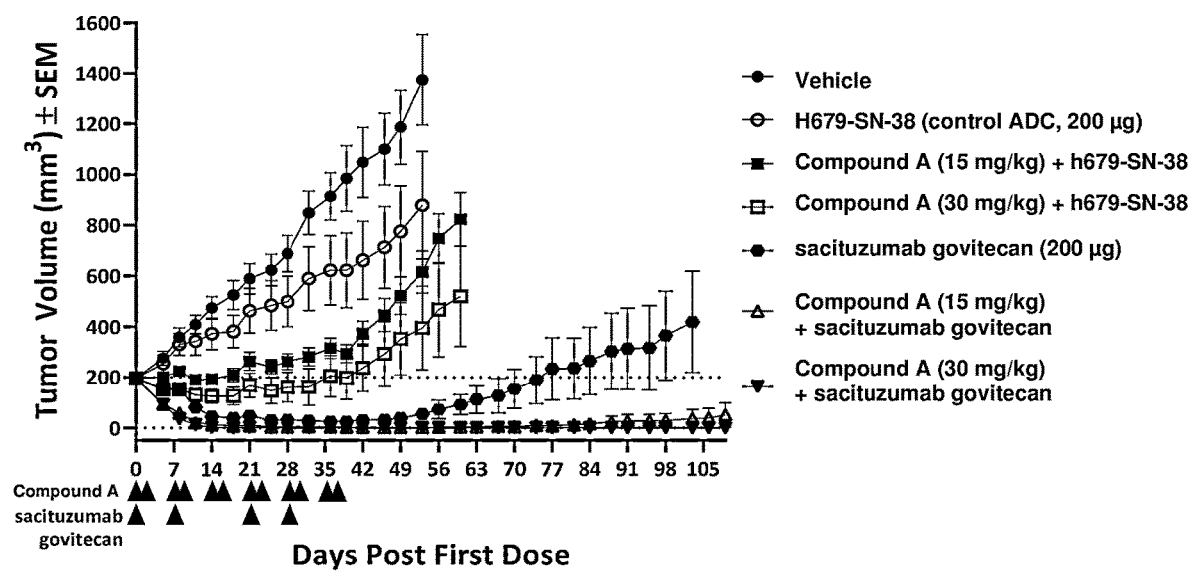
FIG. 7 MDA-MB-468 Tumor Growth.

Dosing of Compound A at 15 or 30 mg/kg (QD (2 days on/5 days off)) in combination with sacituzumab govitecan at 200 mg per mouse (IV QW (2 days on/1 day off)) for 6 weeks against MDA-MB-468 (TNBC) tumors. The non-targeting ADC, h679-SN-38, was tested in combination with Compound A as a control. Tumor volumes were determined for each treatment group (FIG. 7).

REFERENCES

Ashkenazi A, Fairbrother W J, Leverson J D, Souers A J. From basic apoptosis discoveries to advanced selective BCL-2 family inhibitors. Nat Rev Drug Discov 2017; 16 (4):273-84.

Gianni L, Kearns C M, Giani A, Capri G, Vigano L, Lacatelli A, et al. Nonlinear pharmacokinetics and metabolism of paclitaxel and its pharmacokinetic/pharmacodynamic relationships in humans. J Clin Oncol 1995; 13 (1):180-90.

Juin P, Geneste O, Gautier F, Depil S, Campone M. Decoding and unlocking the BCL-2 dependency of cancer cells. Nat Rev Cancer 2013; 13 (7):455-65.

Prichard M N, Shipman C, Jr. A three-dimensional model to analyze drug-drug interactions. Antiviral Res 1990; 14 (4-5):181-205.

Ruefli-Brasse A, Reed J C. Therapeutics targeting Bcl-2 in hematological malignancies. Biochem J 2017; 474 (21): 3643-57.

Wertz I E, Kusam S, Lam C, Okamoto T, Sandoval W, Anderson D J, et al. Sensitivity to antitubulin chemotherapeutics is regulated by MCL1 and FBW7. Nature 2011; 471 (7336):110-4.

Youle R J, Strasser A. The BCL-2 protein family opposing activities that mediate cell death. Nat Rev Mol Cell Biol 2008; 9 (1):47-59.

The invention claimed is:

1. A method of treating a Trop-2 expressing cancer comprising:
administering to a human patient in need a therapeutically effective amount of an antibody-drug conjugate, and a therapeutically effective amount of an MCL-1 inhibitor;
wherein the antibody-drug conjugate comprises an anti-Trop-2 antibody and an anticancer agent that is SN-38; and
wherein the MCL-1 inhibitor is compound A:

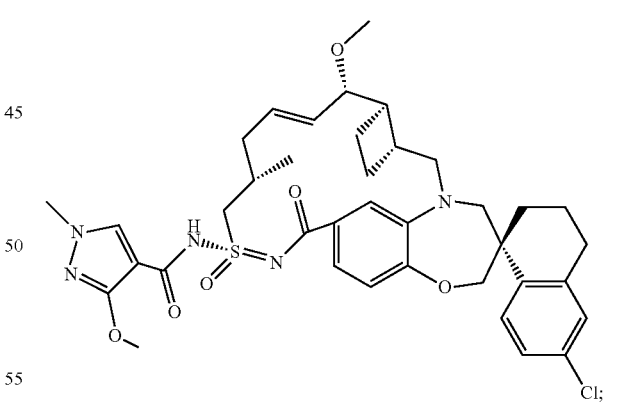

(A)

or a pharmaceutically acceptable salt thereof.

2. The method of claim 1, wherein the anti-Trop-2 antibody is selected from hRS7, Trop-2-XPAT, and BAT-8003.

3. The method of claim 1, wherein the anti-Trop-2 antibody is hRS7.

4. The method of claim 1, wherein the antibody-drug conjugate is sacituzumab govitecan.

5. The method of claim 1, wherein the Trop-2 expressing cancer is selected from breast cancer, cervical cancer, colorectal, endometrial cancer, epithelial ovarian cancer, esophageal cancer, follicular thyroid cancer, gastric or gastroesophageal junction adenocarcinoma, head and neck cancers, hepatocellular carcinoma, non-small-cell lung cancer, ovarian cancer, prostatic cancer, renal cell cancer, small-cell lung cancer, urothelial cancer, and urinary cancer.

6. The method of claim 1, wherein the Trop-2 expressing cancer is selected from TNBC, HR+/HER2− BC, urothelial cancer, NSCLC, SCLC, HNSCC, and MIBC.

7. The method of claim 1, wherein the Trop-2 expressing cancer is metastatic nonsquamous non-small-cell lung cancer (mNSCLC).

8. The method of claim 1, wherein the Trop-2 expressing cancer is metastatic triple-negative breast cancer (mTNBC).

9. The method of claim 1, wherein the Trop-2 expressing cancer is metastatic soft tissue sarcomas with nonspecific histologies.

10. The method of claim 1, wherein the amount of compound A or a pharmaceutically acceptable salt thereof is administered at a dosage of about 5 mg/kg, about 15 mg/kg, or about 50 mg/kg.

11. The method of claim 1, wherein the antibody-drug conjugate dosage is administered on days 1, and 8 of each 21-day cycle.

12. The method of claim 1, wherein the antibody-drug conjugate is administered as a dosage of between about 4 mg/kg and about 12 mg/kg.

13. The method of claim 1, wherein the antibody-drug conjugate is administered as a dosage of selected from about 4 mg/kg, about 6 mg/kg, about 8 mg/kg, about 10 mg/kg, and about 12 mg/kg.

14. The method of claim 1, wherein the Trop-2 expressing cancer is a solid tumor.

15. The method of claim 1, wherein the Trop-2 expressing cancer is thymic carcinoma, colon cancer, colorectal adenocarcinoma, anal cancer, small cell carcinoma, or EM+/HER2−breast cancer.

* * * * *